United States Patent
Mohan

(10) Patent No.: US 10,047,055 B2
(45) Date of Patent: Aug. 14, 2018

(54) LIVER X RECEPTOR (LXR) MODULATORS

(71) Applicant: Ralexar Therapeutics, Inc., Malvern, PA (US)

(72) Inventor: Raju Mohan, Malvern, PA (US)

(73) Assignee: Ralexar Therapeutics, Inc., Malvern, PA (US)

( * ) Notice: Subject to any disclaimer, the term of this patent is extended or adjusted under 35 U.S.C. 154(b) by 0 days.

(21) Appl. No.: 14/916,275

(22) PCT Filed: Sep. 4, 2014

(86) PCT No.: PCT/US2014/054043
§ 371 (c)(1),
(2) Date: Mar. 3, 2016

(87) PCT Pub. No.: WO2015/035015
PCT Pub. Date: Mar. 12, 2015

(65) Prior Publication Data
US 2016/0221956 A1    Aug. 4, 2016

Related U.S. Application Data

(60) Provisional application No. 61/873,755, filed on Sep. 4, 2013.

(51) Int. Cl.
| C07D 231/12 | (2006.01) |
| C07D 233/64 | (2006.01) |
| C07D 413/04 | (2006.01) |
| A61K 31/415 | (2006.01) |
| A61K 31/422 | (2006.01) |
| A61K 31/4164 | (2006.01) |
| A61K 45/06 | (2006.01) |
| C07D 231/14 | (2006.01) |

(52) U.S. Cl.
CPC .......... *C07D 231/12* (2013.01); *A61K 31/415* (2013.01); *A61K 31/4164* (2013.01); *A61K 31/422* (2013.01); *A61K 45/06* (2013.01); *C07D 231/14* (2013.01); *C07D 233/64* (2013.01); *C07D 413/04* (2013.01)

(58) Field of Classification Search
None
See application file for complete search history.

(56) References Cited

U.S. PATENT DOCUMENTS

| 8,008,303 | B2 | 8/2011 | Wheelhouse et al. | |
| 8,703,805 | B2 * | 4/2014 | Busch | C07D 233/64 514/406 |
| 8,987,318 | B2 | 3/2015 | Mohan | |
| 9,637,481 | B2 | 5/2017 | Mohan | |
| 2005/0038248 | A1 | 2/2005 | Henderson et al. | |
| 2005/0080111 | A1 | 4/2005 | Bayne et al. | |
| 2006/0030612 | A1 | 2/2006 | Steffan et al. | |
| 2006/0261319 | A1 | 11/2006 | Gaskins | |
| 2010/0069367 | A1 | 3/2010 | Boren | |
| 2010/0075964 | A1 | 3/2010 | Busch | |
| 2010/0168093 | A1 | 7/2010 | Pericas-Brondo et al. | |
| 2010/0331295 | A1 | 12/2010 | Busch | |
| 2011/0294784 | A1 | 12/2011 | Asberom | |
| 2012/0040977 | A1 | 2/2012 | Li et al. | |
| 2016/0214943 | A1 | 7/2016 | Mohan | |

FOREIGN PATENT DOCUMENTS

| CN | 101248048 | 8/2008 |
| CN | 102584705 | 7/2012 |
| WO | WO 2002/024632 | 3/2002 |
| WO | WO 2003/099769 | 12/2003 |
| WO | WO 2003/099775 | 12/2003 |
| WO | WO 2004/058717 | 7/2004 |
| WO | WO 2005/023782 | 3/2005 |
| WO | WO 2005/105744 | 11/2005 |
| WO | WO 2005/113499 | 12/2005 |
| WO | WO 2006/003923 | 1/2006 |
| WO | WO 2006/069155 | 6/2006 |
| WO | WO 2006/109633 | 10/2006 |
| WO | WO 2007/002559 | 1/2007 |
| WO | WO 2007/002563 | 1/2007 |
| WO | WO 2007/034279 | 3/2007 |
| WO | WO 2007/034279 A2 * | 3/2007 |
| WO | WO 2007/092065 | 8/2007 |
| WO | WO 2008/049047 | 4/2008 |
| WO | WO 2008/073825 | 6/2008 |
| WO | WO 2008/104077 | 9/2008 |
| WO | WO 2009/011850 | 1/2009 |
| WO | WO 2009/020683 | 2/2009 |
| WO | WO 2009/021868 | 2/2009 |
| WO | WO 2009/086123 | 7/2009 |
| WO | WO 2009/086138 | 7/2009 |

(Continued)

OTHER PUBLICATIONS

Transmittal of the International Search Report and the Written Opinion of the International Searching Authority for PCT/US2014/54043 dated Nov. 25, 2014, 16 pages.
Boren et al., 2008, caplus an 2008:736475, 2 pages.
CAS RN 1005621-87-3, STN Entry Date Feb. 28, 2008, 1 page.
CAS RN 1005664-76-5, STN Entry Date Feb. 28, 2008, 1 page.
CAS RN 1005700-88-8, STN Entry Date Feb. 28, 2008, 1 page.
CAS RN 1199770-53-0, STN Entry Date Dec. 31, 2009, 1 page.
CAS RN 1199771-22-6, STN Entry Date Dec. 31, 2009, 1 page.
CAS RN 263160-65-2, STN Entry Date Apr. 26, 2000, 1 page.
CAS RN 292826-84-7, STN Entry Date Oct. 5, 2000, 1 page.
CAS RN 300589-02-0, STN Entry Date Oct. 31, 2000, 1 page.
CAS RN 957264-80-1, STN Entry Date Dec. 10, 2007, 1 page.
CAS RN 957493-13-9, STN Entry Date Dec. 11, 2007, 1 page.
CAS RN 957947-23-8, STN Entry Date Dec. 13, 2007, 1 page.

(Continued)

*Primary Examiner* — Kamal A Saeed
(74) *Attorney, Agent, or Firm* — Fish & Richardson P.C.

(57) ABSTRACT

Described herein are liver X receptor (LXR) modulators and methods of utilizing LXR modulators in the treatment of LXR-associated diseases, disorders or conditions. Also described herein are pharmaceutical compositions containing such compounds.

19 Claims, 4 Drawing Sheets

(56) References Cited

FOREIGN PATENT DOCUMENTS

| | | |
|---|---|---|
| WO | WO 2009/140089 | 11/2009 |
| WO | WO 2009/150109 | 12/2009 |
| WO | WO 2010/054229 | 5/2010 |
| WO | WO 2010/059627 | 5/2010 |
| WO | WO 2010/075203 | 7/2010 |
| WO | WO 2010/096170 | 8/2010 |
| WO | WO 2010/138598 | 12/2010 |
| WO | WO 2011/045415 | 4/2011 |
| WO | WO 2011/046733 | 4/2011 |
| WO | WO 2012/019093 | 2/2012 |
| WO | WO 2012/020820 | 2/2012 |
| WO | WO 2012/027710 | 3/2012 |
| WO | WO 2012/135082 | 10/2012 |
| WO | WO2013130892 A1 | 9/2013 |
| WO | WO 2014/028461 | 2/2014 |
| WO | WO 2015/035027 | 3/2015 |

OTHER PUBLICATIONS

CAS RN 959009-61-1, STN Entry Date Dec. 20, 2007, 1 page.
CAS RN 959583-29-0, STN Entry Date Dec. 26, 2007, 1 page.
Chang et al., "Liver X Receptor Is a Therapeutic Target for Photoaging and Chronological Skin Aging," Mol. Endocrinol., 2008, 22(11):2407-2419.
Chen, H. -S., et al, "Synthesis of 2-Pyrazolyl-5-substituted-1,3,4-oxadiazoles and Their Biological Activities", Chemical Journal of Chinese Universities, 2000, 21(10), 1520-1523 [English Abstract].
Dai et al, "Liver X receptor β protects dopaminergic neurons in a mouse model of Parkinson disease," PNAS, 2012, 109:13112-13117.
Extended European Search Report in European Application No. 13754329.4, dated Oct. 12, 2015, 6 pages.
Extended European Search Report in European Application No. 14841483.2, dated Jan. 9, 2017, 6 pages.
Finn et al., "Discovery of a Potent and Selective Series of Pyrazole Bacterial Methionyl-Trna Synthetase Inhibitors," Bioorganic & Medicinal Chemistry Letters, Jan. 2003, 13(13):2231-2234.
Fluhr et al., "Topical Liver X Receptor Activators Accelerate Postnatal Acidification of Stratum Corneum and Improve Function in the Neonate," J. Investigative Dermatology, Dec. 2005, 125:1206-1214.
Fowler et al., "Liver X receptor activators display anti-inflammatory activity in irritant and allergic contact dermatitis models: liver-X-receptor-specific inhibition of inflammation and primary cytokine production," J. Invest. Dermatol., Feb. 2003, 120:246-255.
GenBank® accession No. AAM90897, GI: 22087254, Cholesterol and bile acids regulate xenosensor signaling in drug-mediated induction of cytochromes P450, dated Aug. 12, 2002, 1 page.
GenBank® accession No. AAY43056 GI: 66220403, Sus scrofa nuclear orphan receptor LXR-alpha mRNA, dated May 22, 2005, 1 page.
GenBank® accession No. P55055, GI: 296439251, NER, a new member of the gene family encoding the human steroid hormone nuclear receptor, dated Sep. 5, 2012, 7 pages.
GenBank® accession No. Q13133, GI: 23503089, LXR, a nuclear receptor that defines a distinct retinoid response pathway, dated Sep. 5, 2012, 6 pages.
GenBank® accession No. Q5BIS6, GI: 116242681, Characterization of 954 bovine full-CDS cDNA sequences, dated Nov. 28, 2012, 3 pages.
GenBank® accession No. Q5E9B6, GI: 75060925, Characterization of 954 bovine full-CDS cDNA sequences, dated Sep. 5, 2012, 3 pages.
GenBank® accession No. Q60644, GI: 10720386, Isolation of proteins that interact specifically with the retinoid X receptor: two novel orphan receptors, dated Sep. 5, 2012, 4 pages.
GenBank® accession No. Q62685, GI: 11465384, A novel orphan receptor specific for a subset of thyroid hormone-responsive elements and its interaction with the retinoid/thyroid hormone receptor subfamily, dated Oct. 3, 2012, 3 pages.
GenBank® accession No. Q62755, GI: 13124670, OR-1, a member of the nuclear receptor superfamily that interacts with the 9-cis-retinoic acid receptor, dated Sep. 5, 2012, 3 pages.
GenBank® accession No. Q9Z0Y9, GI: 341942229, LXRalpha functions as a cAMP-responsive transcriptional regulator of gene expression, dated Sep. 5, 2012, 5 pages.
Geyeregger et al., "Liver X receptors in cardiovascular and metabolic disease," Cell. Mol. Life Sci., Mar. 2006, 63:524-539.
Hatano et al., "Murine atopic dermatitis responds to peroxisome proliferator-activated receptor α, β/δ(but not γ), and liver-X-receptor activators," The Journal of Allergy and Clinical Immunology, 2010, 125(1):160-169.
Huynh, T., et al, "Optimization of pyrazole inhibitors of Coactivator Associated Arginine Methyltransferase 1 (CARM1)", Bioorganic & Medicinal Chemistry Letters, 2009, 19(11), 2924-7.
International Preliminary Report on Patentability in International Application No. PCT/US2013/028438, dated Sep. 2, 2014, 8 pages.
International Preliminary Report on Patentability in International Application No. PCT/US2014/054065, dated Mar. 17, 2016, 15 pages.
International Preliminary Report on Patentability in International Application No. PCT/US2014/54043, dated Mar. 8, 2016, 9 pages.
International Search Report and Written Opinion in International Application No. PCT/US14/54065, dated Dec. 19, 2014, 23 pages.
International Search Report in International Application No. PCT/US2013/028438, dated Jun. 18, 2013, 4 pages.
Ishida, "Regulated expression of apolipoprotein E by human retinal pigment epithelial cells," Journal of Lipid Research, 2004, 45:263-271.
Koldamova et al., "The liver X receptor ligand T0901317 decreases amyloid beta production in vitro and in a mouse model of Alzheimer's disease," J. Biol. Chem., Feb. 2005, 280:4079-88.
Kumar et al., "Liver X receptor expression in human melanocytes, does it have a role in the pathogenesis of vitiligo?," Experimental Dermatology, 2009, 19:61-64.
Lee et al., "Liver X Receptor Activation Inhibits Melanogenesis through the Acceleration of ERK-Mediated MITF Degradation," J. Invest Dermatol., Dec. 6, 2012, 133:1063-1071.
Lefterov et al., "Expression profiling in APP23 mouse brain: inhibition of Aβ amyloidosis and inflammation in response to LXR agonist treatment," Mol. Neurodegeneration, 2007, 2:20.
Madison, "Barrier Function of the Skin: "La Raison d'Etre" of the Epidermis," J. Investigative Dermatology, Aug. 2003, 121(2):231-241.
Man et al., "Basis for Improved Permeability Barrier Homeostasis Induced by PPAR and LXR Activators: Liposensors Stimulate Lipid Synthesis, Lamellar Body Secretion, and Post-Secretory Lipid Processing," J. Investigative Dermatology, 2006, 126:386-392.
Martres et al., "The Discovery of equipotent PPARalpha/gamma dual activators," Bioorganic & Medicinal Chemistry Letters, Dec. 1, 2008, 18(23):6251-6254.
Mauch et al., "CNS Synaptogenesis Promoted by Glia-Derived Cholesterol," Science, Nov. 2001, 294:1354-7.
Office Action in Chinese Application No. 201380018482.7, dated Apr. 11, 2016, 20 pages, with English translation.
Office Action in Chinese Application No. 201380018482.7, dated Aug. 18, 2015, 24 pages, with English translation.
Office Action in Japanese Application No. 2014-560060, dated Aug. 16, 2016, 13 pages, with English translation.
Pencheva et al., "Convergent multi-miRNA targeting of ApoE drives LRP1/LRP8-dependent melanoma metastasis and angiogenesis," Cell, Nov. 21, 2012, 151(5):1068-1082.
Pietrzak et al., "Lipid Disturbances in Psoriasis: An Update," Mediators of Inflammation, 2010, 13 pages.
Reply to European Search Report in European Application No. 13754329.4, dated Apr. 29, 2016, 17 pages.
Riddell et al., "The LXR agonist TO901317 selectively lowers hippocampal Abeta42 and improves memory in the Tg2576 mouse model of Alzheimer's disease," Mol. Cell Neurosci., Apr. 2007, 34:621-8.

(56) References Cited

OTHER PUBLICATIONS

Russell et al., "Characterization of liver X receptor expression and function in human skin and the pilosebaceous unit," Experimental Dermatology, 2007, 16:844-852.
Safety Pharmacology of LXR Agonists, 2 pages.
Schmuth et al., "Thematic review series: skin lipids. Peroxisome proliferator-activated receptors and liver X receptors in epidermal biology," Journal of Lipid Research, Mar. 2008, 49:499-509.
Sene et al., "Impaired cholesterol efflux in senescent macrophages promotes age-related macular degeneration," Cell Metabolism, Apr. 2013, 17:549-561.
Singapore Search Report in Application No. 11201601640S, dated Apr. 17, 2017, 13 pages.
Singapore Search Report in Application No. 11201601644R, dated May 4, 2017, 8 pages.
Supplementary Partial European Search Report in European Application No. 14842802.2, dated Dec. 20, 2016, 7 pages.
Therrien, E., et al, "1,2-Diamines as inhibitors of co-activator associated arginine methyltransferase 1 (CARM1)", Bioorganic & Medicinal Chemistry Letters, 2009, 19(23), 6725-6732.
Tice et al., "The Medical Chemistry of Liver X Receptor (LXR) Modulators," J. Med Chem, May 15, 2014, retrieved from http://pubs.acs.org, 102 pages.
Viennois et al., "Targeting liver X receptors in human health: deadlock or promising trail?," Expert Opin. Ther. Targets, 2011, 15(2):219-232.
Willy et al., "LXR, a nuclear receptor that defines a distinct retinoid response pathway," Genes & Development, May 1995, 9:1033-1045.
Written Opinion of the International Searching Authority in International Application No. PCT/US2013/028438, dated Jun. 18, 2013, 7 pages.
Zelcer and Tontonz, "Liver X receptors as integrators of metabolic and inflammatory signaling," J. Clinical Investigation, Mar. 2006, 116(3):607-614.
Zhang-Gandhi and Drew, "Liver X receptor and retinoid X receptor agonists inhibit inflammatory responses of microglia and astrocytes," J. Neuroimmunology, 2007, 183:50-59.
Sircar et al., "Inhibition of separated forms of cyclic nucleotide phosphodiesterase from guinea pig, cardiac muscle by 4, 5-dihydro-6-[4-(1H-imidazol-1-yl) phenyl]-3 (2H)-pyridazinones and related compounds Structure-activity relationships and correlation with in vivo positive inotropic activity.," J. Med. Chem., Nov. 1987, 30(11):1955-1962.
Zhu et al., "4-Methyl-5-phenyl triazoles as selective inhibitors of 1 1beta-hydroxysteroid dehydrogenase type I," Bioorg. Med. Chem. Lett., Jun. 2008, 18(11):3405-3411.

\* cited by examiner

LIVER X RECEPTOR (LXR) MODULATORS

This application is a § 371 National Stage Application of PCT/US2014/054043, filed Sep. 4, 2014, which claims the benefit of priority of U.S. Provisional No. 61/873,755, filed Sep. 4, 2013, each of which is incorporated herein by reference in its entirety.

BACKGROUND OF THE INVENTION

Liver X receptor (LXR), first described by Willy, P. J., et al. ("LXR, a nuclear receptor that defines a distinct retinoid response pathway," Genes & Development 9:1033-1045 (Cold Spring Harbor Laboratory Press)), is a member of the nuclear hormone superfamily and consists of two subtypes, LXR alpha and LXR beta. LXR modulates a variety of physiological responses including inflammation in various tissues and cell types, regulation of cholesterol absorption, cholesterol elimination (bile acid synthesis), and transport of cholesterol from peripheral tissues via plasma lipoproteins to the liver. LXR also regulates genes involved in glucose metabolism, cholesterol metabolism in the brain and apolipoproteins such as ApoE and its isoforms, that are implicated in cellular differentiation and apopotosis, inflammation, neurodgenerative disease, and infectious diseases (Geyeregger, R. et al., Cell. Mol. Life Sci. 2006, 63:524-539). LXR also regulates genes, including ApoE, in melanoma cells and melanocytes (Lim, K. M., et al., *J Invest Dermatol*. (2013) 133(4):1063-71) and thus is also a therapeutic target for treatment of certain types of cancers.

SUMMARY OF THE INVENTION

Described herein are compounds of Formula I, IA, IB, IC, II, IIA, or IIB, pharmaceutical compositions that include such compounds, and methods of use thereof, for modulating LXR. In one aspect is the administration of at least one LXR modulator described herein to a mammal in the treatment of diseases, disorders or conditions that would benefit from LXR modulation.

In one aspect is a compound of Formula (I):

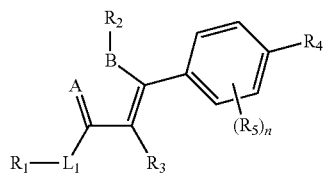

(I)

wherein:
A and B are each nitrogen, wherein A and B are bonded together to form a five-membered heteroaryl ring;
$L_1$ is a bond, $C_1$-$C_6$alkyl, or $C_1$-$C_6$heteroalkyl; $R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$;
$R_2$ is $C_1$-$C_6$alkyl, $C_2$-$C_6$alkenyl, $C_3$-$C_8$cycloalkyl, or —$C_1$-$C_6$alkyl-$C_3$-$C_8$cycloalkyl;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_5$ is independently halogen, $C_1$-$C_6$alkyl, or $C_1$-$C_6$haloalkyl;
$R_8$ is $C_1$-$C_6$alkyl, $C_2$-$C_6$alkenyl, $C_1$-$C_6$haloalkyl, —$C_1$-$C_6$alkyl-aryl, aryl, or heteroaryl;
each $R_9$ is independently hydrogen, $C_1$-$C_6$alkyl, $C_1$-$C_6$heteroalkyl, $C_1$-$C_6$haloalkyl, —$C_1$-$C_6$alkyl-aryl, aryl, or heteroaryl;
each $R_{10}$ is independently hydrogen, $C_1$-$C_6$alkyl, $C_1$-$C_6$heteroalkyl, —$C_1$-$C_6$alkyl-aryl, aryl, or heteroaryl;
each $R_{11}$ is independently halogen, nitro, —$OR_{10}$, —$N(R_{10})_2$, —CN, —C(=O)$R_{10}$, —C(=O)O$R_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and
n is 0-4;
or a pharmaceutically acceptable salt, pharmaceutically acceptable solvate, or pharmaceutically acceptable prodrug thereof.

In one embodiment is a compound of Formula I wherein $R_4$ is aryl. In another embodiment is a compound of Formula I wherein $R_4$ is phenyl substituted with at least one $R_{11}$. In a further embodiment is a compound of Formula I wherein $R_4$ is phenyl substituted with one $R_{11}$, $R_{11}$ is —$SO_2R_{10}$, and $R_{10}$ is $C_1$-$C_6$alkyl. In a further embodiment is a compound of Formula I wherein $L_1$ is a bond. In yet a further embodiment is a compound of Formula I wherein $R_1$ is $C_1$-$C_6$alkyl. In another embodiment is a compound of Formula I wherein $R_1$ is $C_2$-$C_6$alkenyl. In another embodiment is a compound of Formula I wherein $R_1$ is $C_1$-$C_6$haloalkyl. In another embodiment is a compound of Formula I wherein $R_1$ is —$CF_3$. In another embodiment is a compound of Formula I wherein $R_1$ is —C(=O)$R_8$. In another embodiment is a compound of Formula I wherein $R_1$ is —C(=O)$R_8$, and $R_8$ is $C_1$-$C_6$alkyl. In another embodiment is a compound of Formula I wherein $R_1$ is C(=O)N($R_9$)$_2$. In another embodiment of the aforementioned embodiments is a compound of Formula I wherein $R_2$ is $C_1$-$C_6$alkyl. In another embodiment of the aforementioned embodiments is a compound of Formula I wherein $R_2$ is isobutyl. In another embodiment of the aforementioned embodiments is a compound of Formula I wherein $R_3$ is hydrogen. In another embodiment of the aforementioned embodiments is a compound of Formula I wherein $R_3$ is halogen.

In another aspect is a compound of Formula (II):

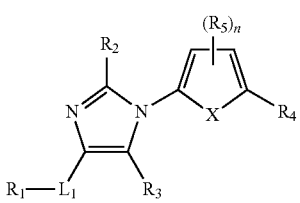

(II)

wherein:
X is —O—, —S—, or —C($R_6$)=C($R_6$)—;
$L_1$ is a bond, $C_1$-$C_6$alkyl, or $C_1$-$C_6$heteroalkyl;
$R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$;
$R_2$ is $C_1$-$C_6$alkyl, $C_2$-$C_6$alkenyl, $C_3$-$C_8$cycloalkyl, or —$C_1$-$C_6$alkyl-$C_3$-$C_8$cycloalkyl;
$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_5$ is independently halogen, $C_1$-$C_6$alkyl, or $C_1$-$C_6$haloalkyl;

each $R_6$ is independently hydrogen, halogen, $C_1$-$C_6$alkyl, or $C_1$-$C_6$haloalkyl;

$R_8$ is $C_1$-$C_6$alkyl, $C_2$-$C_6$alkenyl, $C_1$-$C_6$haloalkyl, —$C_1$-$C_6$alkyl-aryl, aryl, or heteroaryl;

each $R_9$ is independently hydrogen, $C_1$-$C_6$alkyl, $C_1$-$C_6$heteroalkyl, $C_1$-$C_6$haloalkyl, —$C_1$-$C_6$alkyl-aryl, aryl, or heteroaryl;

each $R_{10}$ is independently hydrogen, $C_1$-$C_6$alkyl, $C_1$-$C_6$heteroalkyl, —$C_1$-$C_6$alkyl-aryl, aryl, or heteroaryl;

each $R_{11}$ is independently halogen, nitro, —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and n is 0-2;

or a pharmaceutically acceptable salt, pharmaceutically acceptable solvate, or pharmaceutically acceptable prodrug thereof.

In another embodiment is a compound of Formula II wherein $L_1$ is a bond. In another embodiment is a compound of Formula II wherein $L_1$ is $C_1$-$C_6$alkyl; and $R_1$ is —OH. In another embodiment is a compound of Formula II wherein $L_1$ is —CH$_2$—. In a further embodiment is a compound of Formula II wherein $R_1$ is —C(=O)$OR_8$, and $R_8$ is $C_1$-$C_6$alkyl or $C_1$-$C_6$heteroalkyl. In a further embodiment is a compound of Formula II wherein $L_2$ is $C_1$-$C_6$alkyl. In a further embodiment is a compound of Formula II wherein $R_2$ is H. In another embodiment of the aforementioned embodiments is a compound of Formula II wherein $R_4$ is phenyl substituted with one $R_{11}$. In another embodiment of the aforementioned embodiments is a compound of Formula II wherein $R_4$ is phenyl substituted with one $R_{11}$, $R_{11}$ is —$SO_2R_{10}$, and $R_{10}$ is $C_1$-$C_6$alkyl. In another embodiment of the aforementioned embodiments is a compound of Formula II wherein $R_4$ is phenyl substituted with at least two $R_{11}$. In another embodiment of the aforementioned embodiments is a compound of Formula II wherein $R_4$ is phenyl substituted with at least two $R_{11}$ and each $R_{11}$ is independently halogen, optionally substituted $C_1$-$C_6$alkyl, —$SO_2R_{10}$, —$NR_{10}SO_2R_{10}$, or —$SO_2N(R_{10})_2$. In another embodiment of the aforementioned embodiments is a compound of Formula II wherein n is 0. In another embodiment of the aforementioned embodiments is a compound of Formula II wherein $R_3$ is hydrogen. In another embodiment of the aforementioned embodiments is a compound of Formula II wherein $R_3$ is halogen. In another embodiment of the aforementioned embodiments is a compound of Formula II wherein X is —O—. In another embodiment of the aforementioned embodiments is a compound of Formula II wherein X is —S—. In another embodiment of the aforementioned embodiments is a compound of Formula II wherein X is —CH=CH—.

In another aspect is a pharmaceutical composition comprising a pharmaceutically acceptable diluent, excipient, carrier or binder and a compound of Formula I, IA, IB, IC, II, IIA, or IIB, or a pharmaceutically acceptable salt, pharmaceutically acceptable solvate, or pharmaceutically acceptable prodrug thereof.

In another aspect is a method of treating a disease, disorder or condition in a mammal that would benefit from LXR modulation comprising administering to the mammal a compound of Formula I, IA, IB, IC, II, IIA, or IIB, or a pharmaceutically acceptable salt, pharmaceutically acceptable solvate, or pharmaceutically acceptable prodrug thereof.

In a further embodiment is a method of treating a disease, disorder or condition in a mammal that would benefit from LXR modulation comprising administering to the mammal a compound of Formula I, IA, IB, IC, II, IIA, or IIB, or a pharmaceutically acceptable salt, pharmaceutically acceptable solvate, or pharmaceutically acceptable prodrug thereof wherein the disease, disorder or condition in a mammal is increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, Parkinson's disease, impaired/improvable cognitive function, HIV, cancer including metastatic cancer and metastatic melanoma, and age related forms of macular degeneration (wet and dry forms).

In some embodiments is a method of treating a disease, disorder or condition in a mammal that would benefit from LXR modulation comprising administering to the mammal a compound of Formula I, IA, IB, IC, II, IIA, or IIB, or a pharmaceutically acceptable salt, pharmaceutically acceptable solvate, or pharmaceutically acceptable prodrug thereof wherein the disease, disorder or condition in a mammal is cancer. In some embodiments the cancer is malignant melanoma. In some embodiments the ApoE levels are reduced in the cancer. In some embodiments the method further comprises the administration of a second therapeutic agent. In some embodiments the second therapeutic agent is a BRAF inhibitor. In some embodiments the BRAF inhibitor is selected from PDC-4032, GSK2118436, and PLX-3603. In some embodiments the second therapeutic agent is sunitinib malate, sorafenib tosylate, imatinib mesylate, or nilotinib hydrochloride monohydrate; or a combination thereof. In some embodiments of the aforementioned embodiments the mammal is a human.

In some embodiments is a method of treating a disease, disorder or condition in a mammal that would benefit from LXR modulation comprising administering to the mammal a compound of Formula I, IA, IB, IC, II, IIA, or IIB, or a pharmaceutically acceptable salt, pharmaceutically acceptable solvate, or pharmaceutically acceptable prodrug thereof wherein the disease, disorder or condition in a mammal is Alzheimer's disease.

In some embodiments is a method of treating a disease, disorder or condition in a mammal that would benefit from LXR modulation comprising administering to the mammal a compound of Formula I, IA, IB, IC, II, IIA, or IIB, or a pharmaceutically acceptable salt, pharmaceutically acceptable solvate, or pharmaceutically acceptable prodrug thereof wherein the disease, disorder or condition in a mammal is Parkinson's disease.

In another embodiment is the use of a compound of Formula I, IA, IB, IC, II, IIA, or IIB in the manufacture of a medicament for the treatment of a disease, disorder, or condition that would benefit from LXR modulation (such as any of the methods described herein). In another embodiment is a compound of Formula I, IA, IB, IC, II, IIA, or IIB for use in the any of the methods described herein. In another embodiment is the use of a LXR modulator in the manufacture of a medicament for use in the treatment of a disease, disorder or condition in a mammal, wherein the disease, disorder or condition in a mammal is increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, Parkinson's disease, impaired/improvable cognitive function, HIV, cancer including metastatic cancer and metastatic melanoma, acute macular degeneration, and age related forms of macular degeneration (wet and dry forms). In another embodiment is the use of a LXR modulator and a second therapeutic agent in the manufacture of a medicament for use in the treatment of a disease, disorder or condition in a mammal, wherein the disease, disorder or condition in a mammal is increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, Parkinson's disease, impaired/improvable cognitive function, HIV, cancer including metastatic cancer and metastatic melanoma, and age related forms of macular degeneration (wet and dry forms).

In another aspect is a method of modulating LXR activity comprising contacting LXR, or portion thereof, with a compound of Formula I, IA, IB, IC, II, IIA, or IIB, or a pharmaceutically acceptable salt, pharmaceutically acceptable solvate, or pharmaceutically acceptable prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Metastatic Melanoma

Figure 1:
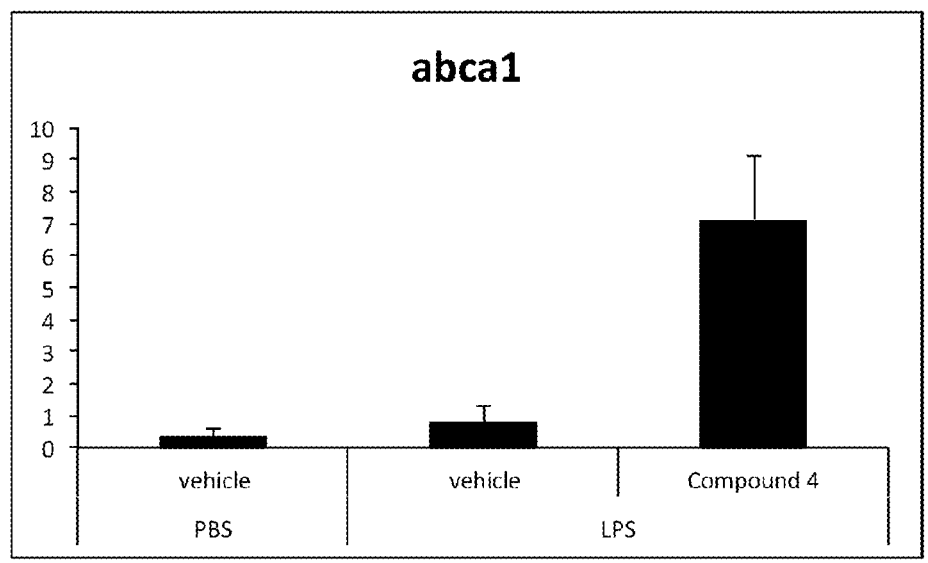
FIG. 1 shows ABCA1 gene expression analyzed by QT-PCR for Compound 4 as outlined in Example 13.

Expression levels of certain micro RNAs (miRNAs), including miRNA-1908, miRNA-199a-5p and miRNA-199a-3p and ApoE, including ApoE3 and ApoE4, correlate with the progession of malignant melanomas and metastatic disease as well as frequencies in other cancers (Tavazoie, S. F., et al., *Cell* (2012) 151:1-15). The discovery that the three miRNAs combinatorially target metastatic melanoma suppression establishes their potential as melanoma biomarkers. In particular, melanoma cell-secreted ApoE suppresses metastaic invasion and endothelial recruitment. Cancer-derived ApoE has been directly linked to modulation of metastatic angiogenesis in melanoma cells as well as in other cancer types. Agents that increase the expression of ApoE are therefore potential therapeutic agents for suppressing endothelial migration and tumor invasion and for the treatment of malignant metastatic melanoma and other cancers. LXR agonists have been shown to regulate ApoE in primary human melanoma cells (Lim, K. M., et al., *J Invest Dermatol.* (2013) 133(4):1063-71), identifying ApoE as a LXR target gene in melanoma cells and in melanocytes. As ApoE up-regulation is associated with tumor suppression in melanoma cells, LXR agonists should be effective in therapeutic intervention and prevention of metastatic melanoma and other cancers associated with ApoE-related angiogenesis. In some embodiments described herein are methods to treat cancer patients using LXR agonists who have abnormal levels of apolipoprotein E (ApoE), including lower expression levels of ApoE and its isoforms using a compound of Formula I, IA, IB, IC, II, IIA, or IIB. In some embodiments described herein are methods to treat metastatic melanoma using a compound of Formula I, IA, IB, IC, II, IIA, or IIB.

Alzheimer's Disease, Neurodegenerative Disorders, Traumatic Brain Injury

LXRs are key regulators of genes that inhibit the inflammatory response in multiple cell types, including microglial cells in the CNS. LXR has been implicated in playing a critical role in the removal of accumulated amyloid beta in the brain. In particular, LXR agonists increase the expression of the ATP-binding cassette transporter ABCA1 (a cholesterol transporter), to facilitate the lipidation of ApoE and directly promote microglia-mediated clearance of Aβ.

Data from in vitro and in vivo studies (Pfrieger, F. W. et al., *Science* (2001); 294:1354-7; Lazo, J. S. et al., *J Biol Chem.* (2005) 280:4079-88) validate the role of ApoE in facilitating the proteolytic clearance of soluble Aβ from the brain. The capacity of ApoE to promote Aβ degradation is isoform specific and dependent upon lipidation status. ApoE is lipidated by ABCA1 in multiple cell types, transferring both phospholipids and cholesterol to ApoA-I in the periphery, and both ApoA-I and ApoE in brain. In this manner, lipidated ApoE as well as ApoA-I transport cholesterol and other lipids from astrocytes. This process is necessary to maintain synaptic plasticity and neuronal remodeling in a healthy brain.

Three independent studies have reported that global deletion of ABCA1 in APP transgenic mice results in increased levels of amyloid deposition without a significant effect on Aβ generation. Studies with the LXR agonists in APP-expressing mice show LXR agonism decreases Aβ levels, and this decrease is correlated with increased ApoA-I and ApoE levels in the brains of treated animals (Koldamova R. et al., *Mol Neurodegener* (2007); 2:20). Using the same LXR agonist in a Tg2576 mouse model of Alzheimer's disease, researchers have shown a pronounced improvement in cognitive performance (Jacobsen J. S., et al., *Mol Cell Neurosci.* (2007) 34:621-8).

The outcomes of these studies strongly suggest that ABCA1 and LXR regulate ApoE and ApoA-I lipidation, which in turn impacts Aβ aggregation and allows for Aβ clearance and that LXR agonists should be effective in treating neurodegenerative disorders such as Alzheimer's disease. In some embodiments described herein are methods to treat Alzheimer's disease using a compound of Formula I, IA, IB, IC, II, IIA, or IIB.

Parkinson's Disease

LXRs have been shown to play an important role in the CNS both in reducing inflammation in microglia and astrocytes and in effecting Abeta clearance with potential implications in the treatment of Parkinson's disease. Recent data show that LXR plays a role in the formation of superficial cortical layers and migration of later-born neurons in embryonic mice. LXR agonists have a positive therapeutic effect on dopaminergic neurons in the substantia nigra in a MPTP-induced rodent model of Parkinson's disease where the MPTP-induced loss of dopaminergic neurons was significantly reduced in the mice treated with the LXR agonist relative to vehicle-treated animals (Gustafsson, J. A.; *Proc. Natl. Acad. Sci. U.S.A.* (2012) 109:13112-13117). LXR agonist treatment also resulted in an attenuation of the increase in GFAP-positive cells in the substantia nigra pars compacta. Based on the above studies and other data in the literature, it is likely that LXR plays a key role in the pathology of Parkinson's disease. Thus, selective LXR agonists with requisite brain distribution should offer a novel therapeutic for Parkinson's disease. In some embodiments described herein are methods to treat Parkinson's disease using a compound of Formula I, IA, IB, IC, II, IIA, or IIB.

Age-Related Macular Degeneration (AMD) Wet and Dry Forms

LXR pathways that have been studied in the CNS, such as regulation of ABC transporters and apolipoproteins such as ApoE and isoforms, are also pertinent in the retinal cells and implicated in the pathology of AMD, both wet and dry. In retinal pigment epithelium cells, both primary and immortalized, LXR agonists and modulators induce the expression of ABCA1 and ApoE, target genes implicated in the pathology of AMD (Ishida, *Journal of Lipid Research* (2004) 45: 267-271). In mouse models of AMD, non-selective LXR agonists have been shown to provide beneficial effects on AMD progression (Sene, *Cell Metabolism*, 2013, 17: 549-561). Thus, selective LXR agonists and modulators should have a therapeutic benefit in the treatment of both wet and dry forms of AMD, a disease characterized by abnormal cholesterol signaling and inflammatory conditions.

Definitions

In the context of this disclosure, a number of terms shall be utilized.

As used herein, the term "about" or "approximately" means within 20%, preferably within 10%, and more preferably within 5% of a given value or range.

The term a "therapeutically effective amount" as used herein refers to the amount of an LXR modulator that, when administered to a mammal in need, is effective to at least partially ameliorate or to at least partially prevent diseases, disorders or conditions described herein.

As used herein, the term "expression" includes the process by which polynucleotides are transcribed into mRNA and translated into peptides, polypeptides, or proteins.

The term "modulate" encompasses either a decrease or an increase in activity or expression depending on the target molecule. For example, a TIMP1 modulator is considered to modulate the expression of TIMP1 if the presence of such TIMP1 modulator results in an increase or decrease in TIMP1 expression.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The terms "induce" or "induction" of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, or decorin expression refer to an increase, induction, or otherwise augmentation of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, or decorin mRNA and/or protein expression. The increase, induction, or augmentation can be measured by one of the assays provided herein. Induction of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, or decorin expression does not necessarily indicate maximal expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, or decorin. An increase in TIMP1, ABCA12, or decorin expression can be, for example, at least about 10%, 20%, 30%, 40%, 50%, 60%, 70%, 80%, 90% or more. In one embodiment, induction is measured by comparing TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, or decorin mRNA expression levels from untreated cells to that of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, or decorin mRNA expression levels from LXR modulator-treated cells.

The terms "inhibit" or "inhibition" of TNFα, MMP1, MMP3, or IL-8 expression refer to a reduction, inhibition, or otherwise diminution of TNFα, MMP1, MMP3, or IL-8 mRNA and/or protein expression. The reduction, inhibition, or diminution of binding can be measured by one of the assays provided herein. Inhibition of TNFα, MMP1, MMP3, or IL-8 expression does not necessarily indicate a complete negation of TNFα, MMP1, MMP3, or IL-8 expression. A reduction in expression can be, for example, at least about 10%, 20%, 30%, 40%, 50%, 60%, 70%, 80%, 90% or more. In one embodiment, inhibition is measured by comparing TNFα, MMP1, MMP3, or IL-8 mRNA expression levels from untreated cells to that of TNFα, MMP1, MMP3, or IL-8 mRNA expression levels from LXR modulator-treated cells.

"Liver X receptor" or "LXR" refers to both LXRα and LXRβ, and variants, isoforms, and active fragments thereof. LXRβ is ubiquitously expressed, while LXRα expression is limited to liver, kidney, intestine, spleen, adipose tissue, macrophages, skeletal muscle, and skin. Representative GenBank® accession numbers for LXRα sequences include the following: human (*Homo sapiens*, Q 13133), mouse (*Mus musculus*, Q9ZOY9), rat (*Rattus norvegicus*, Q62685), cow (*Bos taurus*, Q5E9B6), pig (*Sus scrofa*, AAY43056), chicken (*Gallus gallus*, AAM90897). Representative GenBank® accession numbers for LXRβ include the following: human (*Homo sapiens*, P55055), mouse (*Mus musculus*, Q60644), rat (*Rattus norvegicus*, Q62755), cow (*Bos taurus*, Q5BIS6).

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Proinflammatory cytokine" as used herein refers to any cytokine that can activate cytotoxic, inflammatory, or delayed hypersensitivity reactions. Exemplary proinflammatory cytokines include colony stimulating factors (CSFs), for example granulocyte-macrophage CSF, granulocyte CSF, erythropoietin; transforming growth factors (TGFs), for example TGFβ; interferons (IFNs), for example IFNα, IFNβ, IFNγ; interleukins (ILs), for example IL-1α, IL-1β, IL-3, IL-6, IL-7, IL-8, IL-9, IL-11, IL-12, IL-15; tumor necrosis factors (TNFs), for example TNFα, TNFβ; adherence proteins, for example intracellular adhesion molecule (ICAM), vascular cell adhesion molecule (VCAM); growth factors, for example leukemia inhibitory factor (LIF), macrophage migration-inhibiting factor (MIF), epidermal growth factor (EGF), platelet-derived growth factor (PDGF), fibroblast growth factor (FGF), insulin-like growth factor (IGF), nerve growth factor (NGF), B-cell growth factor (BCGF); chemokines, for example monocyte chemoattractant proteins (MCP-1, MCP-2, MCP-3), macrophage inflammatory protein (MIP), growth-related oncogene, gamma interferon-inducible protein; leukotrienes, for example leukotriene $B_4$, leukotrine $D_4$; vasoactive factors, for example histamine, bradykinin, platelet activating factor (PAF); prostaglandins, for example prostaglandin $E_2$.

LXR Modulators

LXR modulators contemplated for use in the compositions and methods described herein are compounds with LXRα and/or LXRβ modulator activities. The term "LXR modulator" includes LXRα and/or LXRβ agonists, antagonists and tissue selective LXR modulators, as well as other agents that induce the expression and/or protein levels of LXRs in cells.

Preferred compounds will be LXR modulators with LXRα and/or LXRβ modulator activities. Preferred LXR modulators are LXR activators. The term "LXR activator" or "activator of the LXR" includes LXRα and/or LXRβ agonists, partial agonists and tissue selective LXR modulators, as well as other agents that induce the expression and/or protein levels of LXRs in the cells.

In one embodiment is a compound of Formula (I):

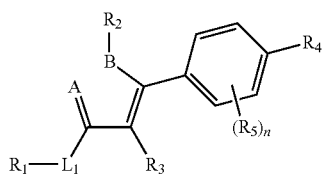

wherein:

A and B are each nitrogen, wherein A and B are bonded together to form a five-membered heteroaryl ring;

$L_1$ is a bond, $C_1$-$C_6$alkyl, or $C_1$-$C_6$heteroalkyl;

$R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$;

$R_2$ is $C_1$-$C_6$alkyl, $C_2$-$C_6$alkenyl, $C_3$-$C_8$cycloalkyl, or —$C_1$-$C_6$alkyl-$C_3$-$C_8$cycloalkyl;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$; each $R_5$ is independently halogen, $C_1$-$C_6$alkyl, or $C_1$-$C_6$haloalkyl;

$R_8$ is $C_1$-$C_6$alkyl, $C_2$-$C_6$alkenyl, $C_1$-$C_6$haloalkyl, —$C_1$-$C_6$alkyl-aryl, aryl, or heteroaryl; each $R_9$ is independently hydrogen, $C_1$-$C_6$alkyl, $C_1$-$C_6$heteroalkyl, $C_1$-$C_6$haloalkyl, —$C_1$-$C_6$alkyl-aryl, aryl, or heteroaryl;

each $R_{10}$ is independently hydrogen, $C_1$-$C_6$alkyl, $C_1$-$C_6$heteroalkyl, —$C_1$-$C_6$alkyl-aryl, aryl, or heteroaryl;

each $R_{11}$ is independently halogen, nitro, —$OR_{10}$, —$N(R_{10})_2$, —CN, —C(=O)$R_{10}$, —C(=O)O$R_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and n is 0-4;

or a pharmaceutically acceptable salt, pharmaceutically acceptable solvate, or pharmaceutically acceptable prodrug thereof.

In another embodiment is a compound of Formula (IA):

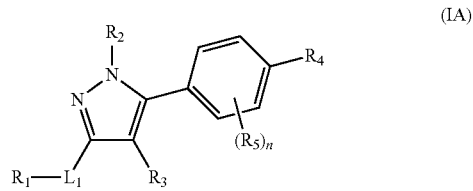

wherein:

$L_1$ is a bond, $C_1$-$C_6$alkyl, or $C_1$-$C_6$heteroalkyl;

$R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$;

$R_2$ is $C_1$-$C_6$alkyl, $C_2$-$C_6$alkenyl, $C_3$-$C_8$cycloalkyl, or —$C_1$-$C_6$alkyl-$C_3$-$C_8$cycloalkyl;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_5$ is independently halogen, $C_1$-$C_6$alkyl, or $C_1$-$C_6$haloalkyl;

$R_8$ is $C_1$-$C_6$alkyl, $C_2$-$C_6$alkenyl, $C_1$-$C_6$haloalkyl, —$C_1$-$C_6$alkyl-aryl, aryl, or heteroaryl;

each $R_9$ is independently hydrogen, $C_1$-$C_6$alkyl, $C_1$-$C_6$heteroalkyl, $C_1$-$C_6$haloalkyl, —$C_1$-$C_6$alkyl-aryl, aryl, or heteroaryl;

each $R_{10}$ is independently hydrogen, $C_1$-$C_6$alkyl, $C_1$-$C_6$heteroalkyl, —$C_1$-$C_6$alkyl-aryl, aryl, or heteroaryl;

each $R_{11}$ is independently halogen, nitro, —$OR_{10}$, —$N(R_{10})_2$, —CN, —C(=O)$R_{10}$, —C(=O)O$R_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and n is 0-4;

or a pharmaceutically acceptable salt, pharmaceutically acceptable solvate, or pharmaceutically acceptable prodrug thereof.

In some embodiments, "optionally substituted" means optionally substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl) amino.

In some embodiments is a compound of Formula IA wherein $R_4$ is heteroaryl substituted with at least one $R_{11}$. In some embodiments is a compound of Formula IA wherein $R_4$ is aryl substituted with at least one $R_{11}$. In a further embodiment is a compound of Formula IA wherein $R_4$ is phenyl substituted with at least one $R_{11}$. In a further embodiment is a compound of Formula IA wherein $R_4$ is phenyl substituted with at least one $R_{11}$ and each $R_{11}$ is independently halogen, nitro, —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl. In a further embodiment is a compound of Formula IA wherein $R_4$ is phenyl substituted with at least one $R_{11}$ and each $R_{11}$ is independently halogen, nitro, —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, optionally substituted $C_1$-$C_6$alkyl, optionally substituted $C_1$-$C_6$heteroalkyl, or optionally substituted —$C_1$-$C_6$alkyl-aryl. In a further embodiment is a compound of Formula IA wherein $R_4$ is phenyl substituted with at least one $R_{11}$ and each $R_{11}$ is independently halogen, —C(=O)$R_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, or optionally substituted $C_1$-$C_6$alkyl. In a further embodiment is a compound of Formula IA wherein $R_4$ is phenyl substituted with at least one $R_{11}$ and each $R_{11}$ is independently halogen, —$SO_2R_{10}$, or optionally substituted $C_1$-$C_6$alkyl. In a further embodiment is a compound of Formula IA wherein $R_4$ is phenyl substituted with at least one $R_{11}$ and each $R_{11}$ is independently —$SO_2R_{10}$ or optionally substituted $C_1$-$C_6$alkyl. In a further embodiment is a compound of Formula IA wherein $R_4$ is phenyl substituted with at least one $R_{11}$, each $R_{11}$ is independently —$SO_2R_{10}$ or optionally substituted $C_1$-$C_6$alkyl, and $R_{1}$ is $C_1$-$C_6$alkyl. In a further embodiment is a compound of Formula IA wherein $R_4$ is phenyl substituted with at least one $R_{11}$, each $R_{11}$ is independently —$SO_2R_{10}$ or optionally substituted $C_1$-$C_6$alkyl, and $R_{11}$ is $CH_3$. In some embodiments is a compound of Formula IA wherein $R_4$ is aryl substituted with one $R_{11}$. In some embodiments is a compound of Formula IA wherein $R_4$ is aryl substituted with two $R_{11}$. In some embodiments is a compound of Formula IA wherein $R_4$ is aryl substituted with three $R_{11}$. In further embodiments is a compound of Formula IA wherein $R_4$ is phenyl substituted with one $R_{11}$. In further embodiments is a compound of Formula IA wherein $R_4$ is phenyl substituted with two $R_{11}$. In further embodiments is a compound of Formula IA wherein $R_4$ is phenyl substituted with three $R_{11}$. In some embodiments is a compound of Formula IA wherein $R_4$ is heteroaryl substituted with one $R_{11}$. In some embodiments is a compound of Formula IA wherein $R_4$ is heteroaryl substituted with two $R_{11}$. In some embodiments is a compound of Formula IA wherein $R_4$ is heteroaryl substituted with three $R_{11}$.

In another embodiment is a compound of Formula IA wherein $L_1$ is a bond and $R_1$ is $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)$N(R_9)_2$. In another embodiment is a compound of Formula IA wherein $L_1$ is a bond and $R_1$ is $C_1$-$C_6$alkyl. In another embodiment is a compound of Formula IA wherein $L_1$ is a bond and $R_1$ is $C_2$-$C_6$alkenyl. In another embodiment is a compound of Formula IA wherein $L_1$ is a bond and $R_1$ is $C_1$-$C_6$haloalkyl. In another embodiment is a compound of Formula IA wherein $L_1$ is a bond and $R_1$ is $C_2$-$C_9$heterocycloalkyl. In another embodiment is a compound of Formula IA wherein $L_1$ is a bond and $R_1$ is —C(=O)$R_8$. In another embodiment is a compound of Formula IA wherein $L_1$ is a bond, $R_1$ is —C(=O)$R_8$, and $R_8$ is $C_1$-$C_6$alkyl, $C_2$-$C_6$alkenyl, $C_1$-$C_6$haloalkyl, —$C_1$-$C_6$alkyl-aryl, aryl, or heteroaryl. In another embodiment is a compound of Formula IA wherein $L_1$ is a bond and $R_1$ is —C(=O)$N(R_9)_2$.

In another embodiment is a compound of Formula IA wherein $L_1$ is $C_1$-$C_6$alkyl and $R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)$N(R_9)_2$. In another embodiment is a compound of Formula IA wherein v. In another embodiment is a compound of Formula IA wherein $L_1$ is $C_1$-$C_6$alkyl and $R_1$ is —OH. In another embodiment is a compound of Formula IA wherein $L_1$ is $C_1$-$C_6$alkyl and $R_1$ is —$N(R_9)_2$. In another embodiment is a compound of Formula IA wherein $L_1$ is $C_1$-$C_6$alkyl and $R_1$ is $C_1$-$C_6$alkyl. In another embodiment is a compound of Formula IA wherein $L_1$ is $C_1$-$C_6$alkyl and $R_1$ is $C_2$-$C_6$alkenyl. In another embodiment is a compound of Formula IA wherein $L_1$ is $C_1$-$C_6$alkyl and $R_1$ is $C_1$-$C_6$haloalkyl. In another embodiment is a compound of Formula IA wherein $L_1$ is $C_1$-$C_6$alkyl and $R_1$ is $C_2$-$C_9$heterocycloalkyl. In another embodiment is a compound of Formula IA wherein $L_1$ is $C_1$-$C_6$alkyl and $R_1$ is —C(=O)$R_8$. In another embodiment is a compound of Formula IA wherein $L_1$ is $C_1$-$C_6$alkyl, $R_1$ is —C(=O)$R_8$, and $R_8$ is $C_1$-$C_6$alkyl, $C_2$-$C_6$alkenyl, $C_1$-$C_6$haloalkyl, —$C_1$-$C_6$alkyl-aryl, aryl, or heteroaryl. In another embodiment is a compound of Formula IA wherein $L_1$ is $C_1$-$C_6$alkyl and $R_1$ is —C(=O)$N(R_9)_2$.

In some embodiments is a compound of Formula IA wherein $R_2$ is $C_1$-$C_6$alkyl. In another embodiment is a compound of Formula IA wherein $R_2$ is $C_2$-$C_6$alkenyl. In another embodiment is a compound of Formula IA wherein $R_2$ is $C_3$-$C_8$cycloalkyl. In another embodiment is a compound of Formula IA wherein $R_2$ is —$C_1$-$C_6$alkyl-$C_3$-$C_8$cycloalkyl.

In another embodiment is a compound of Formula IA wherein $L_1$ is a bond, $R_1$ is $C_1$-$C_6$alkyl, and $R_2$ is $C_1$-$C_6$alkyl. In another embodiment is a compound of Formula IA wherein $L_1$ is a bond, $R_1$ is $C_1$-$C_6$alkyl, and $R_2$ is $C_2$-$C_6$alkenyl. In another embodiment is a compound of Formula IA wherein $L_1$ is a bond, $R_1$ is $C_1$-$C_6$alkyl, and $R_2$ is $C_3$-$C_8$cycloalkyl. In another embodiment is a compound of Formula IA wherein $L_1$ is a bond, $R_1$ is $C_1$-$C_6$alkyl, and $R_2$ is —$C_1$-$C_6$alkyl-$C_3$-$C_8$cycloalkyl. In another embodiment is a compound of Formula IA wherein $L_1$ is a bond, $R_1$ is $C_2$-$C_6$alkenyl, and $R_2$ is $C_1$-$C_6$alkyl. In another embodiment is a compound of Formula IA wherein $L_1$ is a bond, $R_1$ is $C_2$-$C_6$alkenyl, and $R_2$ is $C_2$-$C_6$alkenyl. In another embodiment is a compound of Formula IA wherein $L_1$ is a bond, $R_1$ is $C_2$-$C_6$alkenyl, and $R_2$ is $C_3$-$C_8$cycloalkyl. In another embodiment is a compound of Formula IA wherein $L_1$ is a bond, $R_1$ is $C_2$-$C_6$alkenyl, and $R_2$ is —$C_1$-$C_6$alkyl-$C_3$-$C_8$cycloalkyl. In another embodiment is a compound of Formula IA wherein $L_1$ is a bond, $R_1$ is $C_1$-$C_6$haloalkyl, and $R_2$ is $C_1$-$C_6$alkyl. In another embodiment is a compound of Formula IA wherein $L_1$ is a bond, $R_1$ is $C_1$-$C_6$haloalkyl, and $R_2$ is $C_2$-$C_6$alkenyl. In another embodiment is a compound of Formula IA wherein $L_1$ is a bond, $R_1$ is $C_1$-$C_6$haloalkyl, and $R_2$ is $C_3$-$C_8$cycloalkyl. In another embodiment is a compound of Formula IA wherein $L_1$ is a bond, $R_1$ is $C_1$-$C_6$haloalkyl, and $R_2$ is —$C_1$-$C_6$alkyl-$C_3$-$C_8$cycloalkyl. In another embodiment is a compound of Formula IA wherein $L_1$ is a bond, $R_1$ is $C_2$-$C_9$heterocycloalkyl, and $R_2$ is $C_1$-$C_6$alkyl. In another embodiment is a compound of Formula IA wherein $L_1$ is a bond, $R_1$ is $C_2$-$C_9$heterocycloalkyl, and $R_2$ is $C_2$-$C_6$alkenyl. In another embodiment is a compound of Formula IA wherein $L_1$ is a bond, $R_1$ is $C_2$-$C_9$heterocycloalkyl, and $R_2$ is $C_3$-$C_8$cycloalkyl. In another embodiment is a compound of Formula IA wherein $L_1$ is a bond, $R_1$ is $C_2$-$C_9$heterocycloalkyl, and $R_2$ is —$C_1$-$C_6$alkyl-$C_3$-$C_8$cycloalkyl. In another embodiment is a compound of Formula IA wherein $L_1$ is a $C_1$-$C_6$alkyl, $R_1$ is —$OR_9$, $R_9$ is hydrogen, and $R_2$ is $C_1$-$C_6$alkyl. In another embodiment is a compound of Formula IA wherein $L_1$ is a $C_1$-$C_6$alkyl, $R_1$ is —$OR_9$, $R_9$ is hydrogen, and $R_2$ is $C_2$-$C_6$alkenyl. In another embodiment is a compound of Formula IA wherein $L_1$ is a $C_1$-$C_6$alkyl, $R_1$ is —$OR_9$, $R_9$ is hydrogen, and $R_2$ is $C_3$-$C_8$cycloalkyl. In another embodiment is a compound of Formula IA wherein $L_1$ is a $C_1$-$C_6$alkyl, $R_1$ is —$OR_9$, $R_9$ is hydrogen, and $R_2$ is —$C_1$-$C_6$alkyl-$C_3$-$C_8$cycloalkyl. In a further embodiment of the aforementioned embodiments is a compound of Formula IA wherein $R_4$ is phenyl substituted with one $R_{11}$. In a further embodiment of the aforementioned embodiments is a compound of Formula IA wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula IA wherein $R_4$ is phenyl substituted with one $R_{11}$, $R_{11}$ is —$SO_2R_{10}$ and $R_{10}$ is $CH_3$. In a further embodiment of the aforementioned embodiments is a compound of Formula IA wherein $R_4$ is phenyl substituted with two $R_{11}$. In a further embodiment of the aforementioned embodiments is a compound of Formula IA wherein $R_4$ is phenyl substituted with two $R_{11}$, and one $R_{11}$ is —$SO_2R_{10}$ and one $R_{11}$ is optionally substituted $C_1$-$C_6$alkyl. In yet a further embodiment of the aforementioned embodiments is a compound of Formula IA wherein $R_4$ is phenyl substituted with two $R_{11}$, and one $R_{11}$ is —$SO_2CH_3$ and one $R_{11}$ is —$CH_2OH$.

In another embodiment of the aforementioned embodiments is a compound of Formula IA wherein $R_3$ is hydrogen, halogen, $C_1$-$C_6$alkyl, or $C_1$-$C_6$haloalkyl. In some embodiments of the aforementioned embodiments is a compound of Formula IA wherein $R_3$ is hydrogen. In some embodiments of the aforementioned embodiments is a compound of Formula IA wherein $R_3$ is halogen. In some embodiments of the aforementioned embodiments is a compound of Formula IA wherein $R_3$ is $C_1$-$C_6$alkyl. In some embodiments of the aforementioned embodiments is a compound of Formula IA wherein $R_3$ is $C_1$-$C_6$haloalkyl.

In another embodiment of the aforementioned embodiments is a compound of Formula IA wherein $L_1$ is a bond. In another embodiment of the aforementioned embodiments is a compound of Formula IA wherein $R_1$ is $C_1$-$C_6$alkyl. In another embodiment of the aforementioned embodiments is a compound of Formula IA wherein $R_1$ is $C_2$-$C_6$alkenyl. In another embodiment of the aforementioned embodiments is a compound of Formula IA wherein $R_1$ is $C_1$-$C_6$haloalkyl. In another embodiment of the aforementioned embodiments is a compound of Formula IA wherein $R_1$ is —$CF_3$. In another embodiment of the aforementioned embodiments is a compound of Formula IA wherein $R_1$ is $C(=O)N(R_9)_2$. In another embodiment of the aforementioned embodiments is a compound of Formula IA wherein $L_1$ is $C_1$-$C_6$alkyl; and $R_1$ is —OH.

In another embodiment of the aforementioned embodiments is a compound of Formula IA wherein -$L_1$-$R_1$ is —C(=$CH_2$)$CH_3$, isopropyl, —C(=O)NHCH$_2$CF$_3$, —CF$_3$, or —C(CH$_3$)$_2$OH. In another embodiment of the aforementioned embodiments is a compound of Formula IA wherein $R_2$ is $C_1$-$C_6$alkyl. In another embodiment of the aforementioned embodiments is a compound of Formula IA wherein $R_2$ is isobutyl. In another embodiment of the aforementioned embodiments is a compound of Formula IA wherein $R_2$ is sec-butyl. In another embodiment of the aforementioned embodiments is a compound of Formula IA wherein $R_2$ is $C_3$-$C_8$cycloalkyl. In another embodiment of the aforementioned embodiments is a compound of Formula IA wherein $R_2$ is —$C_1$-$C_6$alkyl-$C_3$-$C_8$cycloalkyl. In another embodiment of the aforementioned embodiments is a compound of Formula IA wherein $R_2$ is isobutyl, sec-butyl, cyclohexyl, —CH$_2$-cyclohexyl, or —CH$_2$-cyclopropyl. In another embodiment of the aforementioned embodiments is a compound of Formula IA wherein $R_3$ is hydrogen.

In another embodiment of the aforementioned embodiments is a compound of Formula IA wherein "optionally substituted" means optionally substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl)amino. In another embodiment of the aforementioned embodiments is a compound of Formula IA wherein $R_4$ is phenyl, which is substituted with at least one $R_{11}$. In another embodiment of the aforementioned embodiments is a compound of Formula IA wherein at least one $R_{11}$ is —$NR_{10}SO_2R_{10}$, —$SOR_{10}$, —$SO_2R_{10}$, or —$SO_2N(R_{10})_2$. In another embodiment of the aforementioned embodiments is a compound of Formula IA wherein at least one $R_{11}$ is —$SO_2R_{10}$. In another embodiment of the aforementioned embodiments is a compound of Formula IA wherein each $R_{10}$ is independently $C_1$-$C_6$alkyl. In another embodiment of the aforementioned embodiments is a compound of Formula IA wherein $R_4$ is phenyl substituted with one $R_{11}$, wherein $R_{11}$ is —$SO_2R_{10}$ and $R_{10}$ is $C_1$-$C_6$alkyl; or $R_4$ is phenyl substituted with two $R_{11}$, and one $R_{11}$ is —$SO_2R_{10}$ and one $R_{11}$ is optionally substituted $C_1$-$C_6$alkyl. In another embodiment of the aforementioned embodiments is a compound of Formula IA wherein $R_4$ is phenyl substituted with two $R_{11}$, wherein one $R_{11}$ is —$SO_2CH_3$ and one $R_{11}$ is —$CH_2OH$. In another embodiment of the aforementioned embodiments is a compound of Formula IA wherein $R_4$ is phenyl substituted with one $R_{11}$, wherein $R_{11}$ is —$SO_2R_{10}$ and $R_{10}$ is $C_1$-$C_6$alkyl. In another embodiment of the aforementioned embodiments is a compound of Formula IA, wherein n is 0.

In another embodiment of the aforementioned embodiments, the compound is a compound of Formula (IB):

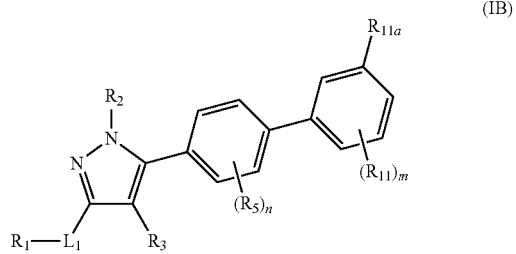

wherein:
$R_{11a}$ is —$NR_{10}SO_2R_{10}$, —$SOR_{10}$, —$SO_2R_{10}$, or —$SO_2N(R_{10})_2$; and
m is 0 or 1;
or a pharmaceutically acceptable salt thereof.

In another embodiment of the aforementioned embodiments, the compound is a compound of Formula (IC):

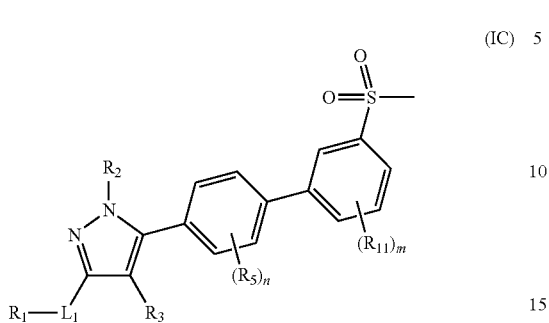

wherein m is 0 or 1;
or a pharmaceutically acceptable salt thereof.

In another embodiment of the aforementioned embodiments is a compound of Formula IA wherein:
$L_1$ is a bond or $C_1$-$C_6$alkyl;
$R_1$ is —$OR_9$, —$C_1$-$C_6$alkyl, $C_2$-$C_6$alkenyl, $C_1$-$C_6$haloalkyl, or —C(=O)N($R_9$)$_2$;
$R_2$ is $C_1$-$C_6$alkyl, $C_3$-$C_8$cycloalkyl, or —$C_1$-$C_6$alkyl-$C_3$-$C_8$cycloalkyl;
$R_3$ is hydrogen;
$R_4$ is phenyl substituted with at least one $R_{11}$;
each $R_{11}$ is independently —$NR_{10}SO_2R_{10}$, —$SOR_{10}$, —$SO_2R_{10}$, —$SO_2N(R_{10})_2$, or $C_1$-$C_6$alkyl, wherein said $C_1$-$C_6$alkyl is optionally substituted by 1 hydoxy;
provided that at least one $R_{11}$ is —$NR_{10}SO_2R_{10}$, —$SOR_{10}$, —$SO_2R_{10}$, or —$SO_2N(R_{10})_2$,
each $R_{10}$ is independently $C_1$-$C_6$ alkyl; and
each $R_9$ is independently hydrogen or $C_1$-$C_6$haloalkyl; and
n is 0;
or a pharmaceutically acceptable salt thereof.

In another embodiment of the aforementioned embodiments is a compound of Formula IA wherein:
$L_1$ is a bond or $C_1$-$C_6$alkyl;
$R_1$ is —$OR_9$, —$C_1$-$C_6$alkyl, $C_2$-$C_6$alkenyl, $C_1$-$C_6$haloalkyl, or —C(=O)N($R_9$)$_2$;
$R_2$ is $C_1$-$C_6$alkyl, $C_3$-$C_8$cycloalkyl, or —$C_1$-$C_6$alkyl-$C_3$-$C_8$cycloalkyl; $R_3$ is hydrogen;
$R_4$ is phenyl substituted with one $R_{11}$, wherein $R_{11}$ is —$SO_2R_{10}$ and $R_{10}$ is $C_1$-$C_6$alkyl; or
$R_4$ is phenyl substituted with two $R_{11}$, wherein one $R_{11}$ is —$SO_2R_{10}$ and one $R_{11}$ is optionally substituted $C_1$-$C_6$alkyl;
each $R_9$ is independently hydrogen or $C_1$-$C_6$haloalkyl; and
n is 0;
or a pharmaceutically acceptable salt thereof.

In another embodiment of the aforementioned embodiments is a compound of Formula IA wherein:
-$L_1$-$R_1$ is —C(=$CH_2$)$CH_3$, isopropyl, —C(=O)NH$CH_2CF_3$, $CF_3$, or —C($CH_3$)$_2$OH;
$R_2$ is isobutyl, sec-butyl, cyclohexyl, —$CH_2$-cyclohexyl, or —$CH_2$-cyclopropyl;
$R_3$ is hydrogen;
$R_4$ is phenyl substituted with two $R_{11}$, wherein one $R_{11}$ is —$SO_2CH_3$ and one $R_{11}$ is —$CH_2OH$; or $R_4$ is phenyl substituted with one $R_{11}$, wherein $R_{11}$ is —$SO_2R_{10}$ and $R_{10}$ is $CH_3$; and
n is 0;
or a pharmaceutically acceptable salt thereof.

In some embodiments, the compound is selected from:

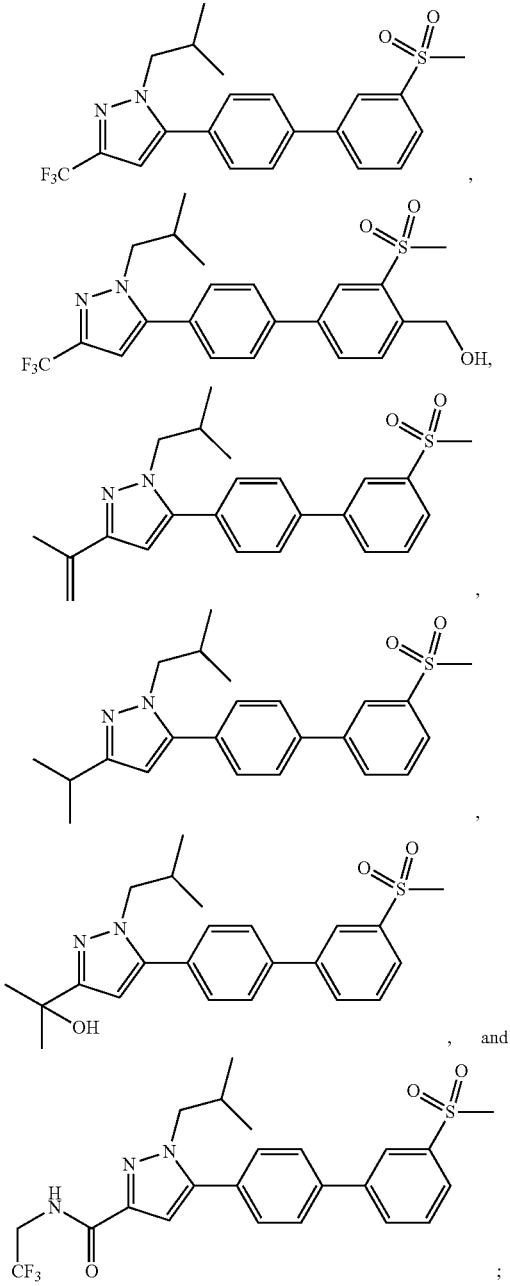

or a pharmaceutically acceptable salt thereof.

In some embodiments, the compound is selected from:

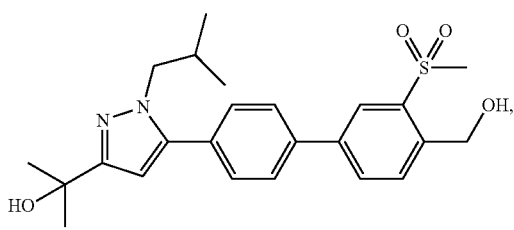

-continued

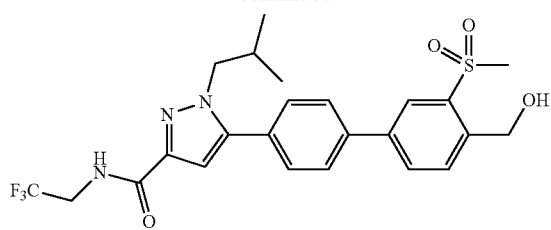

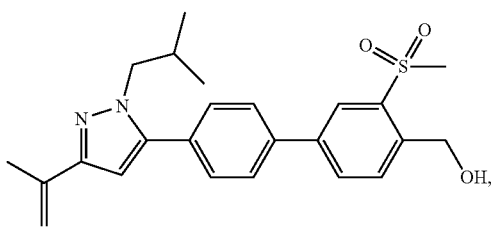

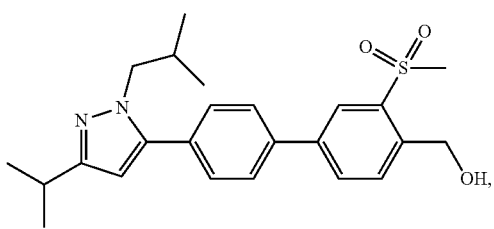

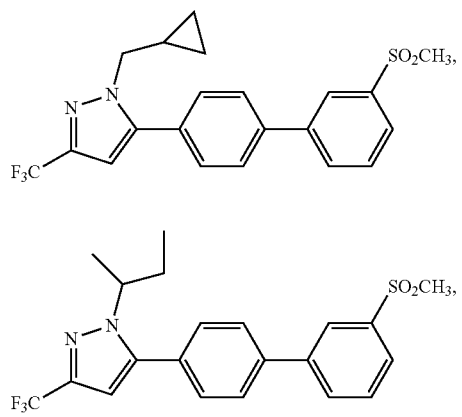

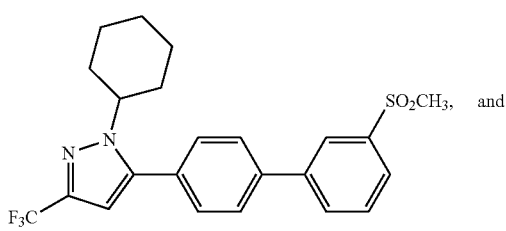

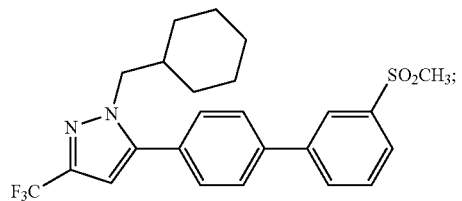

or a pharmaceutically acceptable salt thereof.

In another aspect is a compound of Formula (II):

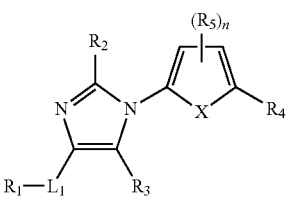

(II)

wherein:
X is —O—, —S—, or —C($R_6$)=C($R_6$)—;
$L_1$ is a bond, $C_1$-$C_6$alkyl, or $C_1$-$C_6$heteroalkyl;
$R_1$ is —O$R_9$, —N($R_9$)$_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$;
$R_2$ is $C_1$-$C_6$alkyl, $C_2$-$C_6$alkenyl, $C_3$-$C_8$cycloalkyl, or —$C_1$-$C_6$alkyl-$C_3$-$C_8$cycloalkyl;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_5$ is independently halogen, $C_1$-$C_6$alkyl, or $C_1$-$C_6$haloalkyl;
each $R_6$ is independently hydrogen, halogen, $C_1$-$C_6$alkyl, or $C_1$-$C_6$haloalkyl
$R_8$ is $C_1$-$C_6$alkyl, $C_2$-$C_6$alkenyl, $C_1$-$C_6$haloalkyl, —$C_1$-$C_6$alkyl-aryl, aryl, or heteroaryl;
each $R_9$ is independently hydrogen, $C_1$-$C_6$alkyl, $C_1$-$C_6$heteroalkyl, $C_1$-$C_6$haloalkyl, —$C_1$-$C_6$alkyl-aryl, aryl, or heteroaryl;
each $R_{10}$ is independently hydrogen, $C_1$-$C_6$alkyl, $C_1$-$C_6$heteroalkyl, —$C_1$-$C_6$alkyl-aryl, aryl, or heteroaryl;
each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and
n is 0-2;
or a pharmaceutically acceptable salt, pharmaceutically acceptable solvate, or pharmaceutically acceptable prodrug thereof.

In some embodiments is a compound of Formula II wherein X is —O—. In a further embodiment is a compound of Formula II wherein $R_4$ is heteroaryl substituted with at least one $R_{11}$. In some embodiments is a compound of Formula II wherein $R_4$ is aryl substituted with at least one $R_{11}$. In a further embodiment is a compound of Formula II wherein $R_4$ is phenyl substituted with at least one $R_{11}$. In a further embodiment is a compound of Formula II wherein $R_4$ is phenyl substituted with at least one $R_{11}$ and each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl. In a further embodiment is a compound of Formula II wherein $R_4$ is phenyl substituted with at least one $R_{11}$ and each $R_{11}$ is independently halogen, nitro, $—OR_{10}$, $—N(R_{10})_2$, $—CN$, $—C(=O)R_{10}$, $—C(=O)OR_{10}$, $—C(=O)N(R_{10})_2$, $—NR_{10}C(=O)R_{10}$, $NR_{10}SO_2R_{10}$, $—SOR_{10}$, $—SO_2R_{10}$, $—SO_2N(R_{10})_2$, optionally substituted $C_1$-$C_6$alkyl, optionally substituted $C_1$-$C_6$heteroalkyl, or optionally substituted $—C_1$-$C_6$alkyl-aryl. In a further embodiment is a compound of Formula II wherein $R_4$ is phenyl substituted with at least one $R_{11}$ and each $R_{11}$ is independently halogen, $—C(=O)R_{10}$, $—C(=O)N(R_{10})_2$, $—NR_{10}C(=O)R_{10}$, $NR_{10}SO_2R_{10}$, $—SOR_{10}$, $—SO_2R_{10}$, $—SO_2N(R_{10})_2$, or optionally substituted $C_1$-$C_6$alkyl. In a further embodiment is a compound of Formula II wherein $R_4$ is phenyl substituted with at least one $R_{11}$ and each $R_{11}$ is independently halogen, $—SO_2R_{10}$, or optionally substituted $C_1$-$C_6$alkyl. In a further embodiment is a compound of Formula II wherein $R_4$ is phenyl substituted with at least one $R_{11}$ and each $R_{11}$ is independently $—SO_2R_{10}$ or optionally substituted $C_1$-$C_6$alkyl. In a further embodiment is a compound of Formula II wherein $R_4$ is phenyl substituted with at least one $R_{11}$, each $R_{11}$ is independently $—SO_2R_{10}$ or optionally substituted $C_1$-$C_6$alkyl, and $R_{11}$ is $C_1$-$C_6$alkyl. In a further embodiment is a compound of Formula II wherein $R_4$ is phenyl substituted with at least one $R_{11}$, each $R_{11}$ is independently $—SO_2R_{10}$ or optionally substituted $C_1$-$C_6$alkyl, and $R_{11}$ is $CH_3$. In some embodiments is a compound of Formula II wherein $R_4$ is aryl substituted with one $R_{11}$. In some embodiments is a compound of Formula II wherein $R_4$ is aryl substituted with two $R_{11}$. In some embodiments is a compound of Formula II wherein $R_4$ is aryl substituted with three $R_{11}$. In further embodiments is a compound of Formula II wherein $R_4$ is phenyl substituted with one $R_{11}$. In further embodiments is a compound of Formula II wherein $R_4$ is phenyl substituted with two $R_{11}$. In further embodiments is a compound of Formula II wherein $R_4$ is phenyl substituted with three $R_{11}$. In some embodiments is a compound of Formula II wherein $R_4$ is heteroaryl substituted with one $R_{11}$. In some embodiments is a compound of Formula II wherein $R_4$ is heteroaryl substituted with two $R_{11}$. In some embodiments is a compound of Formula II wherein $R_4$ is heteroaryl substituted with three $R_{11}$.

In another embodiment is a compound of Formula II wherein X is $—O—$, $L_1$ is a bond and $R_1$ is $C_1$-$C_6$alkyl, $C_2$-$C_6$alkenyl, $C_1$-$C_6$haloalkyl, $C_2$-$C_9$heterocycloalkyl, $—C(=O)R_8$, or $—C(=O)N(R_9)_2$. In another embodiment is a compound of Formula II wherein X is $—O—$, $L_1$ is a bond and $R_1$ is $C_1$-$C_6$alkyl. In another embodiment is a compound of Formula II wherein X is $—O—$, $L_1$ is a bond and $R_1$ is $C_2$-$C_6$alkenyl. In another embodiment is a compound of Formula II wherein X is $—O—$, $L_1$ is a bond and $R_1$ is $C_1$-$C_6$haloalkyl. In another embodiment is a compound of Formula II wherein X is $—O—$, $L_1$ is a bond and $R_1$ is $C_2$-$C_9$heterocycloalkyl. In another embodiment is a compound of Formula II wherein X is $—O—$, $L_1$ is a bond and $R_1$ is $—C(=O)R_8$. In another embodiment is a compound of Formula II wherein X is $—O—$, $L_1$ is a bond, $R_1$ is $—C(=O)R_8$, and $R_8$ is $C_1$-$C_6$alkyl, $C_2$-$C_6$alkenyl, $C_1$-$C_6$haloalkyl, $—C_1$-$C_6$alkyl-aryl, aryl, or heteroaryl. In another embodiment is a compound of Formula II wherein X is $—O—$, $L_1$ is a bond and $R_1$ is $—C(=O)N(R_9)_2$.

In another embodiment is a compound of Formula II wherein X is $—O—$, $L_1$ is $C_1$-$C_6$alkyl and $R_1$ is $—OR_9$, $—N(R_9)_2$, $C_1$-$C_6$alkyl, $C_2$-$C_6$alkenyl, $C_1$-$C_6$haloalkyl, $C_2$-$C_9$heterocycloalkyl, $—C(=O)R_8$, or $—C(=O)N(R_9)_2$. In another embodiment is a compound of Formula II wherein X is $—O—$, $L_1$ is $C_1$-$C_6$alkyl and $R_1$ is $—OR_9$. In another embodiment is a compound of Formula II wherein X is $—O—$, $L_1$ is $C_1$-$C_6$alkyl and $R_1$ is $—OH$. In another embodiment is a compound of Formula II wherein X is $—O—$, $L_1$ is $C_1$-$C_6$alkyl and $R_1$ is $—N(R_9)_2$. In another embodiment is a compound of Formula II wherein X is $—O—$, $L_1$ is $C_1$-$C_6$alkyl and $R_1$ is $C_1$-$C_6$alkyl. In another embodiment is a compound of Formula II wherein X is $—O—$, $L_1$ is $C_1$-$C_6$alkyl and $R_1$ is $C_2$-$C_6$alkenyl. In another embodiment is a compound of Formula II wherein X is $—O—$, $L_1$ is $C_1$-$C_6$alkyl and $R_1$ is $C_1$-$C_6$haloalkyl. In another embodiment is a compound of Formula II wherein X is $—O—$, $L_1$ is $C_1$-$C_6$alkyl and $R_1$ is $C_2$-$C_9$heterocycloalkyl. In another embodiment is a compound of Formula II wherein X is $—O—$, $L_1$ is $C_1$-$C_6$alkyl and $R_1$ is $—C(=O)R_8$. In another embodiment is a compound of Formula II wherein X is $—O—$, $L_1$ is $C_1$-$C_6$alkyl, $R_1$ is $—C(=O)R_8$, and $R_8$ is $C_1$-$C_6$alkyl, $C_2$-$C_6$alkenyl, $C_1$-$C_6$haloalkyl, $—C_1$-$C_6$alkyl-aryl, aryl, or heteroaryl. In another embodiment is a compound of Formula II wherein X is $—O—$, $L_1$ is $C_1$-$C_6$alkyl and $R_1$ is $—C(=O)N(R_9)_2$.

In some embodiments is a compound of Formula II wherein $R_2$ is $C_1$-$C_6$alkyl. In another embodiment is a compound of Formula II wherein $R_2$ is $C_2$-$C_6$alkenyl. In another embodiment is a compound of Formula II wherein $R_2$ is $C_3$-$C_8$cycloalkyl. In another embodiment is a compound of Formula II wherein $R_2$ is $—C_1$-$C_6$alkyl-$C_3$-$C_8$cycloalkyl.

In another embodiment is a compound of Formula II wherein X is $—O—$, $L_1$ is a bond, $R_1$ is $C_1$-$C_6$alkyl, and $R_2$ is $C_1$-$C_6$alkyl. In another embodiment is a compound of Formula II wherein X is $—O—$, $L_1$ is a bond, $R_1$ is $C_1$-$C_6$alkyl, and $R_2$ is $C_2$-$C_6$alkenyl. In another embodiment is a compound of Formula II wherein X is $—O—$, $L_1$ is a bond, $R_1$ is $C_1$-$C_6$alkyl, and $R_2$ is $C_3$-$C_8$cycloalkyl. In another embodiment is a compound of Formula II wherein X is $—O—$, $L_1$ is a bond, $R_1$ is $C_1$-$C_6$alkyl, and $R_2$ is $—C_1$-$C_6$alkyl-$C_3$-$C_8$cycloalkyl. In another embodiment is a compound of Formula II wherein X is $—O—$, $L_1$ is a bond, $R_1$ is $C_2$-$C_6$alkenyl, and $R_2$ is $C_1$-$C_6$alkyl. In another embodiment is a compound of Formula II wherein X is $—O—$, $L_1$ is a bond, $R_1$ is $C_2$-$C_6$alkenyl, and $R_2$ is $C_2$-$C_6$alkenyl. In another embodiment is a compound of Formula II wherein X is $—O—$, $L_1$ is a bond, $R_1$ is $C_2$-$C_6$alkenyl, and $R_2$ is $C_3$-$C_8$cycloalkyl. In another embodiment is a compound of Formula II wherein X is $—O—$, $L_1$ is a bond, $R_1$ is $C_2$-$C_6$alkenyl, and $R_2$ is $—C_1$-$C_6$alkyl-$C_3$-$C_8$cycloalkyl. In another embodiment is a compound of Formula II wherein X is $—O—$, $L_1$ is a bond, $R_1$ is $C_1$-$C_6$haloalkyl, and $R_2$ is $C_1$-$C_6$alkyl. In another embodiment is a compound of Formula II wherein X is $—O—$, $L_1$ is a bond, $R_1$ is $C_1$-$C_6$haloalkyl, and $R_2$ is $C_2$-$C_6$alkenyl. In another embodiment is a compound of Formula II wherein X is $—O—$, $L_1$ is a bond, $R_1$ is $C_1$-$C_6$haloalkyl, and $R_2$ is $C_3$-$C_8$cycloalkyl. In another embodiment is a compound of Formula II wherein X is $—O—$, $L_1$ is a bond, $R_1$ is $C_1$-$C_6$haloalkyl, and $R_2$ is $—C_1$-$C_6$alkyl-$C_3$-$C_8$cycloalkyl. In another embodiment is a compound of Formula II wherein X is $—O—$, $L_1$ is a bond, $R_1$ is $C_2$-$C_9$heterocycloalkyl, and $R_2$ is $C_1$-$C_6$alkyl. In another embodiment is a compound of Formula II wherein X is $—O—$, $L_1$ is a bond, $R_1$ is $C_2$-$C_9$heterocycloalkyl, and $R_2$ is $C_2$-$C_6$alkenyl. In another embodiment is a compound of Formula II wherein X is $—O—$, $L_1$ is a bond, $R_1$ is $C_2$-$C_9$heterocycloalkyl, and $R_2$ is $C_3$-$C_8$cycloalkyl. In another embodiment is a compound of Formula II wherein X is $—O—$, $L_1$ is a bond, $R_1$ is $C_2$-$C_9$heterocycloalkyl, and $R_2$ is $—C_1$-$C_6$alkyl-$C_3$-$C_8$cycloalkyl. In another embodiment is a compound of Formula II wherein X is $—O—$, $L_1$ is a $C_1$-$C_6$alkyl, $R_1$ is —$OR_9$, $R_9$ is hydrogen, and $R_2$ is $C_1$-$C_6$alkyl. In another embodiment is a compound of Formula II wherein X is —O—, $L_1$ is a $C_1$-$C_6$alkyl, $R_1$ is —$OR_9$, $R_9$ is hydrogen, and $R_2$ is $C_2$-$C_6$alkenyl. In another embodiment is a compound of Formula II wherein X is —O—, $L_1$ is a $C_1$-$C_6$alkyl, $R_1$ is —$OR_9$, $R_9$ is hydrogen, and $R_2$ is $C_3$-$C_8$cycloalkyl. In another embodiment is a compound of Formula II wherein X is —O—, $L_1$ is a $C_1$-$C_6$alkyl, $R_1$ is —$OR_9$, $R_9$ is hydrogen, and $R_2$ is —$C_1$-$C_6$alkyl-$C_3$-$C_8$cycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$. In a further embodiment of the aforementioned embodiments is a compound of Formula II wherein $R_4$ is phenyl substituted with two $R_{11}$. In a further embodiment of the aforementioned embodiments is a compound of Formula II wherein $R_4$ is phenyl substituted with two $R_{11}$, and one $R_{11}$ is —$SO_2R_{10}$ and one $R_{11}$ is optionally substituted $C_1$-$C_6$alkyl. In yet a further embodiment of the aforementioned embodiments is a compound of Formula II wherein $R_4$ is phenyl substituted with two $R_{11}$, and one $R_{11}$ is —$SO_2CH_3$ and one $R_{11}$ is —$CH_2OH$.

In another embodiment of the aforementioned embodiments is a compound of Formula II wherein $R_3$ is hydrogen, halogen, $C_1$-$C_6$alkyl, or $C_1$-$C_6$haloalkyl. In some embodiments of the aforementioned embodiments is a compound of Formula II wherein $R_3$ is hydrogen. In some embodiments of the aforementioned embodiments is a compound of Formula I wherein $R_3$ is halogen. In some embodiments of the aforementioned embodiments is a compound of Formula II wherein $R_3$ is $C_1$-$C_6$alkyl. In some embodiments of the aforementioned embodiments is a compound of Formula II wherein $R_3$ is $C_1$-$C_6$haloalkyl.

In some embodiments is a compound of Formula II wherein X is —S—. In a further embodiment is a compound of Formula II wherein $R_4$ is heteroaryl substituted with at least one $R_{11}$. In some embodiments is a compound of Formula II wherein $R_4$ is aryl substituted with at least one $R_{11}$. In a further embodiment is a compound of Formula II wherein $R_4$ is phenyl substituted with at least one $R_{11}$. In a further embodiment is a compound of Formula II wherein $R_4$ is phenyl substituted with at least one $R_{11}$ and each $R_{11}$ is independently halogen, nitro, —$OR_{10}$, —$N(R_{10})_2$, —CN, —C(=O)$R_{10}$, —C(=O)O$R_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl. In a further embodiment is a compound of Formula II wherein $R_4$ is phenyl substituted with at least one $R_{11}$ and each $R_{11}$ is independently halogen, nitro, —$OR_{10}$, —$N(R_{10})_2$, —CN, —C(=O)$R_{10}$, —C(=O)O$R_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, optionally substituted $C_1$-$C_6$alkyl, optionally substituted $C_1$-$C_6$heteroalkyl, or optionally substituted —$C_1$-$C_6$alkyl-aryl. In a further embodiment is a compound of Formula II wherein $R_4$ is phenyl substituted with at least one $R_{11}$ and each $R_{11}$ is independently halogen, —C(=O)$R_{10}$, —C(=O)$_N$($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, or optionally substituted $C_1$-$C_6$alkyl. In a further embodiment is a compound of Formula II wherein $R_4$ is phenyl substituted with at least one $R_{11}$ and each $R_{11}$ is independently halogen, —$SO_2R_{10}$, or optionally substituted $C_1$-$C_6$alkyl. In a further embodiment is a compound of Formula II wherein $R_4$ is phenyl substituted with at least one $R_{11}$ and each $R_{11}$ is independently —$SO_2R_{10}$ or optionally substituted $C_1$-$C_6$alkyl. In a further embodiment is a compound of Formula II wherein $R_4$ is phenyl substituted with at least one $R_{11}$, each $R_{11}$ is independently —$SO_2R_{10}$ or optionally substituted $C_1$-$C_6$alkyl, and $R_{10}$ is $C_1$-$C_6$alkyl. In a further embodiment is a compound of Formula II wherein $R_4$ is phenyl substituted with at least one $R_{11}$, each $R_{11}$ is independently —$SO_2R_{10}$ or optionally substituted $C_1$-$C_6$alkyl, and $R_{11}$ is $CH_3$. In some embodiments is a compound of Formula II wherein $R_4$ is aryl substituted with one $R_{11}$. In some embodiments is a compound of Formula II wherein $R_4$ is aryl substituted with two $R_{11}$. In some embodiments is a compound of Formula II wherein $R_4$ is aryl substituted with three $R_{11}$. In further embodiments is a compound of Formula II wherein $R_4$ is phenyl substituted with one $R_{11}$. In further embodiments is a compound of Formula II wherein $R_4$ is phenyl substituted with two $R_{11}$. In further embodiments is a compound of Formula II wherein $R_4$ is phenyl substituted with three $R_{11}$. In some embodiments is a compound of Formula II wherein $R_4$ is heteroaryl substituted with one $R_{11}$. In some embodiments is a compound of Formula II wherein $R_4$ is heteroaryl substituted with two $R_{11}$. In some embodiments is a compound of Formula II wherein $R_4$ is heteroaryl substituted with three $R_{11}$.

In another embodiment is a compound of Formula II wherein X is —S—, $L_1$ is a bond and $R_1$ is $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$. In another embodiment is a compound of Formula II wherein X is —S—, $L_1$ is a bond and $R_1$ is $C_1$-$C_6$alkyl. In another embodiment is a compound of Formula II wherein X is —S—, $L_1$ is a bond and $R_1$ is $C_2$-$C_6$alkenyl. In another embodiment is a compound of Formula II wherein X is —S—, $L_1$ is a bond and $R_1$ is $C_1$-$C_6$haloalkyl. In another embodiment is a compound of Formula II wherein X is —S—, $L_1$ is a bond and $R_1$ is $C_2$-$C_9$heterocycloalkyl. In another embodiment is a compound of Formula II wherein X is —S—, $L_1$ is a bond and $R_1$ is —C(=O)$R_8$. In another embodiment is a compound of Formula II wherein X is —S—, $L_1$ is a bond, $R_1$ is —C(=O)$R_8$, and $R_8$ is $C_1$-$C_6$alkyl, $C_2$-$C_6$alkenyl, $C_1$-$C_6$haloalkyl, —$C_1$-$C_6$alkyl-aryl, aryl, or heteroaryl. In another embodiment is a compound of Formula II wherein X is —S—, $L_1$ is a bond and $R_1$ is —C(=O)N($R_9$)$_2$.

In another embodiment is a compound of Formula II wherein X is —S—, $L_1$ is $C_1$-$C_6$alkyl and $R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)N($R_9$)$_2$. In another embodiment is a compound of Formula II wherein X is —S—, $L_1$ is $C_1$-$C_6$alkyl and $R_1$ is —$OR_9$. In another embodiment is a compound of Formula II wherein X is —S—, $L_1$ is $C_1$-$C_6$alkyl and $R_1$ is —OH. In another embodiment is a compound of Formula II wherein X is —S—, $L_1$ is $C_1$-$C_6$alkyl and $R_1$ is —$N(R_9)_2$. In another embodiment is a compound of Formula II wherein X is —S—, $L_1$ is $C_1$-$C_6$alkyl and $R_1$ is $C_1$-$C_6$alkyl. In another embodiment is a compound of Formula II wherein X is —S—, $L_1$ is $C_1$-$C_6$alkyl and $R_1$ is $C_2$-$C_6$alkenyl. In another embodiment is a compound of Formula II wherein X is —S—, $L_1$ is $C_1$-$C_6$alkyl and $R_1$ is $C_1$-$C_6$haloalkyl. In another embodiment is a compound of Formula II wherein X is —S—, $L_1$ is $C_1$-$C_6$alkyl and $R_1$ is $C_2$-$C_9$heterocycloalkyl. In another embodiment is a compound of Formula II wherein X is —S—, $L_1$ is $C_1$-$C_6$alkyl and $R_1$ is —C(=O)$R_8$. In another embodiment is a compound of Formula II wherein X is —S—, $L_1$ is $C_1$-$C_6$alkyl, $R_1$ is —C(=O)$R_8$, and $R_8$ is $C_1$-$C_6$alkyl, $C_2$-$C_6$alkenyl, $C_1$-$C_6$haloalkyl, —$C_1$-$C_6$alkyl-aryl, aryl, or heteroaryl. In another embodiment is a compound of Formula II wherein X is —S—, $L_1$ is $C_1$-$C_6$alkyl and $R_1$ is —C(=O)N($R_9$)$_2$.

In some embodiments is a compound of Formula II wherein $R_2$ is $C_1$-$C_6$alkyl. In another embodiment is a compound of Formula II wherein $R_2$ is $C_1$-$C_6$alkyl. In another embodiment is a compound of Formula II wherein $R_2$ is $C_2$-$C_6$alkenyl. In another embodiment is a compound of Formula II wherein $R_2$ is $C_3$-$C_8$cycloalkyl. In another embodiment is a compound of Formula II wherein $R_2$ is —$C_1$-$C_6$alkyl-$C_3$-$C_8$cycloalkyl.

In another embodiment is a compound of Formula II wherein X is —S—, $L_1$ is a bond, $R_1$ is $C_1$-$C_6$alkyl, and $R_2$ is $C_1$-$C_6$alkyl. In another embodiment is a compound of Formula II wherein X is —S—, $L_1$ is a bond, $R_1$ is $C_1$-$C_6$alkyl, and $R_2$ is $C_2$-$C_6$alkenyl. In another embodiment is a compound of Formula II wherein X is —S—, $L_1$ is a bond, $R_1$ is $C_1$-$C_6$alkyl, and $R_2$ is $C_3$-$C_8$cycloalkyl. In another embodiment is a compound of Formula II wherein X is —S—, $L_1$ is a bond, $R_1$ is $C_1$-$C_6$alkyl, and $R_2$ is —$C_1$-$C_6$alkyl-$C_3$-$C_8$cycloalkyl. In another embodiment is a compound of Formula II wherein X is —S—, $L_1$ is a bond, $R_1$ is $C_2$-$C_6$alkenyl, and $R_2$ is $C_1$-$C_6$alkyl. In another embodiment is a compound of Formula II wherein X is —S—, $L_1$ is a bond, $R_1$ is $C_2$-$C_6$alkenyl, and $R_2$ is $C_2$-$C_6$alkenyl. In another embodiment is a compound of Formula II wherein X is —S—, $L_1$ is a bond, $R_1$ is $C_2$-$C_6$alkenyl, and $R_2$ is $C_3$-$C_8$cycloalkyl. In another embodiment is a compound of Formula II wherein X is —S—, $L_1$ is a bond, $R_1$ is $C_2$-$C_6$alkenyl, and $R_2$ is —$C_1$-$C_6$alkyl-$C_3$-$C_8$cycloalkyl. In another embodiment is a compound of Formula II wherein X is —S—, $L_1$ is a bond, $R_1$ is $C_1$-$C_6$haloalkyl, and $R_2$ is $C_1$-$C_6$alkyl. In another embodiment is a compound of Formula II wherein X is —S—, $L_1$ is a bond, $R_1$ is $C_1$-$C_6$haloalkyl, and $R_2$ is $C_2$-$C_6$alkenyl. In another embodiment is a compound of Formula II wherein X is —S—, $L_1$ is a bond, $R_1$ is $C_1$-$C_6$haloalkyl, and $R_2$ is $C_3$-$C_8$cycloalkyl. In another embodiment is a compound of Formula II wherein X is —S—, $L_1$ is a bond, $R_1$ is $C_1$-$C_6$haloalkyl, and $R_2$ is —$C_1$-$C_6$alkyl-$C_3$-$C_8$cycloalkyl. In another embodiment is a compound of Formula II wherein X is —S—, $L_1$ is a bond, $R_1$ is $C_2$-$C_9$heterocycloalkyl, and $R_2$ is $C_1$-$C_6$alkyl. In another embodiment is a compound of Formula II wherein X is —S—, $L_1$ is a bond, $R_1$ is $C_2$-$C_9$heterocycloalkyl, and $R_2$ is $C_2$-$C_6$alkenyl. In another embodiment is a compound of Formula II wherein X is —S—, $L_1$ is a bond, $R_1$ is $C_2$-$C_9$heterocycloalkyl, and $R_2$ is $C_3$-$C_8$cycloalkyl. In another embodiment is a compound of Formula II wherein X is —S—, $L_1$ is a bond, $R_1$ is $C_2$-$C_9$heterocycloalkyl, and $R_2$ is —$C_1$-$C_6$alkyl-$C_3$-$C_8$cycloalkyl. In another embodiment is a compound of Formula II wherein X is —S—, $L_1$ is a $C_1$-$C_6$alkyl, $R_1$ is —O$R_9$, $R_9$ is hydrogen, and $R_2$ is $C_1$-$C_6$alkyl. In another embodiment is a compound of Formula II wherein X is —S—, $L_1$ is a $C_1$-$C_6$alkyl, $R_1$ is —O$R_9$, $R_9$ is hydrogen, and $R_2$ is $C_2$-$C_6$alkenyl. In another embodiment is a compound of Formula II wherein X is —S—, $L_1$ is a $C_1$-$C_6$alkyl, $R_1$ is —O$R_9$, $R_9$ is hydrogen, and $R_2$ is $C_3$-$C_8$cycloalkyl. In another embodiment is a compound of Formula II wherein X is —S—, $L_1$ is a $C_1$-$C_6$alkyl, $R_1$ is —O$R_9$, $R_9$ is hydrogen, and $R_2$ is —$C_1$-$C_6$alkyl-$C_3$-$C_8$cycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —SO$_2$$R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —SO$_2$$R_{10}$ and $R_{10}$ is CH$_3$. In a further embodiment of the aforementioned embodiments is a compound of Formula II wherein $R_4$ is phenyl substituted with two $R_{11}$. In a further embodiment of the aforementioned embodiments is a compound of Formula II wherein $R_4$ is phenyl substituted with two $R_{11}$, and one $R_{11}$ is —SO$_2$$R_{10}$ and one $R_{11}$ is optionally substituted $C_1$-$C_6$alkyl. In yet a further embodiment of the aforementioned embodiments is a compound of Formula II wherein $R_4$ is phenyl substituted with two $R_{11}$, and one $R_{11}$ is —SO$_2$CH$_3$ and one $R_{11}$ is —CH$_2$OH.

In another embodiment of the aforementioned embodiments is a compound of Formula II wherein $R_3$ is hydrogen, halogen, $C_1$-$C_6$alkyl, or $C_1$-$C_6$haloalkyl. In some embodiments of the aforementioned embodiments is a compound of Formula II wherein $R_3$ is hydrogen. In some embodiments of the aforementioned embodiments is a compound of Formula I wherein $R_3$ is halogen. In some embodiments of the aforementioned embodiments is a compound of Formula II wherein $R_3$ is $C_1$-$C_6$alkyl. In some embodiments of the aforementioned embodiments is a compound of Formula II wherein $R_3$ is $C_1$-$C_6$haloalkyl.

In some embodiments is a compound of Formula II wherein X is —CH=CH—. In a further embodiment is a compound of Formula II wherein $R_4$ is heteroaryl substituted with at least one $R_{11}$. In some embodiments is a compound of Formula II wherein $R_4$ is aryl substituted with at least one $R_{11}$. In a further embodiment is a compound of Formula II wherein $R_4$ is phenyl substituted with at least one $R_{11}$. In a further embodiment is a compound of Formula II wherein $R_4$ is phenyl substituted with at least one $R_{11}$ and each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl. In a further embodiment is a compound of Formula II wherein $R_4$ is phenyl substituted with at least one $R_{11}$ and each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, N$R_{10}$SO$_2$$R_{10}$, —SO$R_{10}$, —SO$_2$$R_{10}$, —SO$_2$N($R_{10}$)$_2$, optionally substituted $C_1$-$C_6$alkyl, optionally substituted $C_1$-$C_6$heteroalkyl, or optionally substituted —$C_1$-$C_6$alkyl-aryl. In a further embodiment is a compound of Formula II wherein $R_4$ is phenyl substituted with at least one $R_{11}$ and each $R_{11}$ is independently halogen, —C(=O)$R_{10}$, —C(=O)N($R_{10}$)$_2$, —N$R_{10}$C(=O)$R_{10}$, N$R_{10}$SO$_2$$R_{10}$, —SO$R_{10}$, —SO$_2$$R_{10}$, —SO$_2$N($R_{10}$)$_2$, or optionally substituted $C_1$-$C_6$alkyl. In a further embodiment is a compound of Formula II wherein $R_4$ is phenyl substituted with at least one $R_{11}$ and each $R_{11}$ is independently halogen, —SO$_2$$R_{10}$, or optionally substituted $C_1$-$C_6$alkyl. In a further embodiment is a compound of Formula II wherein $R_4$ is phenyl substituted with at least one $R_{11}$ and each $R_{11}$ is independently —SO$_2$$R_{10}$ or optionally substituted $C_1$-$C_6$alkyl. In a further embodiment is a compound of Formula II wherein $R_4$ is phenyl substituted with at least one $R_{11}$, each $R_{11}$ is independently —$SO_2R_{10}$ or optionally substituted $C_1$-$C_6$alkyl, and $R_{11}$ is $C_1$-$C_6$alkyl. In a further embodiment is a compound of Formula II wherein $R_4$ is phenyl substituted with at least one $R_{11}$, each $R_{11}$ is independently —$SO_2R_{10}$ or optionally substituted $C_1$-$C_6$alkyl, and $R_{11}$ is $CH_3$. In some embodiments is a compound of Formula II wherein $R_4$ is aryl substituted with one $R_{11}$. In some embodiments is a compound of Formula II wherein $R_4$ is aryl substituted with two $R_{11}$. In some embodiments is a compound of Formula II wherein $R_4$ is aryl substituted with three $R_{11}$. In further embodiments is a compound of Formula II wherein $R_4$ is phenyl substituted with one $R_{11}$. In further embodiments is a compound of Formula II wherein $R_4$ is phenyl substituted with two $R_{11}$. In further embodiments is a compound of Formula II wherein $R_4$ is phenyl substituted with three $R_{11}$. In some embodiments is a compound of Formula II wherein $R_4$ is heteroaryl substituted with one $R_{11}$. In some embodiments is a compound of Formula II wherein $R_4$ is heteroaryl substituted with two $R_{11}$. In some embodiments is a compound of Formula II wherein $R_4$ is heteroaryl substituted with three $R_{11}$.

In another embodiment is a compound of Formula II wherein X is —CH═CH—, $L_1$ is a bond and $R_1$ is $C_1$-$C_6$alkyl, $C_2$-$C_6$alkenyl, $C_1$-$C_6$haloalkyl, $C_2$-$C_9$heterocycloalkyl, —C(═O)$R_8$, or —C(═O)N($R_9$)$_2$. In another embodiment is a compound of Formula II wherein X is —CH═CH—, $L_1$ is a bond and $R_1$ is $C_1$-$C_6$alkyl. In another embodiment is a compound of Formula II wherein X is —CH═CH—, $L_1$ is a bond and $R_1$ is $C_2$-$C_6$alkenyl. In another embodiment is a compound of Formula II wherein X is —CH═CH—, $L_1$ is a bond and $R_1$ is $C_1$-$C_6$haloalkyl. In another embodiment is a compound of Formula II wherein X is —CH═CH—, $L_1$ is a bond and $R_1$ is $C_2$-$C_9$heterocycloalkyl. In another embodiment is a compound of Formula II wherein X is —CH═CH—, $L_1$ is a bond and $R_1$ is —C(═O)$R_8$. In another embodiment is a compound of Formula II wherein X is —CH═CH—, $L_1$ is a bond, $R_1$ is —C(═O)$R_8$, and $R_8$ is $C_1$-$C_6$alkyl, $C_2$-$C_6$alkenyl, $C_1$-$C_6$haloalkyl, —$C_1$-$C_6$alkyl-aryl, aryl, or heteroaryl. In another embodiment is a compound of Formula II wherein X is —CH═CH—, $L_1$ is a bond and $R_1$ is —C(═O)N($R_9$)$_2$.

In another embodiment is a compound of Formula II wherein X is —CH═CH—, $L_1$ is $C_1$-$C_6$alkyl and $R_1$ is —O$R_9$, —N($R_9$)$_2$, $C_1$-$C_6$alkyl, $C_2$-$C_6$alkenyl, $C_1$-$C_6$haloalkyl, $C_2$-$C_9$heterocycloalkyl, —C(═O)$R_8$, or —C(═O)N($R_9$)$_2$. In another embodiment is a compound of Formula II wherein X is —CH═CH—, $L_1$ is $C_1$-$C_6$alkyl and $R_1$ is —O$R_9$. In another embodiment is a compound of Formula II wherein X is —CH═CH—, $L_1$ is $C_1$-$C_6$alkyl and $R_1$ is —OH. In another embodiment is a compound of Formula II wherein X is —CH═CH—, $L_1$ is $C_1$-$C_6$alkyl and $R_1$ is —N($R_9$)$_2$. In another embodiment is a compound of Formula II wherein X is —CH═CH—, $L_1$ is $C_1$-$C_6$alkyl and $R_1$ is $C_1$-$C_6$alkyl. In another embodiment is a compound of Formula II wherein X is —CH═CH—, $L_1$ is $C_1$-$C_6$alkyl and $R_1$ is $C_2$-$C_6$alkenyl. In another embodiment is a compound of Formula II wherein X is —CH═CH—, $L_1$ is $C_1$-$C_6$alkyl and $R_1$ is $C_1$-$C_6$haloalkyl. In another embodiment is a compound of Formula II wherein X is —CH═CH—, $L_1$ is $C_1$-$C_6$alkyl and $R_1$ is $C_2$-$C_9$heterocycloalkyl. In another embodiment is a compound of Formula II wherein X is —CH═CH—, $L_1$ is $C_1$-$C_6$alkyl and $R_1$ is —C(═O)$R_8$. In another embodiment is a compound of Formula II wherein X is —CH═CH—, $L_1$ is $C_1$-$C_6$alkyl, $R_1$ is —C(═O)$R_8$, and $R_8$ is $C_1$-$C_6$alkyl, $C_1$-$C_6$alkenyl, $C_1$-$C_6$haloalkyl, —$C_1$-$C_6$alkyl-aryl, aryl, or heteroaryl. In another embodiment is a compound of Formula II wherein X is —CH═CH—, $L_1$ is $C_1$-$C_6$alkyl and $R_1$ is —C(═O)N($R_9$)$_2$.

In some embodiments is a compound of Formula II wherein $R_2$ is $C_1$-$C_6$alkyl. In another embodiment is a compound of Formula II wherein $R_2$ is $C_1$-$C_6$alkyl. In another embodiment is a compound of Formula II wherein $R_2$ is $C_2$-$C_6$alkenyl. In another embodiment is a compound of Formula II wherein $R_2$ is $C_3$-$C_8$cycloalkyl. In another embodiment is a compound of Formula II wherein $R_2$ is —$C_1$-$C_6$alkyl-$C_3$-$C_8$cycloalkyl.

In another embodiment is a compound of Formula II wherein X is —CH═CH—, $L_1$ is a bond, $R_1$ is $C_1$-$C_6$alkyl, and $R_2$ is $C_1$-$C_6$alkyl. In another embodiment is a compound of Formula II wherein X is —CH═CH—, $L_1$ is a bond, $R_1$ is $C_1$-$C_6$alkyl, and $R_2$ is $C_2$-$C_6$alkenyl. In another embodiment is a compound of Formula II wherein X is —CH═CH—, $L_1$ is a bond, $R_1$ is $C_1$-$C_6$alkyl, and $R_2$ is $C_3$-$C_8$cycloalkyl. In another embodiment is a compound of Formula II wherein X is —CH═CH—, $L_1$ is a bond, $R_1$ is $C_1$-$C_6$alkyl, and $R_2$ is —$C_1$-$C_6$alkyl-$C_3$-$C_8$cycloalkyl. In another embodiment is a compound of Formula II wherein X is —CH═CH—, $L_1$ is a bond, $R_1$ is $C_2$-$C_6$alkenyl, and $R_2$ is $C_1$-$C_6$alkyl. In another embodiment is a compound of Formula II wherein X is —CH═CH—, $L_1$ is a bond, $R_1$ is $C_2$-$C_6$alkenyl, and $R_2$ is $C_2$-$C_6$alkenyl. In another embodiment is a compound of Formula II wherein X is —CH═CH—, $L_1$ is a bond, $R_1$ is $C_2$-$C_6$alkenyl, and $R_2$ is $C_3$-$C_8$cycloalkyl. In another embodiment is a compound of Formula II wherein X is —CH═CH—, $L_1$ is a bond, $R_1$ is $C_2$-$C_6$alkenyl, and $R_2$ is —$C_1$-$C_6$alkyl-$C_3$-$C_8$cycloalkyl. In another embodiment is a compound of Formula II wherein X is —CH═CH—, $L_1$ is a bond, $R_1$ is $C_1$-$C_6$haloalkyl, and $R_2$ is $C_1$-$C_6$alkyl. In another embodiment is a compound of Formula II wherein X is —CH═CH—, $L_1$ is a bond, $R_1$ is $C_1$-$C_6$haloalkyl, and $R_2$ is $C_2$-$C_6$alkenyl. In another embodiment is a compound of Formula II wherein X is —CH═CH—, $L_1$ is a bond, $R_1$ is $C_1$-$C_6$haloalkyl, and $R_2$ is $C_3$-$C_8$cycloalkyl. In another embodiment is a compound of Formula II wherein X is —CH═CH—, $L_1$ is a bond, $R_1$ is $C_1$-$C_6$haloalkyl, and $R_2$ is —$C_1$-$C_6$alkyl-$C_3$-$C_8$cycloalkyl. In another embodiment is a compound of Formula II wherein X is —CH═CH—, $L_1$ is a bond, $R_1$ is $C_2$-$C_9$heterocycloalkyl, and $R_2$ is $C_1$-$C_6$alkyl. In another embodiment is a compound of Formula II wherein X is —CH═CH—, $L_1$ is a bond, $R_1$ is $C_2$-$C_9$heterocycloalkyl, and $R_2$ is $C_2$-$C_6$alkenyl. In another embodiment is a compound of Formula II wherein X is —CH═CH—, $L_1$ is a bond, $R_1$ is $C_2$-$C_9$heterocycloalkyl, and $R_2$ is $C_3$-$C_8$cycloalkyl. In another embodiment is a compound of Formula II wherein X is —CH═CH—, $L_1$ is a bond, $R_1$ is $C_2$-$C_9$heterocycloalkyl, and $R_2$ is —$C_1$-$C_6$alkyl-$C_3$-$C_8$cycloalkyl. In another embodiment is a compound of Formula II wherein X is —CH═CH—, $L_1$ is a $C_1$-$C_6$alkyl, $R_1$ is —O$R_9$, $R_9$ is hydrogen, and $R_2$ is $C_1$-$C_6$alkyl. In another embodiment is a compound of Formula II wherein X is —CH═CH—, $L_1$ is a $C_1$-$C_6$alkyl, $R_1$ is —O$R_9$, $R_9$ is hydrogen, and $R_2$ is $C_2$-$C_6$alkenyl. In another embodiment is a compound of Formula II wherein X is —CH═CH—, $L_2$ is a $C_1$-$C_6$alkyl, $R_1$ is —O$R_9$, $R_9$ is hydrogen, and $R_2$ is $C_3$-$C_8$cycloalkyl. In another embodiment is a compound of Formula II wherein X is —CH═CH—, $L_1$ is a $C_1$-$C_6$alkyl, $R_1$ is —O$R_9$, $R_9$ is hydrogen, and $R_2$ is —$C_1$-$C_6$alkyl-$C_3$-$C_8$cycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$. In a further embodiment of the aforementioned embodiments is a compound of Formula II wherein $R_4$ is phenyl substituted with two $R_{11}$. In a further embodiment of the aforementioned embodiments is a compound of Formula II wherein $R_4$ is phenyl substituted with two $R_{11}$, and one $R_{11}$ is —$SO_2R_{10}$ and one $R_{11}$ is optionally substituted $C_1$-$C_6$alkyl. In yet a further embodiment of the aforementioned embodiments is a compound of Formula II wherein $R_4$ is phenyl substituted with two $R_{11}$, and one $R_{11}$ is —$SO_2CH_3$ and one $R_{11}$ is —$CH_2OH$.

In another embodiment of the aforementioned embodiments is a compound of Formula II wherein $R_3$ is hydrogen, halogen, $C_1$-$C_6$alkyl, or $C_1$-$C_6$haloalkyl. In some embodiments of the aforementioned embodiments is a compound of Formula II wherein $R_3$ is hydrogen. In some embodiments of the aforementioned embodiments is a compound of Formula II wherein $R_3$ is halogen. In some embodiments of the aforementioned embodiments is a compound of Formula II wherein $R_3$ is $C_1$-$C_6$alkyl. In some embodiments of the aforementioned embodiments is a compound of Formula II wherein $R_3$ is $C_1$-$C_6$haloalkyl.

In another embodiment is a compound of Formula II wherein X is —CH=CH—; and -$L_1$-$R_1$ is $C_1$-$C_6$alkyl, $C_1$-$C_6$alkyl-OH, or $C_1$-$C_6$haloalkyl. In another embodiment is a compound of Formula II wherein X is —CH=CH—; and -$L_1$-$R_1$ is —$CF_3$ or —$C(CH_3)_2OH$. In another embodiment is a compound of Formula II wherein X is —CH=CH—; and $R_2$ is $C_1$-$C_6$ alkyl. In another embodiment is a compound of Formula II wherein X is —CH=CH—; and $R_2$ is isobutyl. In another embodiment is a compound of Formula II wherein X is —CH=CH—; and $R_3$ is hydrogen. In another embodiment is a compound of Formula II wherein X is —CH=CH—; and $R_4$ is phenyl; wherein said phenyl is substituted with at least one $R_{11}$. In another embodiment is a compound of Formula II wherein X is —CH=CH—; and at least one $R_{11}$ is —$NR_{10}SO_2R_{10}$, —$SOR_{10}$, —$SO_2R_{10}$, or —$SO_2N(R_{10})_2$. In another embodiment is a compound of Formula II wherein X is —CH=CH—; and at least one $R_{11}$ is —$SO_2R_{10}$. In another embodiment is a compound of Formula II wherein X is —CH=CH—; and each $R_{10}$ is independently $C_1$-$C_6$ alkyl. In another embodiment is a compound of Formula II wherein X is —CH=CH—; and each $R_{10}$ is methyl. In another embodiment is a compound of Formula II wherein X is —CH=CH—; and $R_4$ is phenyl substituted with one $R_{11}$, wherein $R_{11}$ is —$SO_2R_{10}$ and $R_{10}$ is $C_1$-$C_6$alkyl; or $R_4$ is phenyl substituted with two $R_{11}$, and one $R_{11}$ is —$SO_2R_{10}$ and one $R_{11}$ is optionally substituted $C_1$-$C_6$alkyl. In another embodiment is a compound of Formula II wherein X is —CH=CH—; and $R_4$ is phenyl substituted with two $R_{11}$, wherein one $R_{11}$ is —$SO_2CH_3$ and one $R_{11}$ is —$CH_2OH$. In another embodiment is a compound of Formula II wherein X is —CH=CH—; and $R_4$ is phenyl substituted with one $R_{11}$, wherein $R_{11}$ is —$SO_2R_{10}$ and $R_{10}$ is $C_1$-$C_6$alkyl. In another embodiment is a compound of Formula II wherein X is —CH=CH—; and "optionally substituted" means optionally substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl) amino.

In another embodiment is a compound of Formula II wherein X is —CH=CH, the compound is a compound of Formula (IIA):

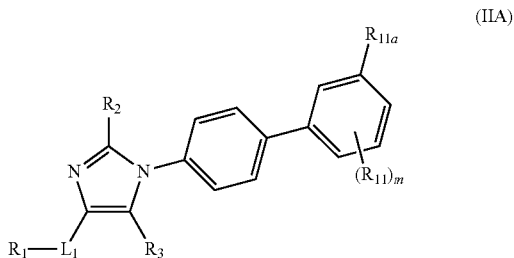

wherein:
$R_{11a}$ is —$NR_{10}SO_2R_{10}$, —$SOR_{10}$, —$SO_2R_{10}$, or —$SO_2N(R_{10})_2$; and
m is 0 or 1;
or a pharmaceutically acceptable salt thereof.

In another embodiment is a compound of Formula II wherein X is —CH=CH—, wherein the compound is a compound of Formula (IIB):

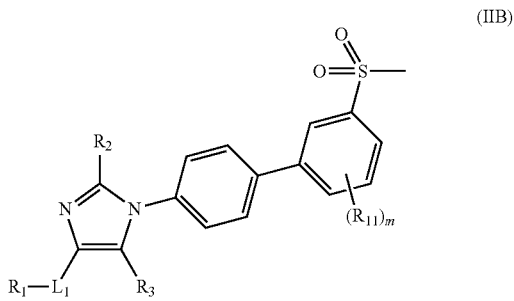

wherein m is 0 or 1;
or a pharmaceutically acceptable salt thereof.

In another embodiment is a compound of Formula II wherein:
X is —CH=CH—;
-$L_1$-$R_1$ is $C_1$-$C_6$alkyl, $C_1$-$C_6$alkyl-OH, or $C_1$-$C_6$haloalkyl;
$R_2$ is $C_1$-$C_6$ alkyl;
$R_3$ is hydrogen;
$R_4$ is phenyl; wherein said phenyl is substituted with at least one $R_{11}$;
each $R_{11}$ is independently —$NR_{10}SO_2R_{10}$, —$SOR_{10}$, —$SO_2R_{10}$, —$SO_2N(R_{10})_2$, or $C_1$-$C_6$alkyl, wherein said $C_1$-$C_6$alkyl is optionally substituted by 1 hydoxy;
provided that at least one $R_{11}$ is —$NR_{10}SO_2R_{10}$, —$SOR_{10}$, —$SO_2R_{10}$, or —$SO_2N(R_{10})_2$,
each $R_{10}$ is independently $C_1$-$C_6$ alkyl; and
n is 0.

In another embodiment is a compound of Formula II wherein:
X is —CH=CH—;
-$L_1$-$R_1$ is $C_1$-$C_6$alkyl, $C_1$-$C_6$alkyl-OH, or $C_1$-$C_6$haloalkyl;
$R_2$ is $C_1$-$C_6$ alkyl;
$R_3$ is hydrogen;
$R_4$ is phenyl; wherein said phenyl is substituted with at least one $R_{11}$; wherein each $R_{11}$ is independently —$SO_2R_{10}$, or $C_1$-$C_6$alkyl, wherein said $C_1$-$C_6$alkyl is optionally substituted by 1 hydoxy; provided that at least one $R_{11}$ is —$SO_2R_{10}$,
each $R_{10}$ is independently $C_1$-$C_6$ alkyl; and
n is 0.

In another embodiment, the compound is selected from:

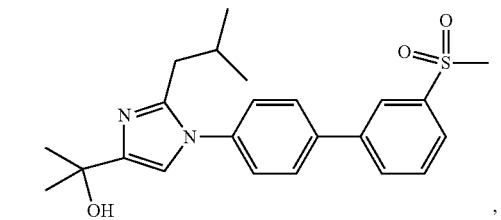

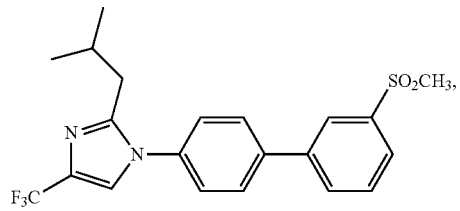

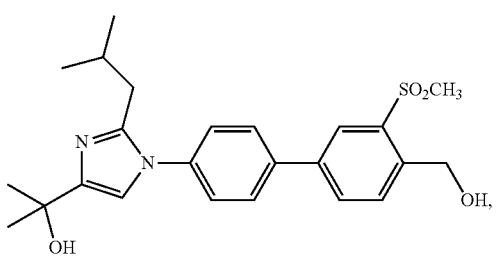

and

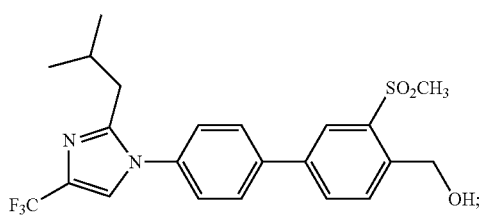

or a pharmaceutically acceptable salt thereof.

Any combination of the groups described above for the various variables is contemplated herein. Throughout the specification, groups and substituents thereof can be chosen by one skilled in the field to provide stable moieties and compounds.

In some embodiments is a compound selected from:

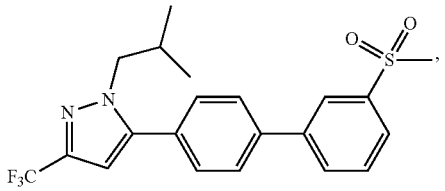

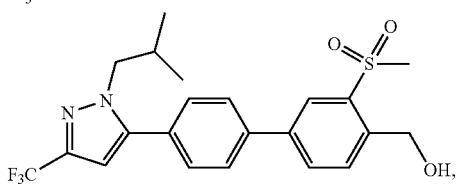

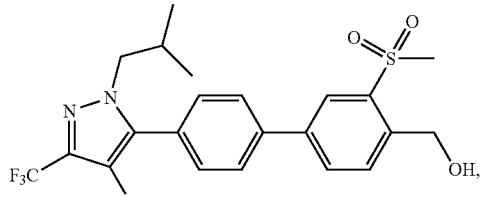

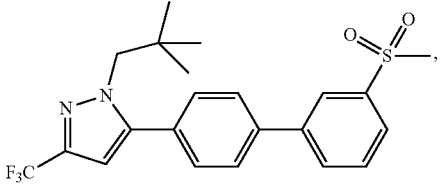

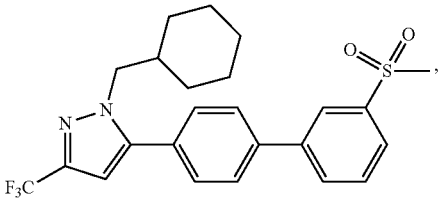

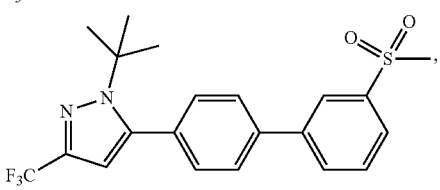

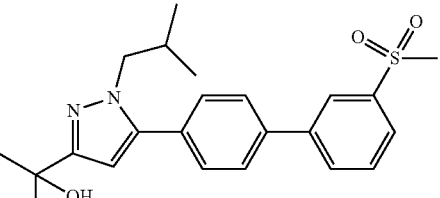

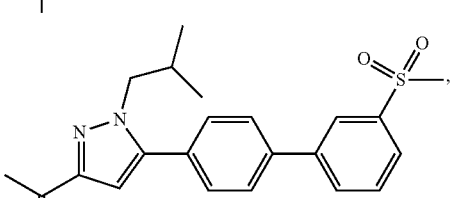

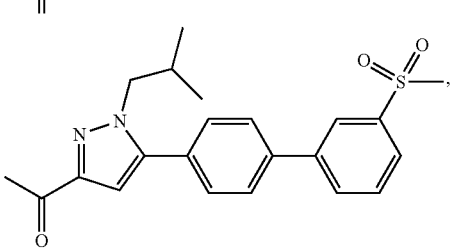

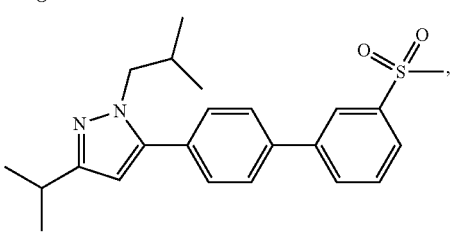

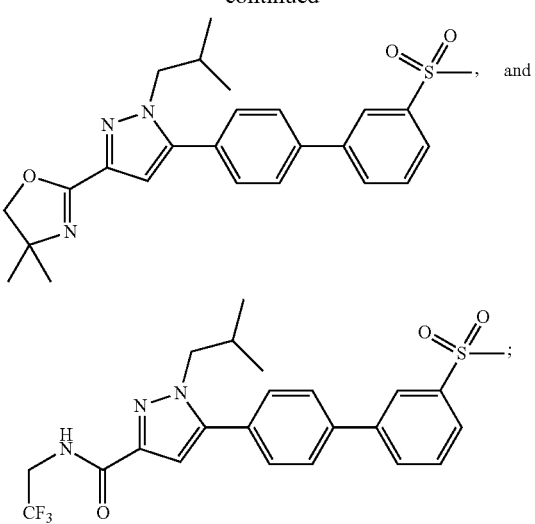

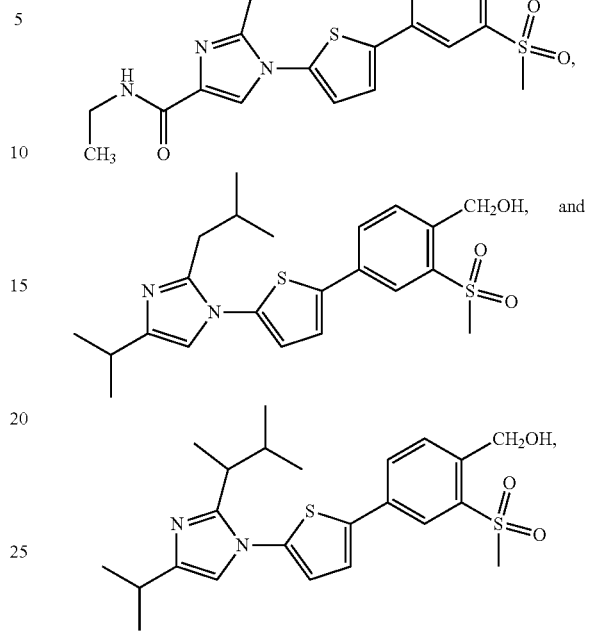

or a pharmaceutically acceptable salt, pharmaceutically acceptable solvate, or pharmaceutically acceptable prodrug thereof.

In some embodiments is a compound selected from:

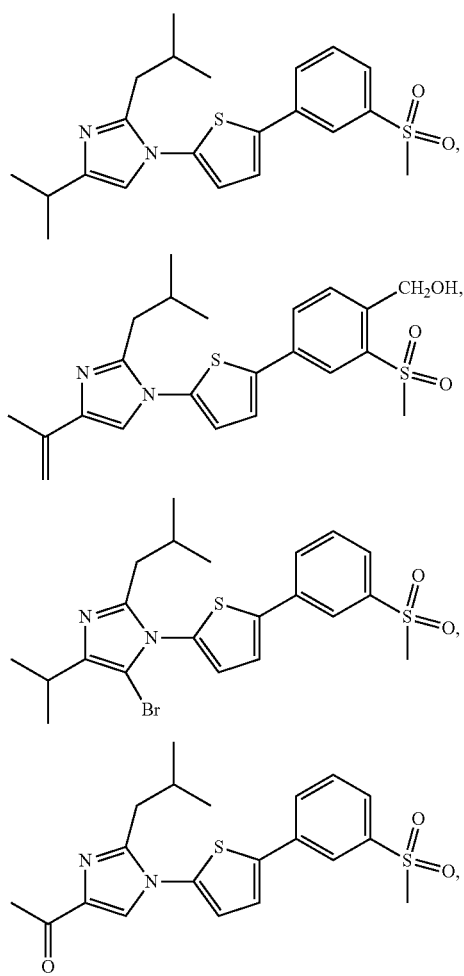

or a pharmaceutically acceptable salt, pharmaceutically acceptable solvate, or pharmaceutically acceptable prodrug thereof.

In some embodiments, the therapeutic agent(s) (e.g. compound of Formula I, IA, II or III is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula I, IA, IB, IC, II, IIA, or IIB is used as a single enantiomer. In some embodiments, a compound of Formula I, IA, IB, IC, II, IIA, or JIB is used as a racemic mixture.

The methods and formulations described herein include the use of N-oxides (if appropriate), crystalline forms (also known as polymorphs), or pharmaceutically acceptable salts of compounds having the structures presented herein, as well as active metabolites of these compounds having the same type of activity. In some situations, compounds may exist as tautomers. All tautomers are included within the scope of the compounds presented herein. In specific embodiments, the compounds or salts described herein exist in solvated forms with pharmaceutically acceptable solvents such as water, ethanol, and the like. In other embodiments, the compounds or salts described herein exist in unsolvated form.

In some embodiments, the compounds of Formula I, IA, IB, IC, II, IIA, or IIB or salts thereof described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

In some embodiments, sites on the compounds of Formula I, IA, IB, IC, II, IIA, or IIB disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula I, IA, IB, IC, II, IIA, or IIB disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

In some embodiments, compounds described herein, such as compounds of Formula I, IA, IB, IC, II, IIA, or IIB, are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles and/or nucleophiles to form new functional groups or substituents. Table IA entitled "Examples of Covalent Linkages and Precursors Thereof" lists selected non-limiting examples of covalent linkages and precursor functional groups which yield the covalent linkages. Table IA may be used as guidance toward the variety of electrophiles and nucleophiles combinations available that provide covalent linkages. Precursor functional groups are shown as electrophilic groups and nucleophilic groups.

TABLE IA

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |

TABLE IA-continued

Examples of Covalent Linkages and Precursors Thereof

| Covalent Linkage Product | Electrophile | Nucleophile |
|---|---|---|
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Alkyl amines | sulfonate esters | amines/anilines |
| hioethers | sulfonate esters | Thiols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

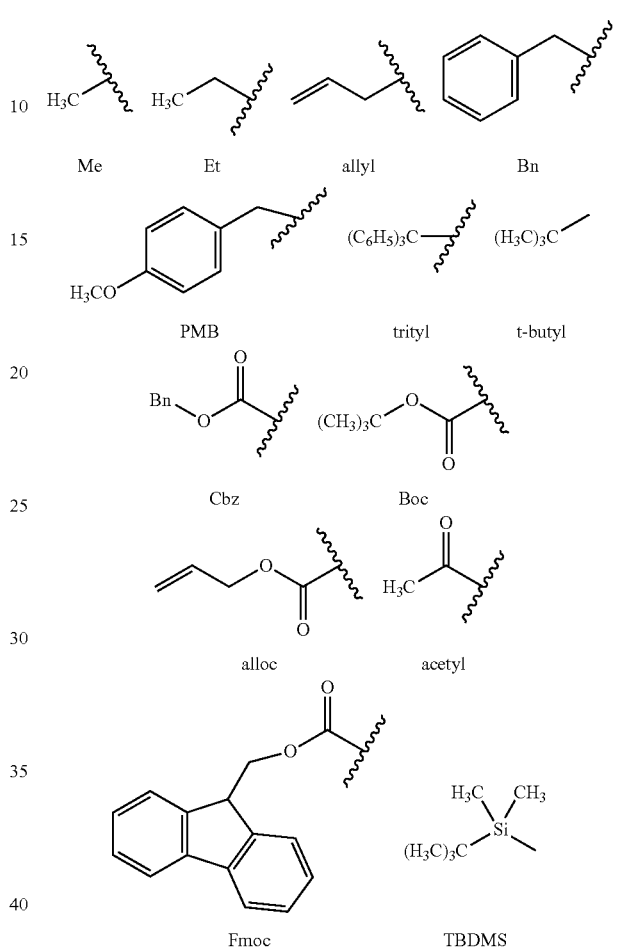

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic. In some embodiments, "alkyl" is a branched or straight-chain alkyl.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which two atoms of the alkyl group form a double bond that is not part of an aromatic group. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group). In some embodiments, "alkenyl" is a branched or straight-chain alkenyl.

The term "alkynyl" refers to a type of alkyl group in which the two atoms of the alkyl group form a triple bond. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

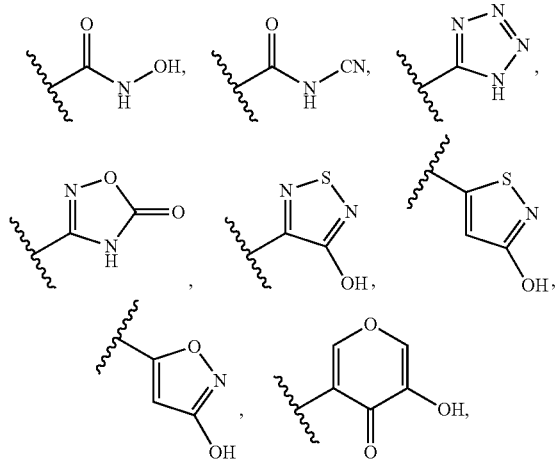

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

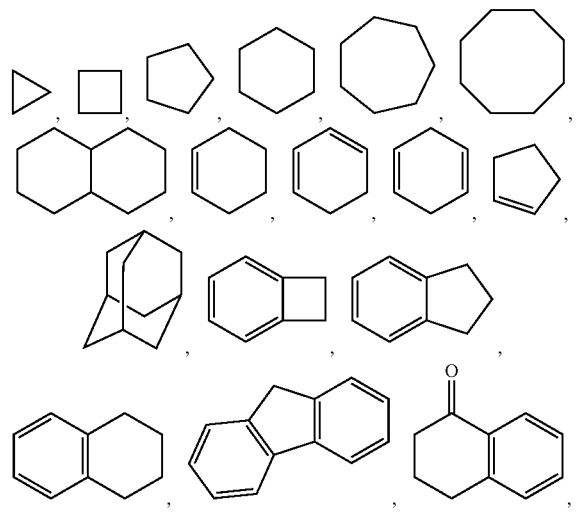

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

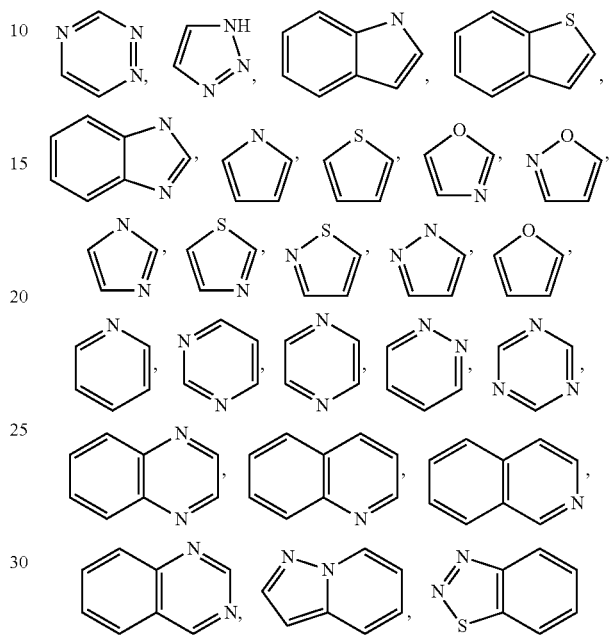

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

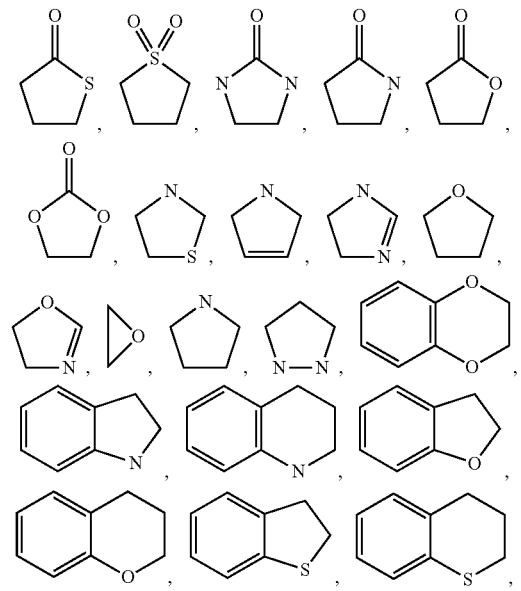

-continued

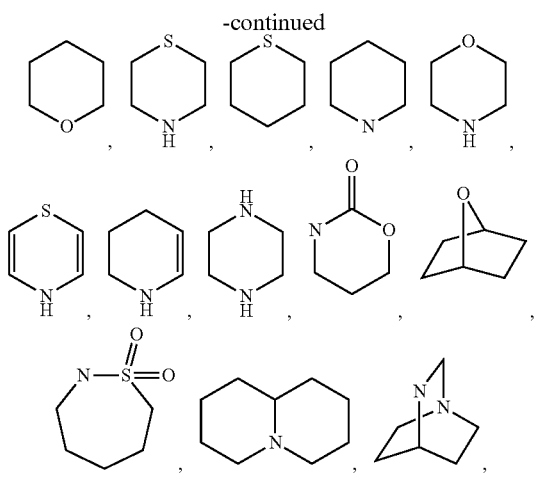

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, —$CF(CH_3)_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. In some embodiments, "optionally substituted" means optionally substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl)amino. The protecting groups that may form the protective derivatives of the above substituents are found in sources such as Greene and Wuts, above.

The methods and formulations described herein include the use of crystalline forms (also known as polymorphs), or pharmaceutically acceptable salts of compounds having the structure of Formulas I, IA, or II, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Methods of Treatment and Prevention

In one embodiment, provided herein are methods for stimulation of LXR activity in a cell by contacting the cell with an LXR modulator. Examples of such LXR modulators are described above. Other LXR modulators that can be used to stimulate the LXR activity are identified using screening assays that select for such compounds, as described in detail herein.

In another aspect, provided herein are methods of modulating LXR activity for the treatment of diseases, disorders or conditions described herein. Accordingly, in an exemplary embodiment, provided herein are methods which involve contacting a cell with an LXR modulator that induces TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, and/or decorin expression and/or inhibits TNFα, MMP1, MMP3, and/or IL-8 expression. These methods are performed in vitro (e.g., by culturing the cell with an LXR modulator) or, alternatively, in vivo (e.g., by administering an LXR modulator to a subject). As such, the present methods are directed to treating a subject that would benefit from induction of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, and/or decorin expression and/or inhibition of TNFα, MMP1, MMP3, and/or IL-8 expression.

LXR modulators increase expression of genes involved in fatty acid synthesis and lipid transport. The LXR ligand induced the expression of genes involved in fatty acid synthesis, namely SREBF1, SREBF2, FASN, and SCD, and genes involved in cholesterol and phospholipid transport namely APOE, APOD, ABCG1, ABCA1, ABCA12, ABCA2, and ABCA13. LXR modulators increase the expression of LASS4 and SMPD2.

Pharmaceutical Compositions and Methods of Administration of LXR Modulators

Administration of LXR modulators as described herein can be in any pharmacological form including a therapeutically effective amount of an LXR modulator alone or in combination with a pharmaceutically acceptable carrier. The term "subject" is intended to include living organisms in which an immune response can be elicited, for example, mammals.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula I, IA or II described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds of Formula I, IA or II can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of Formula I, IA or II described herein, can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

For treatment of solid tumors, localized delivery is also an option. Such delivery may be by injection, or may be topical, transmucosal, and the like. If the drugs are directed to treatment of melanoma, topical administration is a viable option.

For systemic parenteral delivery, a variety of physiologically acceptable carriers is available, including nanoparticulate formulations, liposomes, micelles, and the like. Such carriers can also be targeted using antibodies or fragments thereof specific for the targets, or by using receptor ligands. "Antibodies" includes all forms, including human and humanized antibodies as well as recombinantly produced single-chain antibodies and fragments.

Formulations for systemic administration by parenteral routes may include aqueous as well as lipophilic carriers. Similarly, formulations for administration, for example, by inhalation will include carriers that promote absorption across the nasal barrier and may be administered by aerosol spray using propellants such as trichlorofluoromethane, carbon dioxide or other propellant. The formulation to be administered may also be in the form of a powder or slurry.

The pharmaceutical compositions described herein, which include a compound of Formula I, IA or II described herein, may be administered using sustained release formulations including implants. Such implants may be used proximal to any solid tumor or implanted within said tumor.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the LXR modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the LXR modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such LXR modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. LXR modulators that exhibit large therapeutic indices are preferred. While LXR modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such LXR modulators lies preferably within a range of circulating concentrations that include the $ED_{50}$ with little or no toxicity. The dosage may vary within this range depending upon the dosage form employed and the route of administration utilized. For any LXR modulator used in a method described herein, the therapeutically effective dose can be estimated initially from cell culture assays. A dose may be formulated in animal models to achieve a circulating plasma concentration range that includes the $IC_{50}$ (i.e., the concentration of LXR modulator that achieves a half-maximal inhibition of symptoms) as determined in cell culture. Such information can be used to more accurately determine useful doses in humans. Levels in plasma may be measured, for example, by high performance liquid chromatography.

Monitoring the influence of LXR modulators on the induction of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, and/or decorin expression and/or inhibition of TNFα, MMP1, MMP3, and/or IL-8 expression is applied in clinical trials. For example, the effectiveness of an LXR modulator is monitored in clinical trials of subjects exhibiting increased TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, and/or decorin expression and/or decreased TNFα, MMP1, MMP3, and/or IL-8 expression. In such clinical trials, the expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 is used as a "read out" or marker.

Thus, to study the effect of LXR modulators, for example, in a clinical trial, cells are isolated and RNA prepared and analyzed for the levels of expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8. The levels of gene expression (i.e., a gene expression pattern) is quantified, for example, by Northern blot analysis or RT-PCR, by measuring the amount of protein produced, or by measuring the levels of activity of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8, all by methods well known to those of ordinary skill in the art. In this way, the gene expression pattern serves as a marker, indicative of the physiological response of the cells to the LXR modulator. Accordingly, this response state is determined before, and at various points during, treatment of the individual with the LXR modulator.

Also provided is a method for monitoring the effectiveness of treatment of a subject with an LXR modulator comprising the steps of (i) obtaining a pre-administration sample from a subject prior to administration of the LXR modulator; (ii) detecting the level of expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8; (iii) obtaining one or more post-administration samples from the subject; (iv) detecting the level of expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 in the post-administration samples; (v) comparing the level of expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 in the pre-administration sample with the TIMP1, ABCA12, decorin, TNFα, MMP1, MMP3, and/or IL-8 expression in the post administration sample or samples; and (vi) altering the administration of the LXR modulator to the subject accordingly.

For example, increased administration of the LXR modulator may be desirable to increase TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, and/or decorin expression to higher levels than detected and/or reduce TNFα, MMP1, MMP3, and/or IL-8 expression to lower levels than detected, that is, to increase the effectiveness of the LXR modulator. Alternatively, decreased administration of the LXR modulator may be desirable to decrease TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, and/or decorin expression to lower levels than detected or activity and/or to increase TNFα, MMP1, MMP3, and/or IL-8 expression to higher levels than detected, that is, to decrease the effectiveness of the LXR modulator. According to such an embodiment, TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression may be used as an indicator of the effectiveness of an LXR modulator, even in the absence of an observable phenotypic response.

Screening Assays

In one embodiment, expression levels of cytokines and metalloproteases described herein are used to facilitate design and/or identification of compounds that work through an LXR-based mechanism. Accordingly provided herein are methods (also referred to herein as "screening assays") for identifying modulators, i.e., LXR modulators, that have a stimulatory or inhibitory effect on, for example, TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression.

An exemplary screening assay is a cell-based assay in which a cell that expresses LXR is contacted with a test compound, and the ability of the test compound to modulate TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression through an LXR-based mechanism. Determining the ability of the test compound to modulate TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression is accomplished by monitoring, for example, DNA, mRNA, or protein levels, or by measuring the levels of activity of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8. The cell, for example, is of mammalian origin, e.g., human.

Novel modulators identified by the above-described screening assays are used for treatments as described herein.

EXAMPLES

The following examples are offered for purposes of illustration, and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1

Synthesis of 1-isobutyl-5-(3'-(methylsulfonyl)biphenyl-4-yl)-3-(trifluoromethyl)-1H-pyrazole (4)

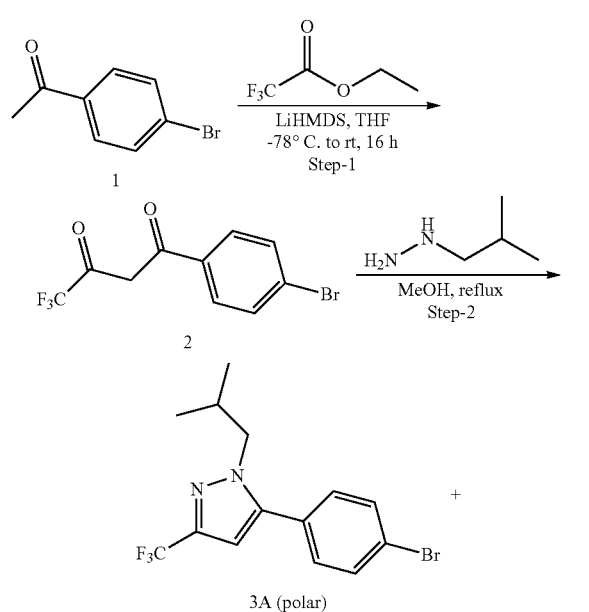

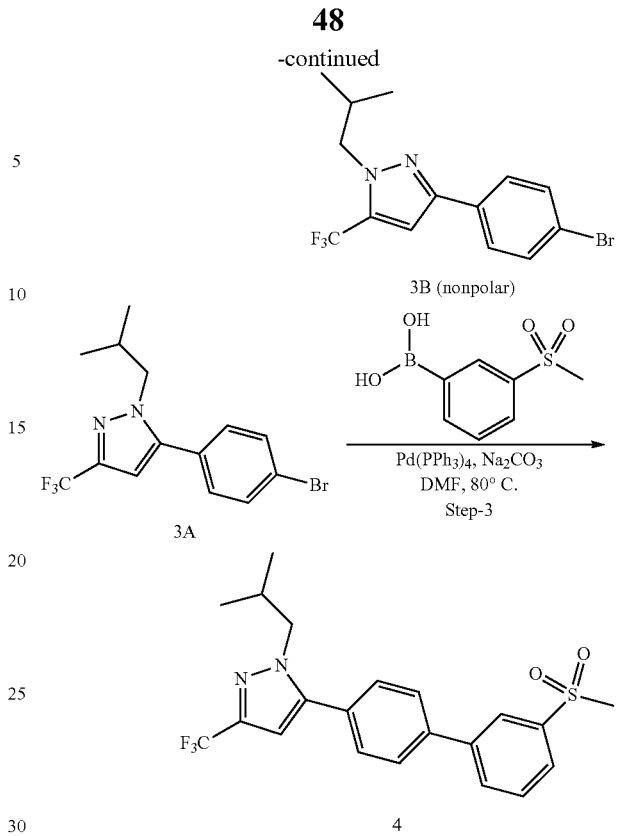

Following the reaction sequence above, the title compound 4 was prepared starting from 1-(4-bromophenyl)ethanone 1 and ethyl trifluoroacetate. LCMS: 423.25.10 (M+1)$^+$; HPLC: 96.20% (@ 210 nm-370 nm) (R$_t$; 8.064; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (CDCl$_3$, 400 MHz) δ 8.22 (s, 1H), 7.95 (dd, 2H), 7.74 (d, 2H, J=7.6 Hz), 7.72 (d, 1H), 7.50 (d, 2H, J=7.6 Hz), 7.26 (s, 1H), 4.02 (d, 2H), 3.12 (s, 3H), 2.24 (m, 1H), 0.81 (d, 6H).

Example 2

Synthesis of (4'-(1-isobutyl-3-(trifluoromethyl)-1H-pyrazol-5-yl)-3-(methylsulfonyl)biphenyl-4-yl)methanol (5)

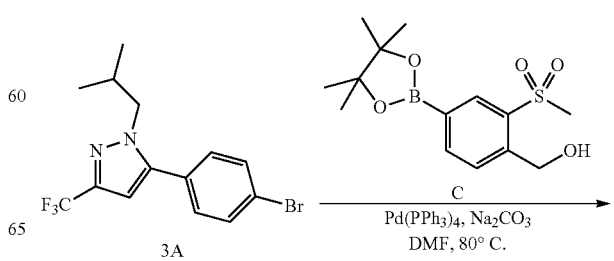

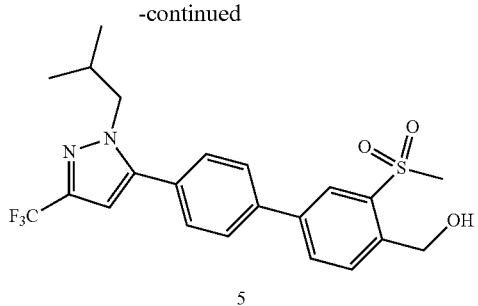

5

The title compound 5 was prepared starting from 5-(4-bromophenyl)-1-isobutyl-3-(trifluoromethyl)-1H-pyrazole 3A and (2-(methylsulfonyl)-4-(4,4,5,5-tetramethyl-1,3,2-dioxaborolan-2-yl)phenyl)methanol. LCMS: 453.30.10 (M+1)$^+$; HPLC: 96.20% (@ 210 nm-370 nm) (R$_t$; 7.649; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (CDCl$_3$, 400 MHz) δ 8.32 (s, 1H), 7.92 (brd, 1H), 7.74 (d, 2H, J=7.6 Hz), 7.71 (d, 1H), 7.50 (d, 2H, J=7.6 Hz), 7.26 (s, 1H), 6.56 (s, 1H), 5.02 (brd, 2H), 4.00 (d, 2H), 3.24 (s, 1H), 3.00 (m, 1H), 2.24 (m, 1H), 0.80 (s, 6H).

Example 1A

Alternative Synthesis 1-isobutyl-5-(3'-(methylsulfonyl)biphenyl-4-yl)-3-(trifluoromethyl)-1H-pyrazole (4)

Scheme C

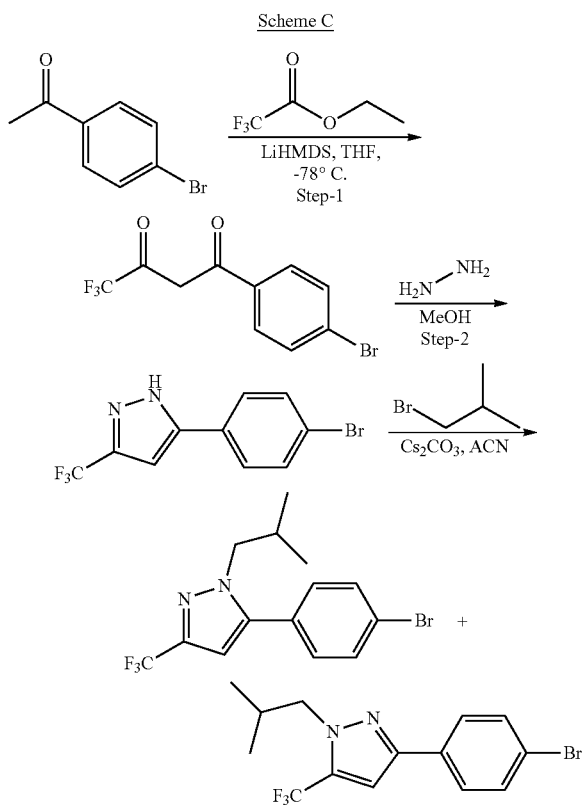

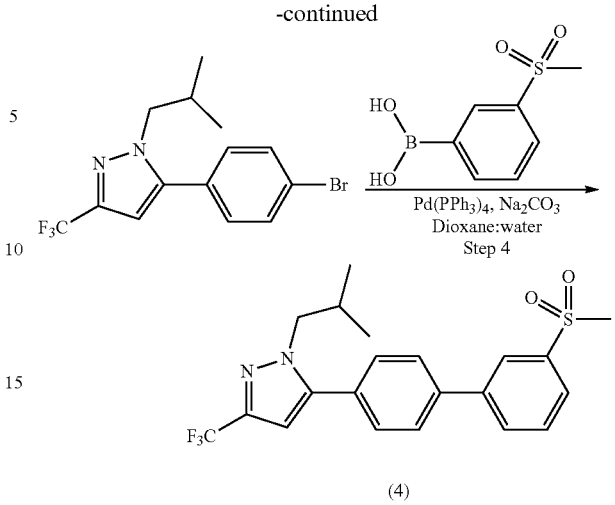

Step 1:
1-(4-Bromophenyl)-4,4,4-trifluorobutane-1,3-dione

To a stirred solution of 1-(4-bromophenyl)ethanone (25 g, 125.6 mmol) in dry THF (250 mL) at −78° C., LiHMDS (1 M, 188 mL, 188.4 mmol) was added and the solution was stirred at same temperature for 1 h. To this solution, ethyl 2,2,2-trifluoroacetate (22.44 mL, 188.4 mmol) in THF (20 mL) was added at −78° C. and the resulting reaction mixture was stirred at rt for 12 h. The progress of the reaction was monitored by TLC. Upon completion the reaction mixture was quenched with aqueous sat. NH$_4$Cl solution and extracted with ethyl acetate. The combined organic layers were dried over anhydrous Na$_2$SO$_4$ and concentrated under reduced pressure resulting in a crude compound which was purified by column chromatography to afford the title compound (35 g, 94.4%).

Step 2:
5-(4-Bromophenyl)-3-(trifluoromethyl)-1H-pyrazole

To a stirred solution of 1-(4-Bromophenyl)-4,4,4-trifluorobutane-1,3-dione (1 g, 3.39 mmol) in MeOH (10 mL), hydrazine hydrate (0.186 g, 3.73 mmol) was added, and the resulting reaction mixture was stirred at 90° C. for 6 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous Na$_2$SO$_4$ and concentrated under reduced pressure resulting in a crude compound which was purified by column chromatography to afford the title compound (0.6 g, 61.2%).

Step 3: 5-(4-Bromophenyl)-1-isobutyl-3-(trifluoromethyl)-1H-pyrazole

To a stirred solution of 5-(4-bromophenyl)-3-(trifluoromethyl)-1H-pyrazole (1 g, 3.45 mmol) in ACN (10 mL), 1-bromo-2-methylpropane (0.709 g, 5.18 mmol) and Cs$_2$CO$_3$ (2.24 g, 6.90 mmol) were added and the resulting reaction mixture was stirred at 80° C. for 6 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous Na$_2$SO$_4$ and concentrated under reduced pressure resulting in a crude compound which was purified by column chromatography to afford the title compound (0.44 g, 38%).

Step 4: 1-Isobutyl-5-(3'-(methylsulfonyl)-[1,1'-biphenyl]-4-yl)-3-(trifluoromethyl)-1H-pyrazole (4)

To a stirred solution of 5-(4-bromophenyl)-1-isobutyl-3-(trifluoromethyl)-1H-pyrazole (5.3 g, 15.32 mmol) and (3-(methylsulfonyl)phenyl)boronic acid (3 g, 15.32 mmol) in dioxane/water mixture (50 mL+10 mL), Na$_2$CO$_3$ (3.2 g, 30.64 mmol) was added and the solution was purged with argon for 10 min. Then Pd (PPh$_3$)$_4$ (1.76 g, 1.53 mmol) was added and argon was purged again for 10 min. The reaction mass was heated at 100° C. for 3 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound 4 (5.2 g, 80.5%). LCMS: 423.10 (M+1)$^+$; HPLC: 98.55% (@ 210 nm-400 nm) (Rt; 10.354; Method: YMC TRIART C-18 (150 mm×4.6 mm×3µ); ID:E-AC-2/13/COL/03, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, CDCl$_3$) δ 8.22 (d, J=2.2 Hz, 1H), 8.01-7.90 (m, 2H), 7.78-7.66 (m, 3H), 7.51 (dd, J=8.3, 2.4 Hz, 2H), 6.57 (d, J=2.3 Hz, 1H), 4.01 (dd, J=7.7, 2.4 Hz, 2H), 3.13 (d, J=2.3 Hz, 3H), 2.23 (hept, J=6.8 Hz, 1H), 0.80 (dd, J=7.0, 2.4 Hz, 6H).

To a stirred solution of 5-(4-bromophenyl)-1-isobutyl-3-(trifluoromethyl)-1H-pyrazole of Example 1A, step 4 (5 g, 14.45 mmol) and (2-(methylsulfonyl)-4-(4,4,5,5-tetramethyl-1,3,2-dioxaborolan-2-yl)phenyl)methanol (6.81 g, 21.68 mmol) in dioxane/water mixture (50 mL+10 mL), Na$_2$CO$_3$ (3.06 g, 28.90 mmol) was added and the solution was purged with argon for 10 min. Then Pd (PPh$_3$)$_4$ (1.67 g, 1.445 mmol) was added and argon was purged again for 10 min. The reaction mass was heated at 100° C. for 16 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound 5 (3.1 g, 47.4%). LCMS: 453.10 (M+1)$^+$; HPLC: 95.04% (@ 210 nm-400 nm) (Rt; 9.773; Method: YMC TRIART C-18 (150 mm×4.6 mm×3µ); ID:E-AC-2/13/COL/03, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, CDCl$_3$) δ 8.32 (d, J=1.9 Hz, 1H), 7.92 (dd, J=7.9, 2.0 Hz, 1H), 7.78-7.65 (m, 3H), 7.54-7.44 (m, 2H), 6.57 (s, 1H), 5.02 (d, J=6.7 Hz, 2H), 4.01 (d, J=7.5 Hz, 2H), 3.24 (s, 3H), 3.02 (t, J=6.8 Hz, 1H), 2.23 (hept, J=7.0 Hz, 1H), 0.80 (d, J=6.7 Hz, 6H).

Example 3

Synthesis of 1-Isobutyl-5-(3'-(methylsulfonyl)-[1,1'-biphenyl]-4-yl)-N-(2,2,2-trifluoroethyl)-1H-pyrazole-3-carboxamide (6)

Example 2A

Alternative Synthesis of (4'-(1-isobutyl-3-(trifluoromethyl)-1H-pyrazol-5-yl)-3-(methylsulfonyl)-[1,1'-biphenyl]-4-yl)methanol (5)

Scheme D

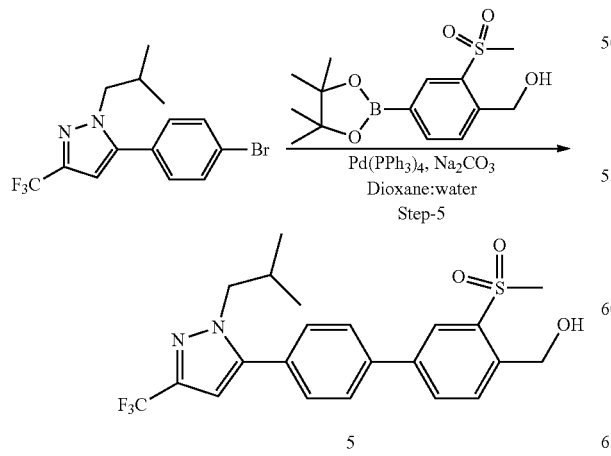

Scheme E

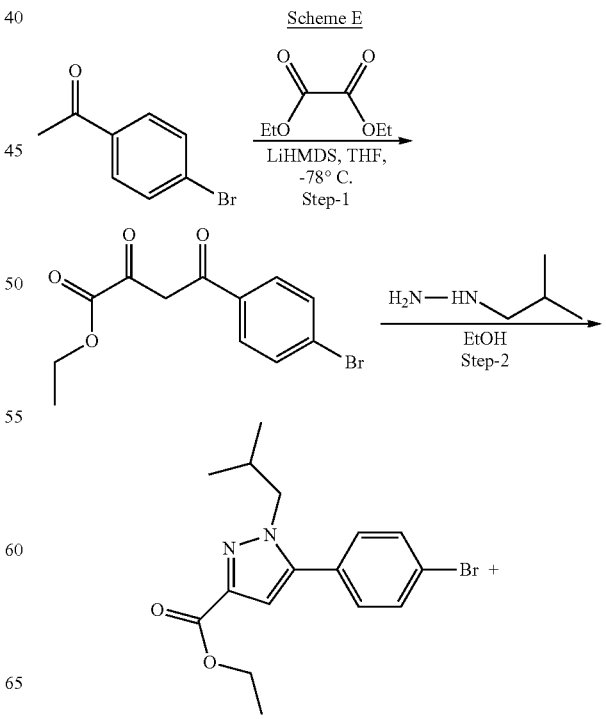

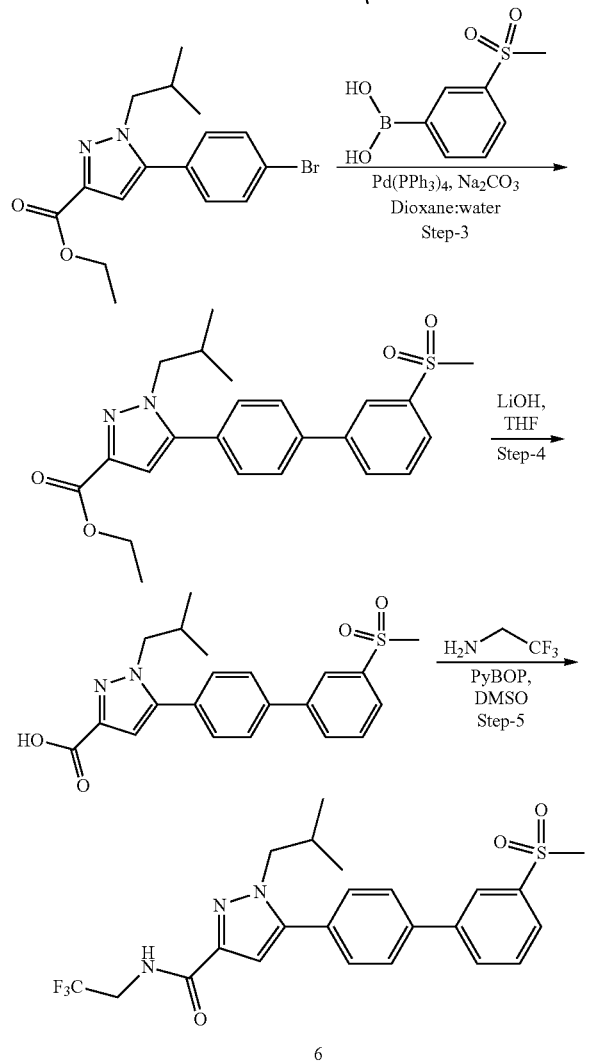

Step 1: Ethyl 4-(4-bromophenyl)-2,4-dioxobutanoate

To a stirred solution of 1-(4-bromophenyl)ethanone (5 g, 25.38 mmol) in dry THF (50 mL) at −78° C., LiHMDS (1 M, 28 mL, 27.91 mmol) was added and the solution was stirred at same temperature for 1 h. To this solution, diethyl oxalate (4.08 g, 27.91 mmol) in THF (10 mL) was added at −78° C. and the resulting reaction mixture was stirred at rt for 12 h. The progress of the reaction was monitored by TLC and LCMS. Upon completion the reaction mixture was quenched with aqueous sat. NH₄Cl solution and extracted with ethyl acetate. The combined organic layers were dried over anhydrous Na₂SO₄ and concentrated under reduced pressure resulting in a crude compound which was purified by column chromatography to afford the title compound (2.5 g, 33.3%).

Step 2: Ethyl 5-(4-bromophenyl)-1-isobutyl-1H-pyrazole-3-carboxylate

To a stirred solution of the product of the previous step (1 g, 3.35 mmol) in EtOH (20 mL), isobutyl hydrazine hydrochloride (0.45 g, 3.69 mmol) was added and the resulting reaction mixture was stirred at 80° C. for 3 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous Na₂SO₄ and concentrated under reduced pressure to afford a crude compound which was purified by column chromatography to afford ethyl 5-(4-bromophenyl)-1-isobutyl-1H-pyrazole-3-carboxylate (0.7 g, 60%) which was confirmed by NOE experiment.

Step 3: Ethyl 1-isobutyl-5-(3'-(methylsulfonyl)-[1,1'-biphenyl]-4-yl)-1H-pyrazole-3-carboxylate To a stirred solution of ethyl 5-(4-bromophenyl)-1-isobutyl-1H-pyrazole-3-carboxylate (0.7 g, 2.0 mmol) and (3-(methylsulfonyl)phenyl)boronic acid (0.42 g, 2.10 mmol) in dioxane/water mixture (8 mL+2 mL), Na₂CO₃ (0.530 g, 5.0 mmol) was added, and the solution was purged with argon for 10 min. Then Pd (PPh₃)₄ (0.231 g, 0.2 mmol) was added and argon was purged again for 10 min. The reaction mass was heated at 80° C. for 6 h. The progress of the reaction was monitored by TLC. Upon completion the reaction mixture diluted with water and extracted with ethyl acetate. The combined organic layers were dried over Na₂SO₄ and concentrated under reduced pressure. The crude compound was purified by column chromatography to afford the desired compound (0.5 g, 59%). LCMS: 427.15 (M+1)⁺; HPLC: 99.83% (@ 210 nm-400 nm) (Rt; 9.552; Method: YMC TRIARTC-18 (150 mm×4.6 mm×3µ); ID:E-AC-2/13/COL/03, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.24 (d, J=2.2 Hz, 1H), 8.13 (d, J=7.7 Hz, 1H), 7.94 (t, J=7.6 Hz, 3H), 7.78 (t, J=7.8 Hz, 1H), 7.67 (d, J=7.9 Hz, 2H), 6.91 (d, J=1.9 Hz, 1H), 4.30 (q, J=7.0 Hz, 2H), 4.09 (d, J=7.4 Hz, 2H), 3.33 (s, 3H), 2.05 (tq, J=12.4, 7.0 Hz, 1H), 1.31 (t, J=7.1 Hz, 3H), 0.72 (d, J=6.6 Hz, 6H).

Step 4: 1-Isobutyl-5-(3'-(methylsulfonyl)-[1,1'-biphenyl]-4-yl)-1H-pyrazole-3-carboxylic acid To a stirred solution of the product of the previous step (0.5 g, 1.17 mmol) in THF (5 mL), LiOH (0.056 g, 2.34 mmol in 2 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with 10% MeOH/DCM. The combined organic layers were dried over Na₂SO₄ and concentrated under reduced pressure. The crude compound was purified by acetonitrile and diethyl ether washings to afford the desired compound (0.35 g, 75%). LCMS: 399.25 (M+1)⁺; HPLC:

98.86% (@ 210 nm-400 nm) (Rt; 7.756; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 12.73 (s, 1H), 8.24 (d, J=1.8 Hz, 1H), 8.12 (dt, J=8.0, 1.3 Hz, 1H), 7.94 (dd, J=10.1, 7.7 Hz, 3H), 7.78 (t, J=7.8 Hz, 1H), 7.70-7.63 (m, 2H), 6.86 (s, 1H), 4.08 (d, J=7.4 Hz, 2H), 3.32 (s, 3H), 2.07 (dp, J=13.8, 6.9 Hz, 1H), 0.73 (d, J=6.7 Hz, 6H).

Step 5: 1-Isobutyl-5-(3'-(methylsulfonyl)-[1,1'-biphenyl]-4-yl)-N-(2,2,2-trifluoroethyl)-1H-pyrazole-3-carboxamide (6)

To a stirred solution of the product of the previous step (0.15 g, 0.376 mmol) in DMSO (1 mL), 2,2,2-trifluoroethanamine (0.044 g, 0.452 mmol) and triethyl amine (0.15 mL, 1.13 mmol) were added. The reaction mixture was stirred at rt for 15 min before PyBOP (0.293 g, 0.565 mmol) was added to it at 0° C., and stirring was continued at rt for 16 h. The progress of the reaction was monitored by TLC. Upon completion the reaction mixture was diluted with water and extracted with 10% MeOH/DCM. The combined organic layers were dried over Na$_2$SO$_4$ and concentrated under reduced pressure. The crude compound was purified by column chromatography to afford the title compound 6 (0.06 g, 33.3%). LCMS: 480.30 (M+1)$^+$; HPLC: 98.19% (@ 210 nm-400 nm) (Rt; 9.246; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.73 (t, J=6.5 Hz, 1H), 8.24 (d, J=1.9 Hz, 1H), 8.13 (dt, J=8.1, 1.4 Hz, 1H), 7.95 (dd, J=8.6, 6.7 Hz, 3H), 7.79 (t, J=7.8 Hz, 1H), 7.71-7.64 (m, 2H), 6.87 (s, 1H), 4.11-3.97 (m, 4H), 3.32 (s, 3H), 2.14 (hept, J=6.8 Hz, 1H), 0.75 (d, J=6.7 Hz, 6H).

Example 4

Synthesis of 5-(4'-(Hydroxymethyl)-3'-(methylsulfonyl)-[1,1'-biphenyl]-4-yl)-1-isobutyl-N-(2,2,2-trifluoroethyl)-1H-pyrazole-3-carboxamide (7)

Scheme F

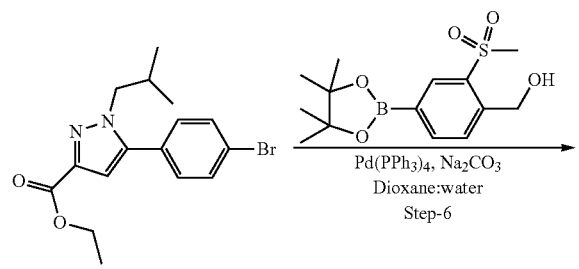

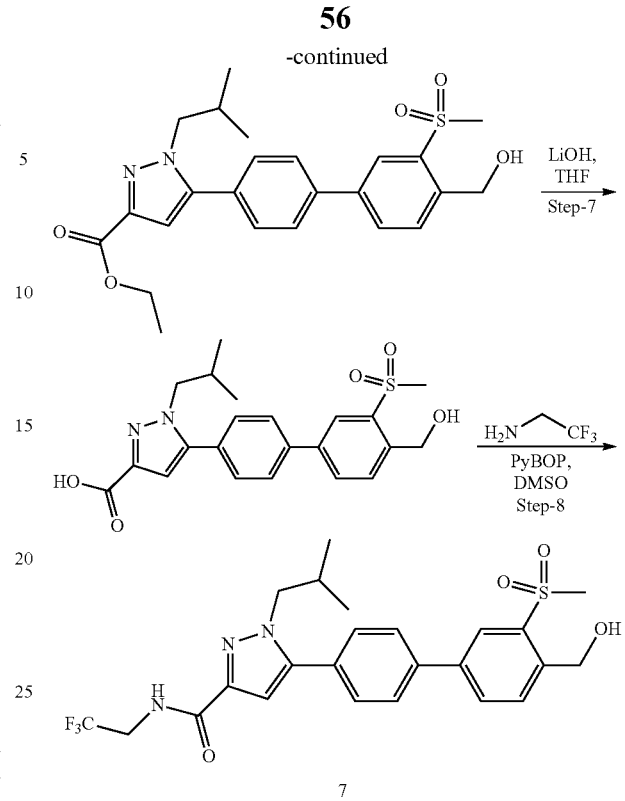

Step 1: Ethyl 5-(4'-(hydroxymethyl)-3'-(methylsulfonyl)-[1,1'-biphenyl]-4-yl)-1-isobutyl-1H-pyrazole-3-carboxylate To a stirred solution of ethyl 5-(4-bromophenyl)-1-isobutyl-1H-pyrazole-3-carboxylate from Example 3, step 2 (1 g, 2.85 mmol) and (2-(methylsulfonyl)-4-(4,4,5,5-tetramethyl-1,3,2-dioxaborolan-2-yl)phenyl)methanol (1.3 g, 4.28 mmol) in dioxane/water mixture (10 mL+4 mL), Na$_2$CO$_3$ (0.76 g, 7.14 mmol) was added and the solution was purged with argon for 10 min. Then Pd (PPh$_3$)$_4$ (0.33 g, 0.285 mmol) was added and argon was purged again for 10 min. The reaction mass was heated at 80° C. for 16 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound (1 g, 77%). LCMS: 457.35 (M+1)$^+$; HPLC: 98.29% (@ 210 nm-400 nm) (Rt; 8.802; Method: YMC TRIARTC-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.21-8.08 (m, 2H), 7.89 (dd, J=8.1, 4.6 Hz, 3H), 7.70-7.63 (m, 2H), 6.90 (s, 1H), 5.55 (t, J=5.6 Hz, 1H), 4.97 (d, J=5.6 Hz, 2H), 4.30 (q, J=7.1 Hz, 2H), 4.09 (d, J=7.4 Hz, 2H), 3.33 (s, 3H), 2.06 (dp, J=13.7, 6.7 Hz, 1H), 1.31 (t, J=7.1 Hz, 3H), 0.73 (d, J=6.7 Hz, 6H).

Step 2: 5-(4'-(Hydroxymethyl)-3'-(methylsulfonyl)-[1,1'-biphenyl]-4-yl)-1-isobutyl-1H-pyrazole-3-carboxylic acid To a stirred solution of the product of the previous step (0.3 g, 0.657 mmol) in THF (3 mL), LiOH (0.031 g, 1.32 mmol in 1 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with 10% MeOH/DCM. The combined organic layers were dried over Na₂SO₄ and concentrated under reduced pressure. The crude compound was purified by acetonitrile and diethyl ether washings to afford the desired compound (0.25 g, 89%). LCMS: 429.30 (M+1)⁺; HPLC: 98.89% (@ 210 nm-400 nm) (Rt; 6.968; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 12.74 (s, 1H), 8.21-8.08 (m, 2H), 7.91-7.87 (m, 3H), 7.74-7.62 (m, 2H), 6.85 (s, 1H), 5.55 (t, J=5.6 Hz, 1H), 4.97 (d, J=5.5 Hz, 2H), 4.07 (d, J=7.4 Hz, 2H), 3.33 (s, 3H), 2.07 (hept, J=6.6 Hz, 1H), 0.73 (d, J=6.7 Hz, 6H).

Step 3: 5-(4'-(Hydroxymethyl)-3'-(methylsulfonyl)-[1,1'-biphenyl]-4-yl)-1-isobutyl-N-(2,2,2-trifluoro-ethyl)-1H-pyrazole-3-carboxamide (7)

To a stirred solution of the product of the previous step (0.1 g, 0.233 mmol) in DMSO (1 mL), 2,2,2-trifluoroethanamine (0.030 g, 0.280 mmol) and triethyl amine (0.1 mL, 0.70 mmol) were added. The reaction mixture was stirred at rt for 15 min before PyBOP (0.182 g, 0.350 mmol) was added to it at 0° C. and stirring was continued at rt for 16 h. The progress of the reaction was monitored by TLC. Upon completion the reaction mixture was diluted with water and extracted with 10% MeOH/DCM. The combined organic layers were dried over Na₂SO₄ and concentrated under reduced pressure. The crude compound was purified by column chromatography to afford the title compound 7 (0.04 g, 34%). LCMS: 510.00 (M+1)⁺; HPLC: 99.88% (@ 210 nm-400 nm) (Rt; 8.495; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 5% B to 95% B in 8 min, Hold till 9.5 min, 5% B in 13.0 min. hold till 15.0 min); ¹H NMR (400 MHz, DMSO-d6) δ 8.73 (t, J=6.5 Hz, 1H), 8.21-8.08 (m, 2H), 7.90 (dd, J=8.1, 3.1 Hz, 3H), 7.70-7.63 (m, 2H), 6.86 (s, 1H), 5.55 (t, J=5.5 Hz, 1H), 4.97 (d, J=5.5 Hz, 2H), 4.11-3.97 (m, 4H), 3.33 (s, 3H), 2.14 (dq, J=13.8, 7.0 Hz, 1H), 0.75 (d, J=6.7 Hz, 6H).

Example 5

Synthesis of 2-(2-isobutyl-1-(3'-(methylsulfonyl)-[1,1'-biphenyl]-4-yl)-1H-imidazol-4-yl)propan-2-ol (8)

Scheme G

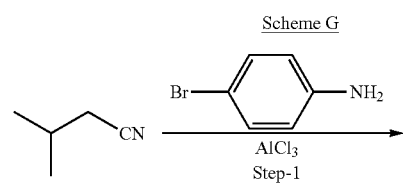

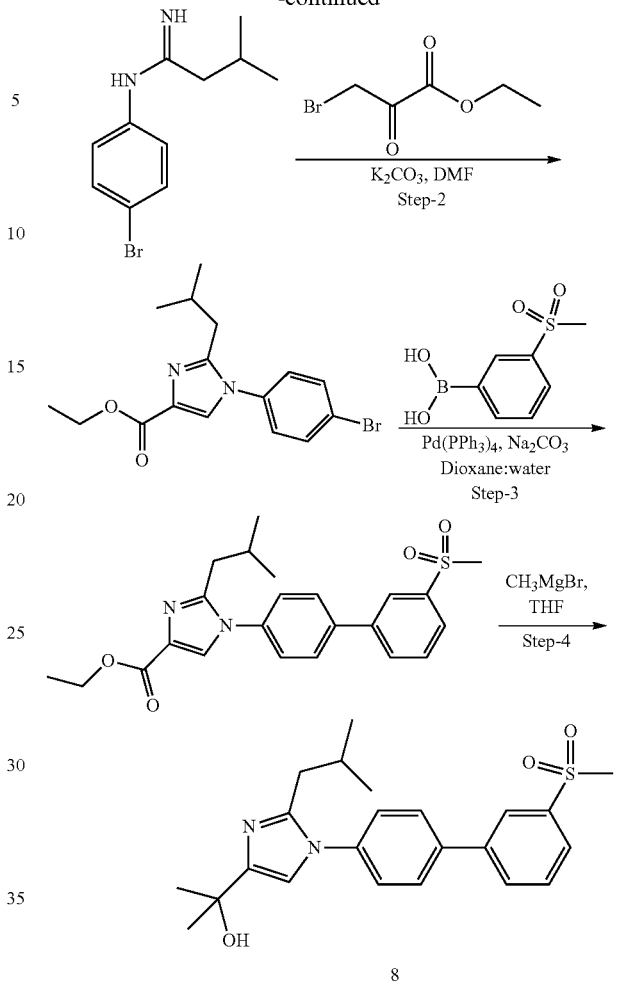

Step 1:
N-(4-Bromophenyl)-3-methylbutanimidamide

To a mixture of 4-bromoaniline (2.27 g, 13.25 mmol) and 3-methylbutanenitrile (1 g, 12.05 mmol) at 0° C., AlCl₃ (1.76 g, 13.25 mmol) was added portion wise. The resulting reaction mixture was stirred at 90° C. for 2 h. The progress of the reaction was monitored by TLC. Upon completion the reaction mixture was quenched with ice cold water and extracted with ethyl acetate. The combined organic layers were dried over anhydrous Na₂SO₄ and concentrated under reduced pressure resulting in a crude compound which was purified by column chromatography to afford the desired compound (1.5 g, 49%).

Step 2: Ethyl 1-(4-bromophenyl)-2-isobutyl-1H-imidazole-4-carboxylate

To a stirred solution of the product of the previous step (0.5 g, 1.96 mmol) in DMF (5 mL), ethyl 3-bromo-2-oxopropanoate (0.57 g, 2.94 mmol) and potassium carbonate (0.67 g, 4.9) were added and the resulting reaction mixture was stirred at 90° C. for 16 h. The progress of the reaction was monitored by TLC. Upon completion the reaction mixture was quenched with ice cold water and extracted with ethyl acetate. The combined organic layers were dried over anhydrous Na$_2$SO$_4$ and concentrated under reduced pressure resulting in a crude compound which was purified by column chromatography to afford the desired compound (0.3 g, 44%).

Step 3: Ethyl 2-isobutyl-1-(3'-(methylsulfonyl)-[1,1'-biphenyl]-4-yl)-1H-imidazole-4-carboxylate To a stirred solution of the product of the previous step (0.3 g, 0.854 mmol) and (3-(methylsulfonyl)phenyl) boronic acid (0.188 g, 0.940 mmol) in dioxane/water mixture (8 mL+2 mL), Na$_2$CO$_3$ (0.22 g, 2.13 mmol) was added and the solution was purged with argon for 10 min. Then Pd (PPh$_3$)$_4$ (0.098 g, 0.0854 mmol) was added and argon was purged again for 10 min. The reaction mass was heated at 100° C. for 3 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound (0.26 g, 72.2%). LCMS: 427.25 (M+1)$^+$; HPLC: 99.92% (@ 210 nm-400 nm) (Rt; 7.376; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.25 (d, J=1.9 Hz, 1H), 8.17-8.09 (m, 1H), 8.04-7.88 (m, 4H), 7.79 (t, J=7.8 Hz, 1H), 7.64 (d, J=8.3 Hz, 2H), 4.25 (q, J=7.1 Hz, 2H), 2.55 (d, J=7.2 Hz, 2H), 1.94 (dt, J=13.7, 6.8 Hz, 1H), 1.29 (t, J=7.1 Hz, 3H), 0.81 (d, J=6.6 Hz, 6H), 3H merged in solvent peak.

Step 4: 2-(2-Isobutyl-1-(3'-(methylsulfonyl)-[1,1'-biphenyl]-4-yl)-1H-imidazol-4-yl)propan-2-ol To a stirred solution of the product of the previous step (0.4 g, 0.939 mmol) in dry THF (5 mL) at 0° C., CH$_3$MgBr (2.8 mL, 2.82 mmol) was added, and the reaction was stirred at rt for 16 h. The progress of the reaction was monitored by TLC. Upon completion the reaction mixture was quenched with aqueous sat. NH$_4$Cl solution and extracted with ethyl acetate. The combined organic layers were dried over Na$_2$SO$_4$ and concentrated under reduced pressure. The crude compound was purified by column chromatography to afford the title compound (0.01 g, 2.6%). LCMS: 413.05 (M+1)$^+$; HPLC: 83.25% (@ 210 nm-400 nm) (Rt; 7.467; Method: Triart Basic, Column: YMC Triart C 18 150 mm×4.6 mm×3μ); Mobile Phase: A; 5 mM Ammonium Formate in water+0.1% NH3; B: Acetonitrile+5% Solvent A+0.1% NH3, Inj. Vol: 10 μL, Col. Temp.: Ambient; Flow rate: 1.0 mL/min.; Gradient: 5% B to 95% B in 8 min, Hold till 9.5 min, 1% B in 13.0 min. hold till 15.0 min); $^1$H NMR (400 MHz, DMSO-d6) δ 8.28-8.07 (m, 2H), 8.02-7.88 (m, 3H), 7.84-7.69 (m, 1H), 7.68-7.49 (m, 4H), 7.03 (s, 1H), 4.68 (s, 1H), 2.55 (t, J=8.9 Hz, 2H), 1.93 (dp, J=13.5, 6.8 Hz, 1H), 1.51-1.41 (m, 6H), 0.81 (dd, J=6.6, 1.3 Hz, 6H).

Example 6

Synthesis of 1-isobutyl-5-(3'-(methylsulfonyl)-[1,1'-biphenyl]-4-yl)-3-(prop-1-en-2-yl)-1H-pyrazole (9)

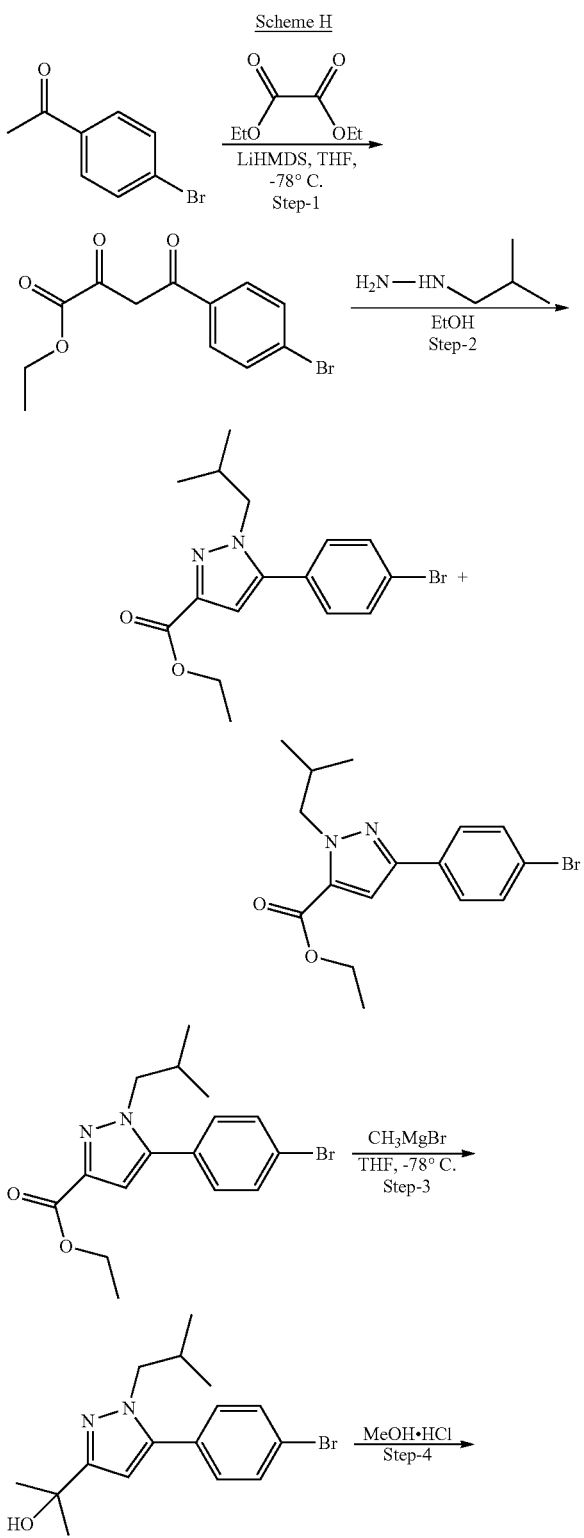

Scheme H

-continued

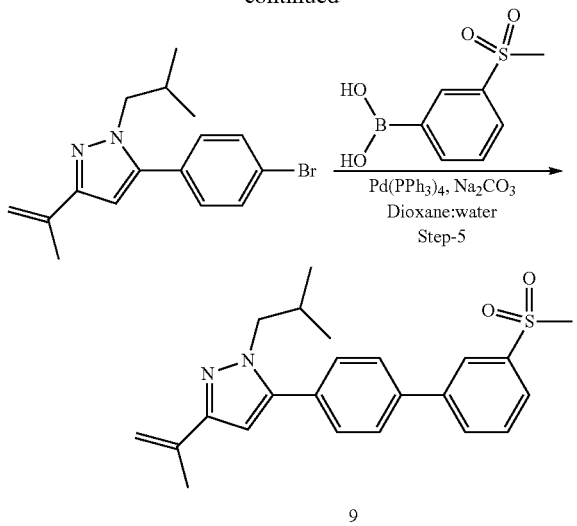

9

Step 1: Ethyl 4-(4-bromophenyl)-2,4-dioxobutanoate

To a stirred solution of 1-(4-bromophenyl)ethanone (5 g, 25.38 mmol) in dry THF (50 mL) at −78° C., LiHMDS (1 M, 28 mL, 27.91 mmol) was added and the solution was stirred at same temperature for 1 h. To this solution, diethyl oxalate (4 g, 27.91 mmol) in THF (10 mL) was added at −78° C. and the resulting reaction mixture was stirred at rt for 12 h. The progress of the reaction was monitored by TLC. Upon completion the reaction mixture was quenched with aqueous sat. NH$_4$Cl solution and extracted with ethyl acetate. The combined organic layers were dried over anhydrous Na$_2$SO$_4$ and concentrated under reduced pressure resulting in a crude compound which was purified by column chromatography to afford the desired compound (2.5 g, 33.3%).

Step 2: Ethyl 5-(4-bromophenyl)-1-isobutyl-1H-pyrazole-3-carboxylate

To a stirred solution of the product of the previous step (1 g, 3.35 mmol) in EtOH (10 mL), isobutyl hydrazine hydrochloride (0.45 g, 3.69 mmol) was added and the resulting reaction mixture was stirred at 80° C. for 3 h. The progress of the reaction was monitored by TLC. Upon completion the reaction mixture was diluted with water and extracted with ethyl acetate. The combined organic layers were dried over anhydrous Na$_2$SO$_4$ and concentrated under reduced pressure resulting in a crude compound which was purified by column chromatography to afford the desired compound (0.7 g, 60%) confirmed by NOE.

Step 3: 2-(5-(4-Bromophenyl)-1-isobutyl-1H-pyrazol-3-yl)propan-2-ol

To a stirred solution of the product of the previous step (0.6 g, 1.71 mmol) in dry THF (10 mL) at 0° C., CH$_3$MgBr (1.4 M, 1.8 mL, 2.57 mmol) was added. The resulting reaction mixture was stirred at rt for 16 h. The progress of the reaction was monitored by TLC. Upon completion the reaction was quenched with aqueous sat. NH$_4$Cl solution and extracted with ethyl acetate. The combined organic layers were dried over anhydrous Na$_2$SO$_4$ and concentrated under reduced pressure resulting in a crude compound which was purified by column chromatography to afford the desired compound (0.55 g, 92%).

Step 4: 5-(4-Bromophenyl)-1-isobutyl-3-(prop-1-en-2-yl)-1H-pyrazole

To a stirred solution of the product of the previous step (0.55 g, 1.63 mmol) and Triethylamine (0.44 mL, 3.32 mmol) in DCM at 0° C., methanesulfonyl chloride (0.19 mL, 2.44 mmol) was added. The resulting reaction mixture was stirred at rt for 3 h. The progress of the reaction was monitored by TLC. Upon completion the reaction mixture was quenched with aqueous sat. sodium bicarbonate solution and extracted with DCM. The combined organic layers were dried over anhydrous Na$_2$SO$_4$ and concentrated under reduced pressure resulting in a crude compound which was purified by column chromatography to afford the desired compound (0.1 g, 19.2%).

Step 5: 1-Isobutyl-5-(3'-(methylsulfonyl)-[1,1'-biphenyl]-4-yl)-3-(prop-1-en-2-yl)-1H-pyrazole (9)

To a stirred solution of the product of the previous step (0.1 g, 0.313 mmol) and (3-(methylsulfonyl)phenyl) boronic acid (0.075 g, 0.376 mmol) in dioxane/water mixture (2 mL+1 mL), Na$_2$CO$_3$ (0.066 g, 0.626 mmol) was added and the solution was purged with argon for 10 min. Then Pd(PPh$_3$)$_4$ (0.036 g, 0.0313 mmol) was added and argon was purged again for 10 min. The reaction mass was heated at 100° C. for 3 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the title compound (0.06 g, 50%). LCMS: 395.20 (M+1)$^+$; HPLC: 97.06% (@ 210 nm-400 nm) (Rt; 10.003; Method: YMC ODS-A (150 mm×4.6 mm×3µ); ID:E-AC-2/13/COL/01, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, CDCl$_3$) δ 8.21 (t, J=1.7 Hz, 1H), 7.99-7.88 (m, 2H), 7.73-7.64 (m, 3H), 7.56-7.47 (m, 2H), 6.43 (s, 1H), 5.54 (s, 1H), 5.10-5.04 (m, 1H), 3.95 (d, J=7.3 Hz, 2H), 3.12 (s, 3H), 2.18 (s, 3H), 1.27 (d, J=15.0 Hz, 1H), 0.78 (d, J=6.6 Hz, 6H).

Example 7

Synthesis of 2-(5-(4'-(Hydroxymethyl)-3'-(methylsulfonyl)-[1,1'-biphenyl]-4-yl)-1-isobutyl-1H-pyrazol-3-yl)propan-2-ol (10)

Scheme I

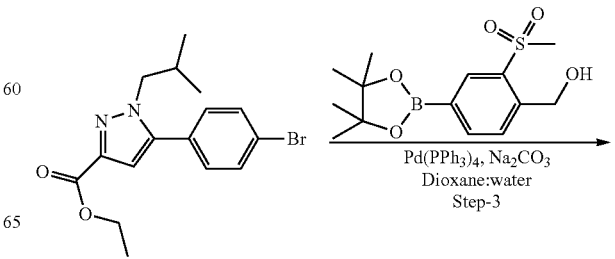

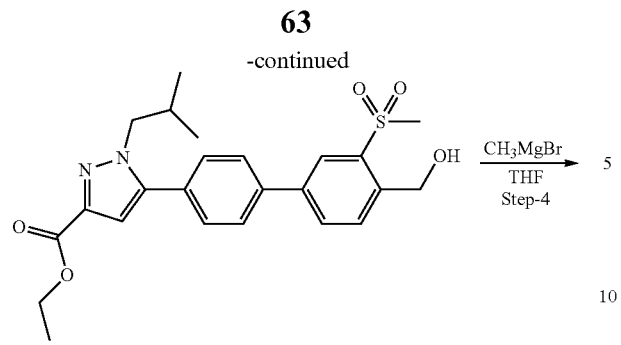

Step 1: Ethyl 5-(4'-(hydroxymethyl)-3'-(methylsulfonyl)-[1,1'-biphenyl]-4-yl)-1-isobutyl-1H-pyrazole-3-carboxylate To a stirred solution of ethyl 5-(4-bromophenyl)-1-isobutyl-1H-pyrazole-3-carboxylate from Example 6, step 1 (1 g, 2.85 mmol) and (2-(methylsulfonyl)-4-(4,4,5,5-tetramethyl-1,3,2-dioxaborolan-2-yl)phenyl)methanol (1.3 g, 4.28 mmol) in dioxane/water mixture (10 mL+4 mL), Na$_2$CO$_3$ (0.76 g, 7.14 mmol) was added and the solution was purged with argon for 10 min. Then Pd (PPh$_3$)$_4$ (0.33 g, 0.285 mmol) was added and argon was purged again for 10 min. The reaction mass was heated at 100° C. for 16 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound (1 g, 77%).

Step 2: 2-(5-(4'-(Hydroxymethyl)-3'-(methylsulfonyl)-[1,1'-biphenyl]-4-yl)-1-isobutyl-1H-pyrazol-3-yl)propan-2-ol To a stirred solution of the product of the previous step (0.3 g, 0.656 mmol) in dry THF (3 mL) at 0° C., CH$_3$MgBr (1.3 mL, 1.31 mmol) was added. The resulting reaction mixture was stirred at rt for 16 h. The progress of the reaction was monitored by TLC. Upon completion the reaction mixture was quenched with aqueous sat. NH$_4$Cl solution and extracted with ethyl acetate. The combined organic layers were dried over anhydrous Na$_2$SO$_4$ and concentrated under reduced pressure resulting in a crude compound which was purified by column chromatography to afford the desired compound (0.16 g, 55.2%). LCMS: 443.30 (M+1)$^+$; HPLC: 95.25% (@ 210 nm-400 nm) (Rt; 7.561; Method: YMC ODS-A (150 mm×4.6 mm×3µ); ID:E-AC-2/13/COL/Ol, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.20-8.07 (m, 2H), 7.93-7.82 (m, 3H), 7.63-7.55 (m, 2H), 6.35 (s, 1H), 5.55 (t, J=5.5 Hz, 1H), 4.97 (d, J=5.5 Hz, 2H), 4.87 (s, 1H), 3.94 (d, J=7.3 Hz, 2H), 3.33 (s, 3H), 2.02 (dt, J=14.6, 7.4 Hz, 1H), 1.46 (s, 6H), 0.72 (d, J=6.7 Hz, 6H).

Example 8

Synthesis 2-(1-isobutyl-5-(3'-(methylsulfonyl)-[1,1'-biphenyl]-4-yl)-1H-pyrazol-3-yl)propan-2-ol (11)

Scheme J

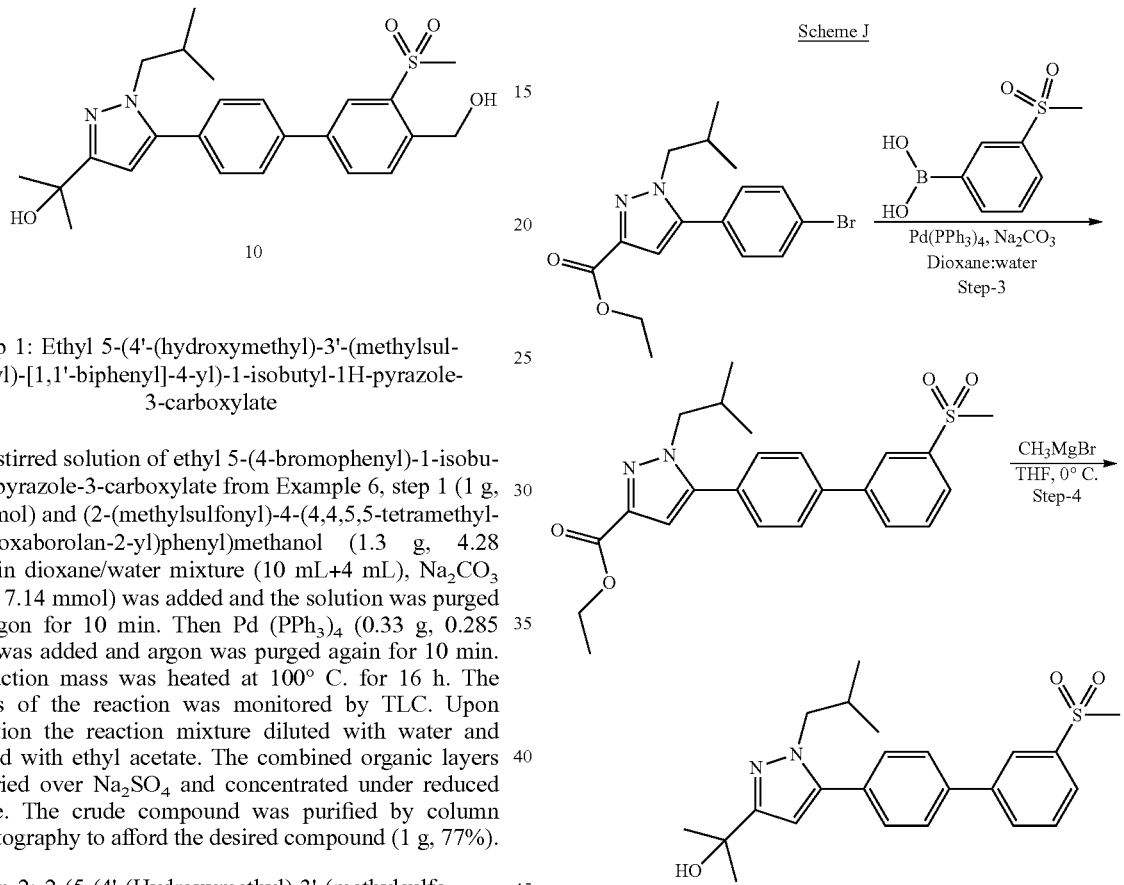

Step 1: Ethyl 1-isobutyl-5-(3'-(methylsulfonyl)-[1,1'-biphenyl]-4-yl)-1H-pyrazole-3-carboxylate To a stirred solution of ethyl 5-(4-bromophenyl)-1-isobutyl-1H-pyrazole-3-carboxylate from Example 6, step 1 (0.4 g, 1.14 mmol) and (3-(methylsulfonyl)phenyl)boronic acid (0.25 g, 1.26 mmol) in dioxane/water mixture (8 mL+2 mL), Na$_2$CO$_3$ (0.3 g, 2.85 mmol) was added and the solution was purged with argon for 10 min. Then Pd (PPh$_3$)$_4$ (0.33 g, 0.285 mmol) was added and argon was purged again for 10 min. The reaction mass was heated at 100° C. for 3 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound (0.28 g, 58.3%).

Step 2: 2-(1-Isobutyl-5-(3'-(methylsulfonyl)-[1,1'-biphenyl]-4-yl)-1H-pyrazol-3-yl)propan-2-ol (11)

To a stirred solution of the product of the previous step (0.28 g, 0.657 mmol) in dry THF (3 mL) at 0° C., CH₃MgBr (0.8 mL, 0.985 mmol) was added. The resulting reaction mixture was stirred at rt for 16 h. The progress of the reaction was monitored by TLC. Upon completion the reaction mixture was quenched with aqueous sat. NH₄Cl solution and extracted with ethyl acetate. The combined organic layers were dried over anhydrous Na₂SO₄ and concentrated under reduced pressure resulting in a crude compound which was purified by column chromatography to afford the title compound (0.08 g, 30%). LCMS: 413.20 (M+1)⁺; HPLC: 97.94% (@ 210 nm-400 nm) (Rt; 8.363; Method: YMC TRIART C-18 (150 mm×4.6 mm×3µ); ID:E-AC-2/13/COL/03, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, CDCl₃) δ 8.21 (d, J=1.9 Hz, 1H), 8.00-7.89 (m, 2H), 7.74-7.64 (m, 2H), 7.54-7.47 (m, 2H), 6.22 (s, 1H), 3.93 (d, J=7.4 Hz, 2H), 3.12 (s, 3H), 2.73 (s, 1H), 2.19 (dt, J=13.9, 6.9 Hz, 1H), 1.62 (s, 6H), 0.78 (d, J=6.6 Hz, 6H).

Example 9

Synthesis of 1-isobutyl-3-isopropyl-5-(3'-(methylsulfonyl)-[1,1'-biphenyl]-4-yl)-1H-pyrazole (12)

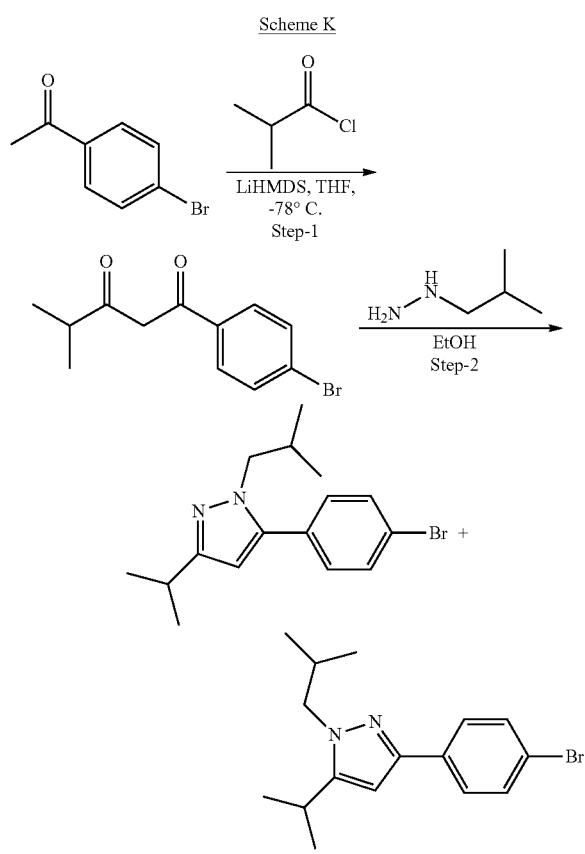

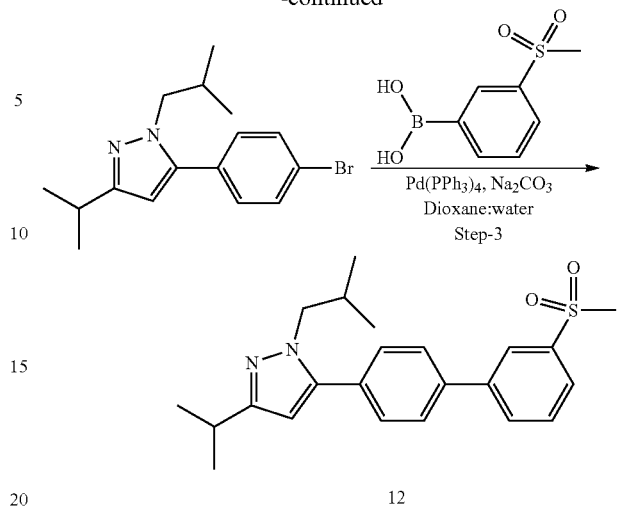

Step 1:
1-(4-Bromophenyl)-4-methylpentane-1,3-dione

To a stirred solution of 1-(4-bromophenyl)ethanone (2 g, 10.05 mmol) in dry THF (20 mL) at −78° C., LiHMDS (2 M, 30 mL, 15.07 mmol) was added and the solution was stirred at same temperature for 1 h. To this solution, isobutyryl chloride (1.53 g, 15.07 mmol) in THF (10 mL) was added at −78° C. and the resulting reaction mixture was stirred at rt for 12 h. The progress of the reaction was monitored by TLC. Upon completion the reaction mixture was quenched with aqueous sat. NH₄Cl solution and extracted with ethyl acetate. The combined organic layers were dried over anhydrous Na₂SO₄ and concentrated under reduced pressure resulting in a crude compound which was purified by column chromatography to afford the desired compound (2 g, 68%).

Step 2: 5-(4-Bromophenyl)-1-isobutyl-3-isopropyl-1H-pyrazole

To a stirred solution of the product of the previous step (0.9 g, 3.35 mmol) in EtOH (10 mL), isobutylhydrazine (0.325 g, 3.69 mmol) was added and the resulting reaction mixture was stirred at 80° C. for 3 h. The progress of the reaction was monitored by TLC. Upon completion the reaction mixture was diluted with water and extracted with ethyl acetate. The combined organic layers were dried over anhydrous Na₂SO₄ and concentrated under reduced pressure resulting in a crude compound which was purified by column chromatography to afford the desired compound (0.36 g, 34%) confirmed by NOE.

Step 3: 1-Isobutyl-3-isopropyl-5-(3'-(methylsulfonyl)-[1,1'-biphenyl]-4-yl)-1H-pyrazole (12)

To a stirred solution of the product of the previous step (0.36 g, 1.12 mmol) and (3-(methylsulfonyl)phenyl)boronic acid (0.27 g, 1.34 mmol) in dioxane/water mixture (4 mL+2 mL), Na₂CO₃ (0.24 g, 2.24 mmol) was added and the solution was purged with argon for 10 min. Then Pd (PPh₃)₄ (0.13 g, 0.112 mmol) was added and argon was purged again for 10 min. The reaction mass was heated at 100° C. for 3 h. The progress of the reaction was monitored by TLC.

Upon completion the reaction mixture diluted with water and extracted with ethyl acetate. The combined organic layers were dried over Na$_2$SO$_4$ and concentrated under reduced pressure. The crude compound was purified by column chromatography to afford the desired compound (0.08 g, 18.2%). LCMS: 397.25 (M+1)$^+$; HPLC: 94.95% (@ 210 nm-400 nm) (Rt; 9.404; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.26-8.20 (m, 1H), 8.15-8.06 (m, 1H), 7.91 (dd, J=19.2, 8.2 Hz, 3H), 7.78 (q, J=7.9, 6.3 Hz, 1H), 7.60 (d, J=8.1 Hz, 2H), 6.25 (s, 1H), 3.93 (d, J=7.2 Hz, 2H), 3.31 (s, 3H), 2.92 (h, J=6.9 Hz, 1H), 2.04 (dp, J=13.7, 6.6 Hz, 1H), 1.23 (d, J=6.8 Hz, 6H), 0.71 (d, J=6.6 Hz, 6H).

Additional pyrazole compounds as shown in the table below can be made by methods analogous to those used to make Compound 10 in Example 7.

| Compound No. | Name | Structure | Mol. Wt. |
|---|---|---|---|
| 13 | (4'-(1-isobutyl-3-(prop-1-en-2-yl)-1H-pyrazol-5-yl)-3-(methylsulfonyl)-[1,1'-biphenyl]-4-yl)methanol | 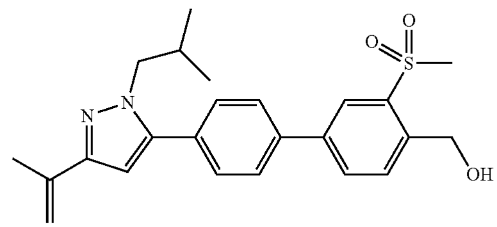 [SMILES: CC(C)Cn1nc(C(C)C)cc1-c1ccc(-c2ccc(CO)c(S(C)(=O)=O)c2)cc1] | 424.18 |
| 14 | (4'-(1-isobutyl-3-isopropyl-1H-pyrazol-5-yl)-3-(methylsulfonyl)-[1,1'-biphenyl]-4-yl)methanol | 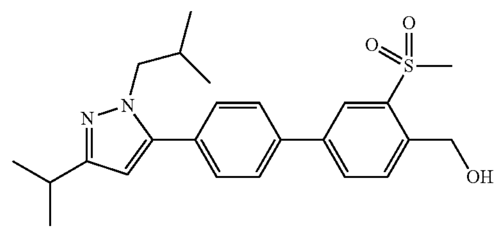 | 426.2 |

Additional imidazole compounds as shown in the table below can be made by methods analogous to those used to make Compound 8 in Example 5

| Compound No. | Name | Structure | Mol. Wt. |
|---|---|---|---|
| 15 | 2-isobutyl-1-(3'-(methylsulfonyl)-[1,1'-biphenyl]-4-yl)-4-(trifluoromethyl)-1H-imidazole | 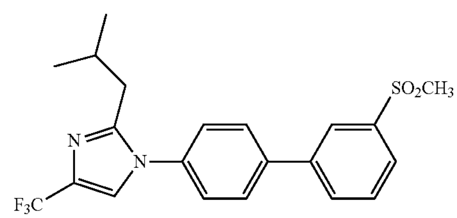 [SMILES: CC(C)Cc1nc(C(F)(F)F)cn1-c1ccc(-c2cccc(S(C)(=O)=O)c2)cc1] | 422.13 |
| 16 | 2-(1-(4'-(hydroxymethyl)-3'-(methylsulfonyl)-[1,1'-biphenyl]-4-yl)-2-isobutyl-1H-imidazol-4-yl)propan-2-ol | 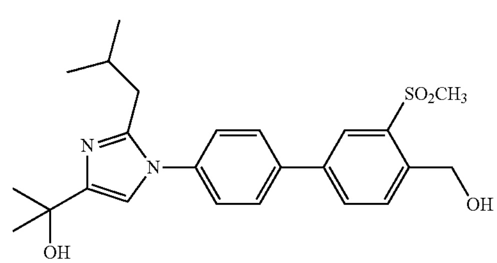 [SMILES: CC(C)Cc1nc(C(C)(C)O)cn1-c1ccc(-c2ccc(CO)c(S(C)(=O)=O)c2)cc1] | 442.19 |

| Compound No. | Name | Structure | Mol. Wt. |
|---|---|---|---|
| 17 | (4'-(2-isobutyl-4-(trifluoromethyl)-1H-imidazol-1-yl)-3-(methylsulfonyl)-[1,1'-biphenyl]-4-yl)methanol | 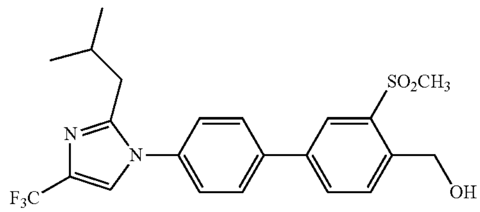 [SMILES: CC(C)Cc1nc(C(F)(F)F)cn1-c1ccc(-c2ccc(CO)c(S(C)(=O)=O)c2)cc1] | 452.14 |

Example 10

Synthesis of Compounds 18-21

Compounds 18-21 can be synthesized as shown in Scheme L below.

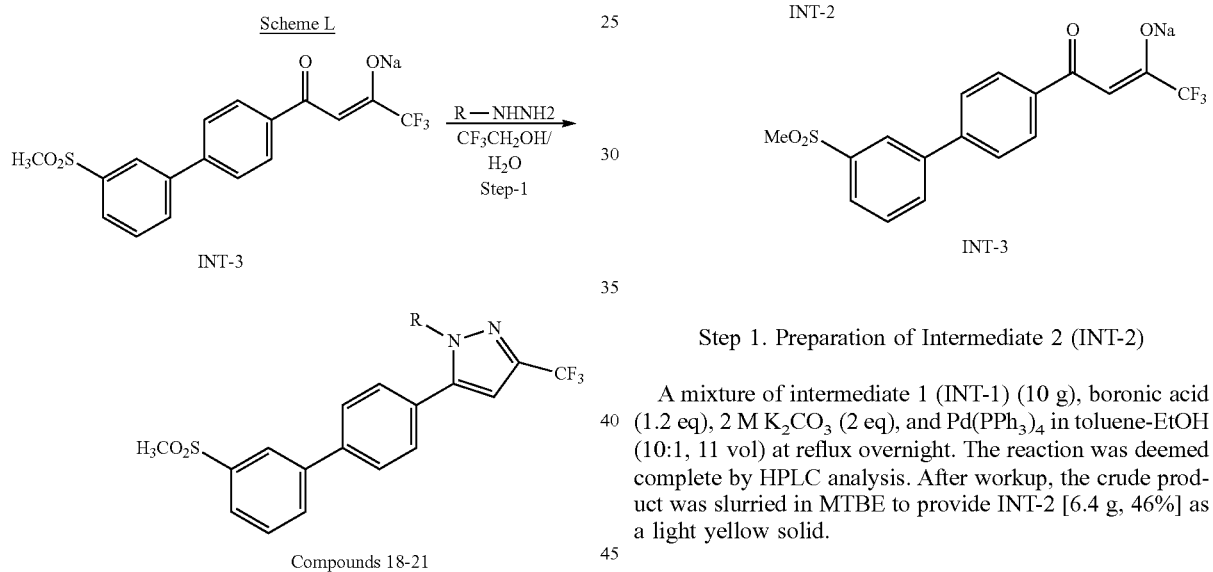

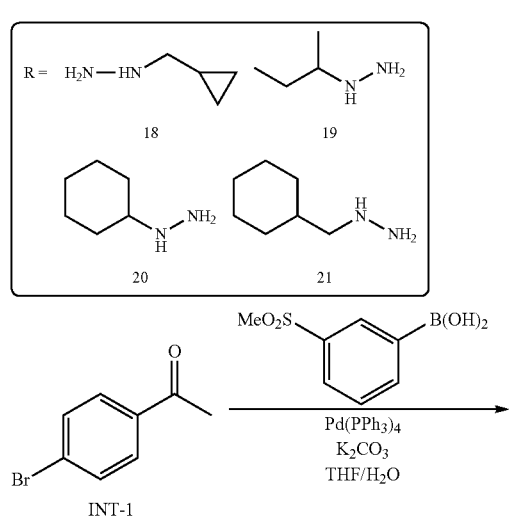

Step 1. Preparation of Intermediate 2 (INT-2)

A mixture of intermediate 1 (INT-1) (10 g), boronic acid (1.2 eq), 2 M K₂CO₃ (2 eq), and Pd(PPh₃)₄ in toluene-EtOH (10:1, 11 vol) at reflux overnight. The reaction was deemed complete by HPLC analysis. After workup, the crude product was slurried in MTBE to provide INT-2 [6.4 g, 46%] as a light yellow solid.

Step 2. Preparation of Intermediate 3 (INT-3)

To 5.5 g of intermediate 2 (INT-2) in 100 mL THF was added NaOMe (2.2 eq.) followed by ethyltrifluoroacetate (1.3 eq.) and the reaction stirred overnight at room temperature. The reaction mixture was filtered and the residue was washed with MTBE to provide INT-3 as a off-white solid (85% yield) which was used in the synthesis of compounds 18-21.

Step 3. General Procedure for Synthesis of Target Compounds 18-21

To a stirred solution of compound INT-3 (100 mg, 1 eq) in trifluoroethanol: water (2:1) mixture, respective hydrazine hydrochloride (1 eq) in water was added and the resulting reaction mixture was stirred at rt for 16 h. The progress of the reaction was monitored by TLC and LCMS. Upon completion the reaction mixture was quenched with water and extracted with ethyl acetate. The combined organic layers were washed with brine; dried over anhydrous Na₂SO₄ and concentrated under reduced pressure resulting in a crude compound which was purified by column chromatography to afford the target compounds 18-21, which are confirmed by NOE experiment. The structures of compounds 18-21 are shown in the table below.

| Compound No. | Name | Structure |
|---|---|---|
| 18 | 1-(cyclopropylmethyl)-5-(3'-(methylsulfonyl)-[1,1'-biphenyl]-4-yl)-3-(trifluoromethyl)-1H-pyrazole | 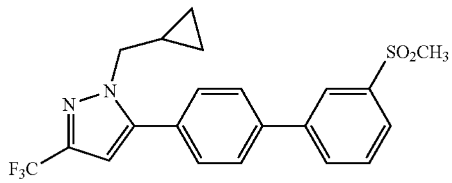 [SMILES: CS(=O)(=O)c1cccc(-c2ccc(-c3cc(C(F)(F)F)nn3CC3CC3)cc2)c1] |
| 19 | 1-(sec-butyl)-5-(3'-(methylsulfonyl)-[1,1'-biphenyl]-4-yl)-3-(trifluoromethyl)-1H-pyrazole | 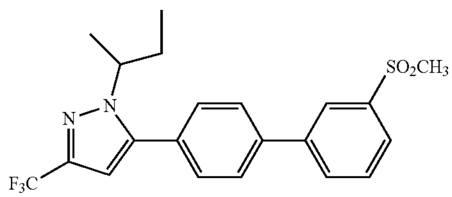 [SMILES: CCC(C)n1nc(C(F)(F)F)cc1-c1ccc(-c2cccc(S(C)(=O)=O)c2)cc1] |
| 20 | 1-cyclohexyl-5-(3'-(methylsulfonyl)-[1,1'-biphenyl]-4-yl)-3-(trifluoromethyl)-1H-pyrazole | 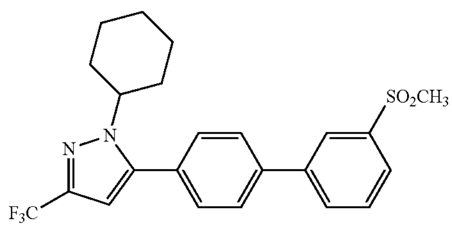 [SMILES: CS(=O)(=O)c1cccc(-c2ccc(-c3cc(C(F)(F)F)nn3C3CCCCC3)cc2)c1] |
| 21 | 1-(cyclohexylmethyl)-5-(3'-(methylsulfonyl)-[1,1'-biphenyl]-4-yl)-3-(trifluoromethyl)-1H-pyrazole | 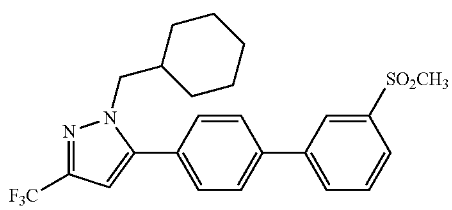 [SMILES: CS(=O)(=O)c1cccc(-c2ccc(-c3cc(C(F)(F)F)nn3CC3CCCCC3)cc2)c1] |

Analytical Data of Compound 18: LCMS: 421.30 (M+1)+; HPLC: 99.28% (@ 210 nm-400 nm) (Rt; 9.800; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 5% B to 95% B in 8 min, Hold till 9.5 min, 5% B in 13.0 min. hold till 15.0 min); $^1$H NMR (400 MHz, DMSO-d6) δ 8.25 (t, J=1.7 Hz, 1H), 8.17-8.09 (m, 1H), 8.00-7.91 (m, 3H), 7.83-7.67 (m, 3H), 6.95 (s, 1H), 4.14 (d, J=7.0 Hz, 2H), 1.26-1.08 (m, 1H), 0.51-0.39 (m, 2H), 0.27-0.16 (m, 2H).

Analytical Data of Compound 19: LCMS: 423.00 (M+1)+; HPLC: 98.99% (@ 210 nm-400 nm) (Rt; 10.208; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.24 (d, J=1.9 Hz, 1H), 8.12 (dt, J=7.8, 1.4 Hz, 1H), 7.96 (dq, J=8.5, 2.2, 1.8 Hz, 3H), 7.79 (t, J=7.8 Hz, 1H), 7.67-7.58 (m, 2H), 6.89 (s, 1H), 4.35 (ddd, J=13.1, 10.4, 6.2 Hz, 1H), 1.87 (ddd, J=13.7, 8.8, 7.1 Hz, 1H), 1.79-1.64 (m, 1H), 1.47 (d, J=6.5 Hz, 3H), 0.59 (t, J=7.3 Hz, 3H).

Analytical Data of Compound 20: LCMS: 449.00 (M+1)+; HPLC: 99.17% (@ 210 nm-400 nm) (Rt; 10.663; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 5% B to 95% B in 8 min, Hold till 9.5 min, 5% B in 13.0 min. hold till 15.0 min); $^1$H NMR (400 MHz, DMSO-d6) δ 8.25 (d, J=1.9 Hz, 1H), 8.13 (d, J=8.0 Hz, 1H), 7.96 (d, J=8.1 Hz, 3H), 7.79 (t, J=7.8 Hz, 1H), 7.65 (d, J=8.0 Hz, 2H), 6.89 (s, 1H), 4.24 (ddt, J=11.2, 8.2, 4.1 Hz, 1H), 2.00-1.75 (m, 6H), 1.62 (d, J=8.9 Hz, 1H), 1.27 (dtt, J=19.7, 14.0, 7.4 Hz, 3H).

Analytical Data of Compound 21: LCMS: 463.35 (M+1)+; HPLC: 98.65% (@ 210 nm-400 nm) (Rt; 11.278; Method: Column: YMC ODS-C-18 150 mm×4.6 mm×3μ); Mobile Phase: A; 5 mM Ammonium Formate in water+0.1% Formic acid; B: Acetonitrile+5% Solvent A+0.1% Formic acid, Inj. Vol: 10 μL, Col. Temp.: Ambient; Flow rate: 1.0 mL/min.; Gradient: 5% B to 95% B in 8 min, Hold till 13 min, at 15.00 min % B is 5% hold up to 18); $^1$H NMR (400 MHz, DMSO-d6) δ 8.26 (t, J=1.9 Hz, 1H), 8.14 (dt, J=7.9, 1.4 Hz, 1H), 8.00-7.92 (m, 3H), 7.79 (t, J=7.8 Hz, 1H), 7.73-7.64 (m, 2H), 6.93 (s, 1H), 4.10 (d, J=7.2 Hz, 2H), 3.32 (s, 3H), 1.90-1.80 (m, 1H), 1.57 (d, J=13.7 Hz, 3H), 1.42 (dd, J=12.7, 3.5 Hz, 2H), 1.15-1.09 (m, J=3H), 0.90-0.73 (m, 2H).

Example 11

RNA Extraction

Add QIAzol® Lysis Reagent (QIAGEN Cat Number 79306) to the cells. Scrape the cells and place into a Falcon Polypropylene tube. Let stand at room temperature for 5 minutes. Add 1 ml of cells to microfuge tubes. Add 200 µl of chloroform, vortex, let stand for 5 minutes. Centrifuge at 4° C. for 15 minutes at 14,000 RPM. Add an equal volume of 70% ETOH (diluted with DEPC water). Add 600 µl to the RNeasy® column from the RNeasy® Mini Kit (QIAGEN Cat. Number 74106) centrifuge at 14,000 RPM at room temperature for 1 minute, discard flow-through. Add remainder of sample to the column, centrifuge, discard flow-through. Add 350 µl of RW1 buffer from the RNeasy® Mini Kit to the column, centrifuge at room temperature for 1 minute, discard flow-through. DNase column with RNase-Free DNase Set (QIAGEN cat. Number 79254) by making DNase I stock solution, add 550 µl of water to the DNase, add 10 µl of DNase to 70 µl of BufferRDD for each sample, mix, add 80 µl to the column, let stand for 15 minutes. Add 350 µl of RW1 buffer to column, centrifuge for 1 minute, discard flow-through. Add 500 µl RPE buffer to column, centrifuge for 1 minute, discard flow-through. Add 500 µl RPE buffer to column, centrifuge for 1 minute, discard flow-through. Put column into a clean 2.0 ml microfuge tube, centrifuge for 2 minutes. Put column into a microfuge tube, add 50 µl of water, allow column to stand for 2 minutes, centrifuge for 1 minute.

Quantitative PCR

TaqMan technology is used for quantitative PCR for the evaluation of MMP, TNFα, TIMP, IL-8, ASAH1, SPTLC1, SMPD1, LASS2, TXNRD1, GPX3, GSR, CAT, ApoE, ABCA1, ABCA2, ABCA12, ABCA13, ABCG1, αSyn, decorin, and LXRα/β gene expression.

Conditions for use of TaqMan Reverse Transcriptase Reagents (Applied Biosystems Cat. Number N808-0234): 10×RT buffer: 10 µl, MgCl$_2$ solution: 22 µl, DNTP mix: 20 µl, Random Hexamers: 5 µl, Multi Scribe RT: 2.5 µl, RNase Inhibitor: 2.5 µl, 2 µg RNA. Thermocycler: 25° C.-10 minutes, 48° C.-30 minutes, 95° C.-5 minutes.

Setup TaqMan with QuantiTect Multiplex PCR Kit (QIAGEN cat. Number 204543): 2× master mix: 25 µl; Single Tube Assay: 2.5 µl; Applied Biosystems Primers Probe set (part number 4308329)—18S forward primer: 0.25 µl, 18S reverse primer: 0.25 µl, 18S probe: 0.25 µl; water to 50 µl; 5 µl cDNA. Thermocycler: 50° C.-2 minutes, 95° C.-10 minutes, 95° C.-15 seconds, 60° C.-1 minute.

Example 12

Induction of Expression of LXR Receptors

Clonetics® Normal Human Epidermal Keratinocytes (NHEKs) are obtained from Cambrex Bio Science, Inc. The proliferating T-25 (C2503TA25) pooled, neonatal keratinocytes are expanded in Clonetics® KGM-2 serum-free medium (CC-3107) and subcultured as needed using the recommended Clonetics® ReagentPack™ (CC-5034). Due to a light-sensitive component in the medium, all manipulations are done in low light.

For experiments, 1.6 million NHEK cells are plated in growth medium on 100 mm dishes and allowed to grow to 75% confluence. On the day of treatment, the dishes are rinsed once with KGM-2 minus hydrocortisone; then, vehicle (0.1% DMSO) or 1 µM or an LXR agonist described herein, is added for 6 h in hydrocortisone-deficient KGM-2. After 6 h, the treatment medium is temporarily removed, the dishes washed with Dulbecco's Phosphate Buffered Saline, and then half of the treatments are exposed to 8 J/m$^2$ ultraviolet light using a Stratagene UV Stratalinker® 2400. Treatments are replaced and 18 h later the samples are harvested for RNA processing using TRIzol®D Reagent (Invitrogen).

RNA is extracted as described above. UV irradiation of NHEKs slightly reduced the expression of LXRa. Treatment of keratinocytes with the LXR modulator (1 µM) induces the expression of LXRα in both UV-unexposed and UV-exposed keratinocytes. UV treatment of NHEKs down-regulates LXRβ expression, and this UV-mediated inhibition of LXRβ expression is reversed by treatment with the LXR modulator. Therefore, induction of expression of both LXR receptors in UV-exposed keratinocytes by an LXR modulator indicates efficacy of the LXT modulator. Further, LXR modulators may help the UV-exposed keratinocytes/skin to be more responsive to its effects.

Gal4 LXRβ Cotransfection Assay

For transient transfection of HEK 293 cells, 6×10$^3$ cells are plated into 96-well dishes. Each well is transfected with 25 ng 5×UAS-luciferase reporter (pG5luc) and 25 ng of pM human LXRβ (AA 153-461) LBD plasmid using Fugene 6 reagent (Roche; Indianapolis, Ind.). The chimeric protein is assessed for the ability to transactivate a Ga14-responsive luciferase reporter plasmid in a concentration-responsive manner to compounds (0.01-10 µM). Luciferase activity at each dose concentration is measured in triplicate using standard substrate reagents (BD Biosciences; San Diego, Calif.). Data is expressed as relative light units and are shown in Table 1.

TABLE 1

EC$_{50}$ values for LXR modulators in LXRβ Gal fusion assay

| Compound | LXRβ Gal (EC$_{50}$) µM |
|---|---|
| 4 | A |
| 5 | A |
| 6 | A |
| 7 | A |
| 8 | B |
| 9 | B |
| 10 | B |
| 11 | B |
| 12 | B |
| 18 | A |
| 19 | C |
| 20 | C |
| 21 | A |

A: EC$_{50}$ <1 µM;
B: EC$_{50}$ 1-10 µM;
C: EC$_{50}$ >10 µM

Example 13

ABCA1 and ABCG1 Expression

Mice (C57b1/6) were given a peritoneal injection of 10 mg/kg LPS with SQ injection of vehicle, or LXR agonist in mice. Microglia microdissection of substantial nigra and analysis of gene expression by QT-PCR were carried out (N=4 for each treatment). Brain and peripheral blood lymphocytes (PBL) were analyzed for ABCA1 and ABCG1 as per published protocol (Gustafsson, J. A.; *Proc. Natl. Acad.*

Figure 2:
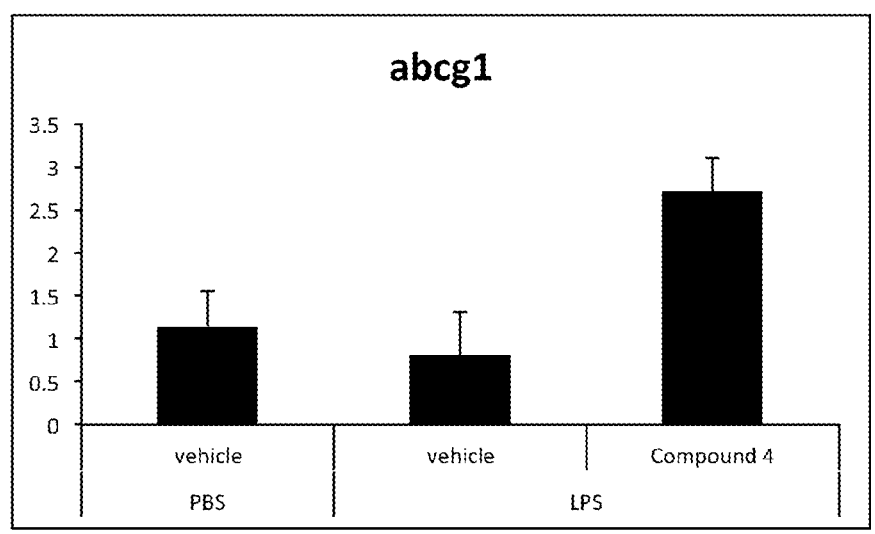
FIG. 2 shows ABCG1 gene expression analyzed by QT-PCR for Compound 4 as outlined in Example 13.

Sci. U.S.A. (2012) 109:13112-13117). In this manner, Compound 4 was administered at 20 mg/kg. Results are shown in FIGS. 1 and 2.

Example 14

IL1β Expression

Figure 3:
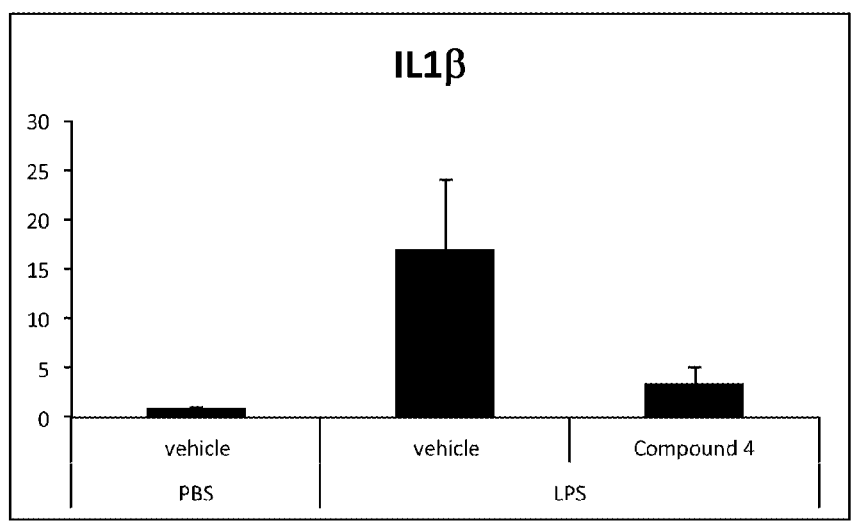
FIG. 3 shows IL1β gene expression analyzed by QT-PCR for Compound 4 as outlined in Example 14.

Following the protocol outlined in Example 13, IL113 expression of Compound 4 was measured in the brain and PBL. Results are shown in FIG. 3.

Example 15

αSynuclein (αSyn) Expression

Figure 4:
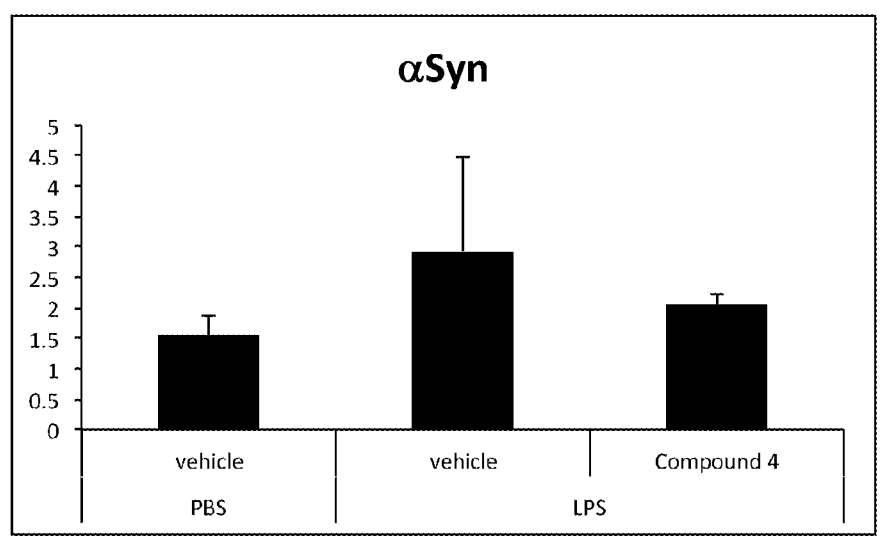
FIG. 4 shows αSyn gene expression analyzed by QT-PCR for Compound 4 as outlined in Example 15.

Following the protocol outlined in Example 13, αSyn expression of Compound 4 was measured in the brain. Results are shown in FIG. 4.

Example 16

Regulation of ApoE Gene Expression

BV2 microglia cells were treated with Compound 4 at various concentrations for 48 h, respectively with 0.1% DMSO as the vehicle control. Whole cell lysates were prepared, and apoE proteins were detected by using apoE antibody. These experiments were repeated at least twice independently, and representative immunoblots were shown. Bands from dose-response blots were quantified by densitometry, normalized to β-actin, and expressed as fold of vehicle treatment. Data are represented as mean±SEM.

The examples and embodiments described herein are for illustrative purposes only and in some embodiments, various modifications or changes are to be included within the purview of disclosure and scope of the appended claims.

What is claimed is:
1. A compound of Formula (IA):

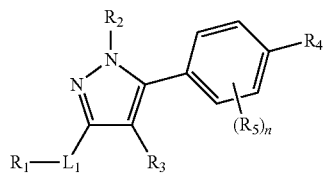

(IA)

or a pharmaceutically acceptable salt thereof, wherein:
$L_1$ is a bond;
$R_1$ is —$OR_9$, —$N(R_9)_2$, $C_1$-$C_6$alkyl, $C_2$-$C_6$alkenyl, $C_1$-$C_6$haloalkyl, $C_2$-$C_9$heterocycloalkyl, —C(=O)$R_8$, or —C(=O)$N(R_9)_2$;
$R_2$ is $C_1$-$C_6$alkyl, $C_2$-$C_6$alkenyl, $C_3$-$C_8$cycloalkyl, or —$C_1$-$C_6$alkyl-$C_3$-$C_8$cycloalkyl;
$R_3$ is hydrogen or halogen;
$R_4$ is aryl; wherein aryl is substituted with at least one $R_{11}$;
each $R_5$ is independently halogen, $C_1$-$C_6$alkyl, or $C_1$-$C_6$haloalkyl;
$R_8$ is $C_1$-$C_6$alkyl, $C_2$-$C_6$alkenyl, $C_1$-$C_6$haloalkyl, —$C_1$-$C_6$alkyl-aryl, aryl, or heteroaryl;
each $R_9$ is independently hydrogen or $C_1$-$C_6$haloalkyl;
each $R_{10}$ is independently hydrogen or $C_1$-$C_6$alkyl;
each $R_{11}$ is independently halogen, nitro, —$OR_{10}$, —$N(R_{10})_2$, —CN, —C(=O)$R_{10}$, —C(=O)$OR_{10}$, —C(=O)$N(R_{10})_2$, —$NR_{10}C(=O)R_{10}$, —$NR_{10}SO_2R_{10}$, —$SOR_{10}$, —$SO_2R_{10}$, —$SO_2N(R_{10})_2$, —C(=O)OCH$_2$SCH$_3$, optionally substituted $C_1$-$C_6$alkyl, or optionally substituted $C_1$-$C_6$haloalkyl;
provided that at least one $R_{11}$ is —$NR_{10}SO_2R_{10}$, —$SOR_{10}$, —$SO_2R_{10}$, or —$SO_2N(R_{10})_2$; and
n is 0.
2. The compound of claim 1, wherein the compound is a compound of Formula (IB):

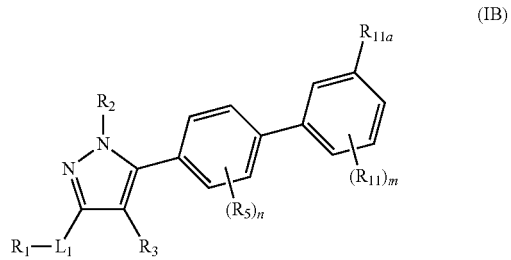

(IB)

wherein:
$R_{11a}$ is —$NR_{10}SO_2R_{10}$, —$SO_2R_{10}$, or —$SO_2N(R_{10})_2$; and
m is 0 or 1;
or a pharmaceutically acceptable salt thereof.
3. The compound of claim 1, wherein the compound is a compound of Formula (IC):

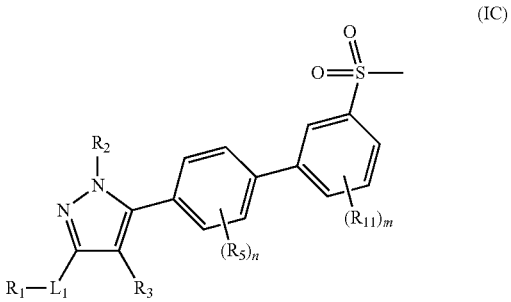

(IC)

wherein m is 0 or 1;
or a pharmaceutically acceptable salt thereof.
4. The compound of claim 1, or a pharmaceutically acceptable salt thereof, wherein:
$L_1$ is a bond or $C_1$-$C_6$alkyl;
$R_1$ is —$OR_9$, —$C_1$-$C_6$alkyl, $C_2$-$C_6$alkenyl, $C_1$-$C_6$haloalkyl, or —C(=O)$N(R_9)_2$;
$R_2$ is $C_1$-$C_6$alkyl, $C_3$-$C_8$cycloalkyl, or —$C_1$-$C_6$alkyl-$C_3$-$C_8$cycloalkyl;
$R_3$ is hydrogen;
$R_4$ is phenyl substituted with at least one $R_{11}$;
each $R_{11}$ is independently —$NR_{10}SO_2R_{10}$, —$SOR_{10}$, —$SO_2R_{10}$, —$SO_2N(R_{10})_2$, or $C_1$-$C_6$alkyl, wherein said $C_1$-$C_6$alkyl is optionally substituted by 1 hydoxy;
provided that at least one $R_{11}$ is —$NR_{10}SO_2R_{10}$, —$SOR_{10}$, —$SO_2R_{10}$, or —$SO_2N(R_{10})_2$,
each $R_{10}$ is independently $C_1$-$C_6$ alkyl; and
each $R_9$ is independently hydrogen or $C_1$-$C_6$haloalkyl; and
n is 0.
5. The compound of claim 1, or a pharmaceutically acceptable salt thereof, wherein:

L₁ is a bond or $C_1$-$C_6$alkyl;

R₁ is —OR₉, —$C_1$-$C_6$alkyl, $C_2$-$C_6$alkenyl, $C_1$-$C_6$haloalkyl, or —C(=O)N(R₉)₂;

R₂ is $C_1$-$C_6$alkyl, $C_3$-$C_8$cycloalkyl, or —$C_1$-$C_6$alkyl-$C_3$-$C_8$cycloalkyl;

R₃ is hydrogen;

R₄ is phenyl substituted with one R₁₁, wherein R₁₁ is —SO₂R₁₀ and R₁₀ is $C_1$-$C_6$alkyl; or R₄ is phenyl substituted with two R₁₁, wherein one R₁₁ is —SO₂R₁₀ and one R₁₁ is optionally substituted $C_1$-$C_6$alkyl;

each R₉ is independently hydrogen or $C_1$-$C_6$haloalkyl; and n is 0.

6. The compound of claim 1, or a pharmaceutically acceptable salt thereof, wherein:

-L₁-R₁ is C(=CH₂)CH₃, isopropyl, —C(=O)NHCH₂CF₃, —CF₃, or C(CH₃)₂OH;

R₂ is isobutyl, sec-butyl, cyclohexyl, —CH₂-cyclohexyl, or —CH₂-cyclopropyl;

R₃ is hydrogen;

R₄ is phenyl substituted with two R₁₁, wherein one R₁₁ is —SO₂CH₃ and one R₁₁ is —CH₂OH; or R₄ is phenyl substituted with one R₁₁, wherein R₁₁ is —SO₂R₁₀ and R₁₀ is CH₃; and n is 0.

7. The compound of claim 1, selected from:

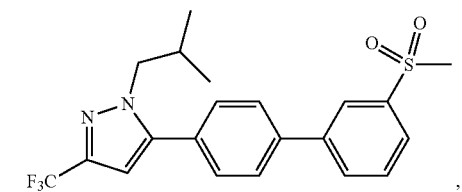

,

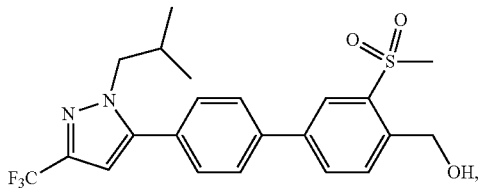

,

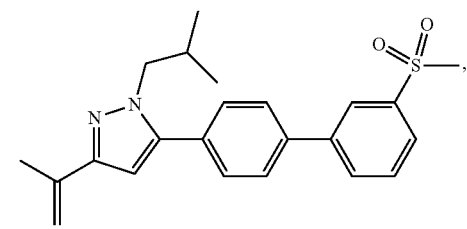

,

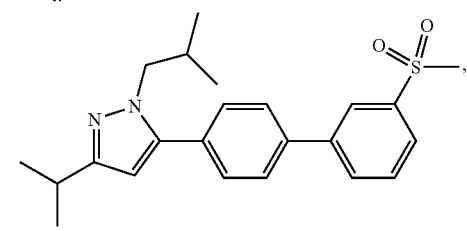

,

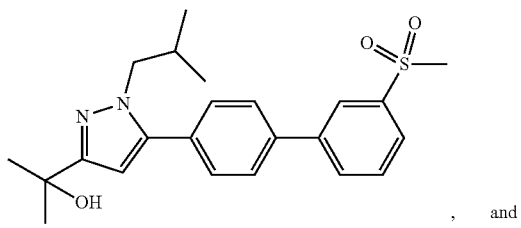

, and

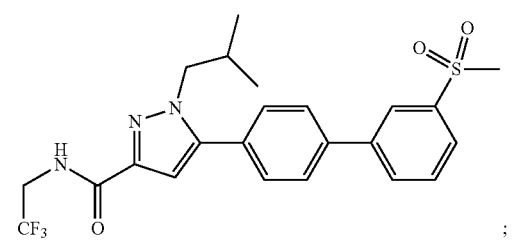

;

or a pharmaceutically acceptable salt thereof.

8. The compound of claim 1, selected from:

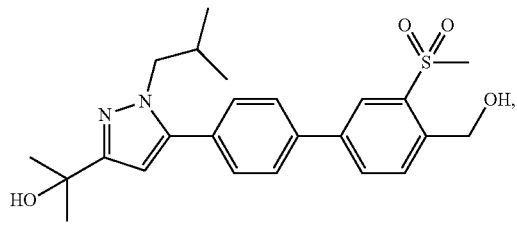

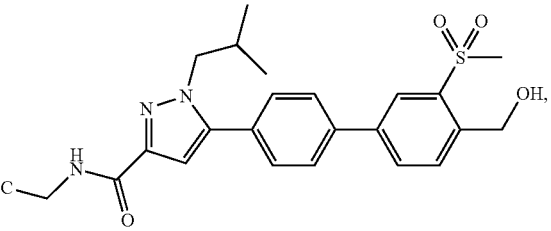

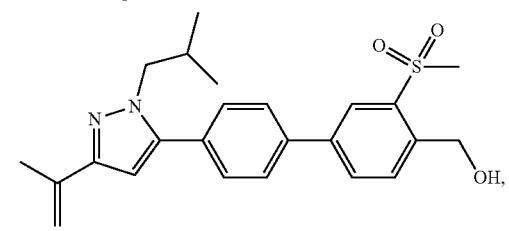

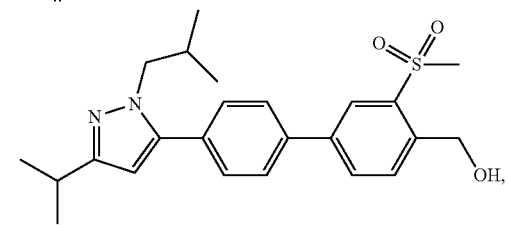

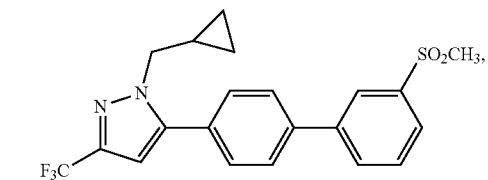

-continued

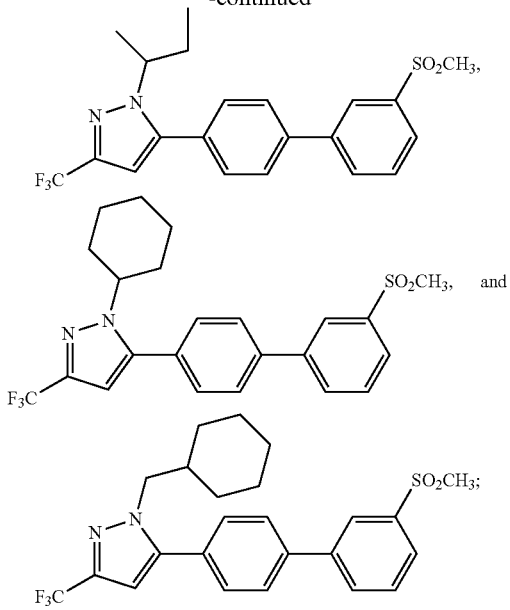

or a pharmaceutically acceptable salt thereof.

9. The compound of claim 1, selected from:

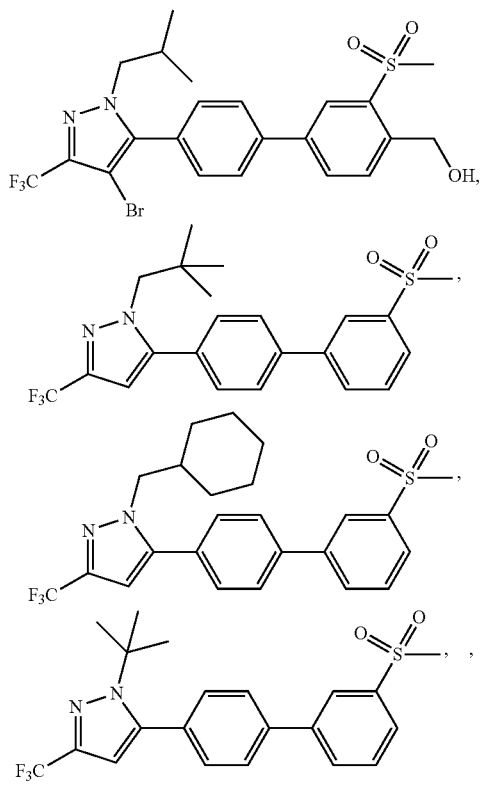

-continued

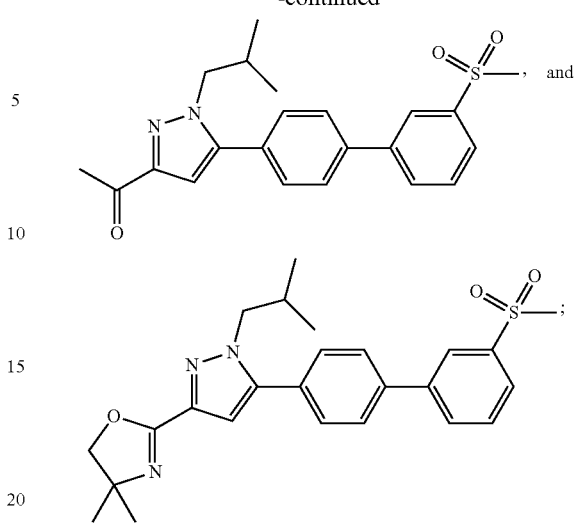

or a pharmaceutically acceptable salt thereof.

10. A pharmaceutical composition comprising a compound according to claim 1, or a pharmaceutically acceptable salt thereof, and a pharmaceutically acceptable carrier.

11. A method of modulating LXR activity comprising contacting LXR, or portion thereof, with a compound according to claim 1, or a pharmaceutically acceptable salt thereof.

12. The compound of claim 1, or a pharmaceutically acceptable salt thereof, wherein $R_1$ is $C_1$-$C_6$alkyl.

13. The compound of claim 1, or a pharmaceutically acceptable salt thereof, wherein $R_1$ is $C_2$-$C_6$alkenyl.

14. The compound of claim 1, or a pharmaceutically acceptable salt thereof, wherein $R_1$ is $C_1$-$C_6$haloalkyl.

15. The compound of claim 1, or a pharmaceutically acceptable salt thereof, wherein -$L_1$-$R_1$ is —C(=CH$_2$)CH$_3$, isopropyl, —C(=O)NHCH$_2$CF$_3$, —CF$_3$, or —C(CH$_3$)$_2$OH.

16. The compound of claim 1, or a pharmaceutically acceptable salt thereof, wherein $R_2$ is $C_1$-$C_6$alkyl.

17. The compound of claim 1, or a pharmaceutically acceptable salt thereof, wherein $R_2$ is isobutyl, sec-butyl, cyclohexyl, —CH$_2$-cyclohexyl, or —CH$_2$-cyclopropyl.

18. The compound of claim 1, or a pharmaceutically acceptable salt thereof, wherein each $R_{10}$ is independently $C_1$-$C_6$alkyl.

19. The compound of claim 1, or a pharmaceutically acceptable salt thereof, wherein $R_4$ is phenyl substituted with one $R_{11}$, wherein $R_{11}$ is —SO$_2$R$_{10}$ and $R_{10}$ is $C_1$-$C_6$alkyl; or $R_4$ is phenyl substituted with two $R_{11}$, and one $R_{11}$ is —SO$_2$R$_{10}$; and one $R_{11}$ is optionally substituted $C_1$-$C_6$alkyl.

* * * * *